US012167858B2

(12) United States Patent
Whalen

(10) Patent No.: US 12,167,858 B2
(45) Date of Patent: *Dec. 17, 2024

(54) BARREL INFLATABLE BELT

(71) Applicant: Robert Tremaine Whalen, Los Altos, CA (US)

(72) Inventor: Robert Tremaine Whalen, Los Altos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/850,471

(22) Filed: Jun. 27, 2022

(65) Prior Publication Data

US 2022/0323288 A1   Oct. 13, 2022

Related U.S. Application Data

(63) Continuation of application No. 16/833,383, filed on Mar. 27, 2020, now Pat. No. 11,395,662, which is a continuation of application No. 15/428,141, filed on Feb. 8, 2017, now abandoned.

(60) Provisional application No. 62/311,936, filed on Mar. 23, 2016, provisional application No. 62/293,536, filed on Feb. 10, 2016.

(51) Int. Cl.
| | | |
|---|---|---|
| *A61B 17/135* | (2006.01) | |
| *A61B 17/12* | (2006.01) | |
| *A61B 17/132* | (2006.01) | |
| *A61H 9/00* | (2006.01) | |
| *A61H 11/00* | (2006.01) | |
| *A41F 9/02* | (2006.01) | |

(52) U.S. Cl.
CPC ...... *A61B 17/135* (2013.01); *A61B 17/12009* (2013.01); *A61B 17/1204* (2013.01); *A61B 17/1322* (2013.01); *A61B 17/1355* (2013.01); *A61H 9/0092* (2013.01); *A61H 11/00* (2013.01); *A41D 2600/10* (2013.01); *A41F 9/02* (2013.01); *A61H 2201/169* (2013.01)

(58) Field of Classification Search
CPC .... A61H 9/009; A61H 9/0078; A61H 9/0092; A61H 9/005; A61H 2201/169; A61H 2201/0103; A61H 2201/1283; A61H 11/00; A61H 2011/005; A61B 17/132–1355; A63B 21/0085; A63B 21/4025; A63B 2225/63
See application file for complete search history.

(56) References Cited

U.S. PATENT DOCUMENTS

| | | | | |
|---|---|---|---|---|
| 4,149,540 | A * | 4/1979 | Hasslinger | A61B 17/1322 128/DIG. 15 |
| 5,451,234 | A * | 9/1995 | Wassermann | A61B 17/1327 606/203 |
| 5,795,312 | A * | 8/1998 | Dye | A61H 9/0078 128/DIG. 20 |
| 11,395,662 | B2 * | 7/2022 | Whalen | A61B 17/135 |
| 2002/0115950 | A1 * | 8/2002 | Domanski | A61F 5/0118 602/5 |
| 2006/0211976 | A1 * | 9/2006 | Ramsey | A61B 17/1322 602/75 |

(Continued)

*Primary Examiner* — Kathleen S Holwerda
(74) *Attorney, Agent, or Firm* — Snell & Wilmer L.L.P.

(57) ABSTRACT

An inflatable belt 100 for use in a BFR system with an outer belt material 102 hermetically sealed to an inner belt material 101 along a perimeter, thereby forming a plurality of inflatable chambers 103, with at least one cutout relief between at least two of the plurality of inflatable chambers.

16 Claims, 21 Drawing Sheets

(56) References Cited

U.S. PATENT DOCUMENTS

2015/0133991 A1\* 5/2015 Kosiorek ............ A61B 17/135
606/202

\* cited by examiner

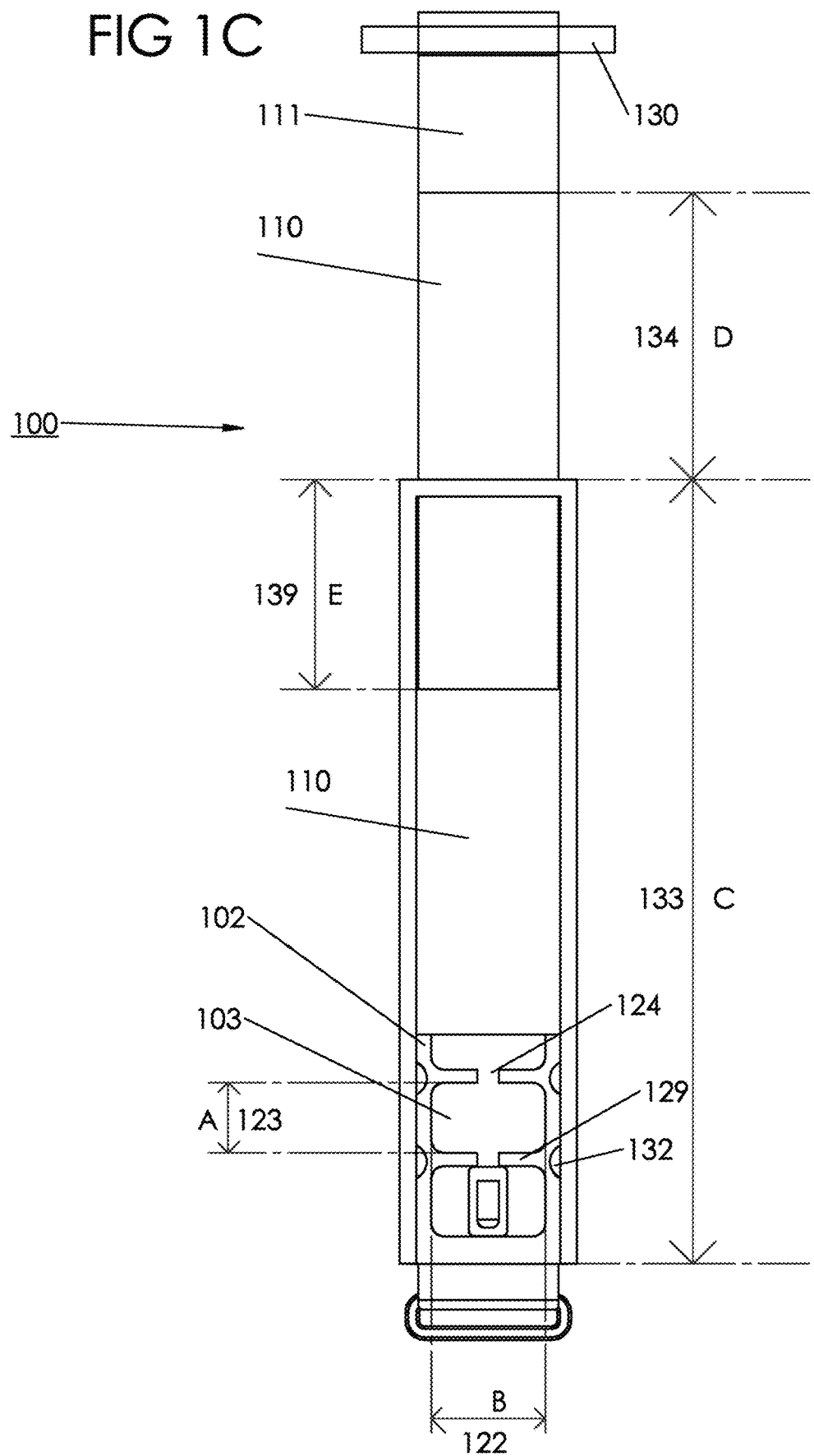

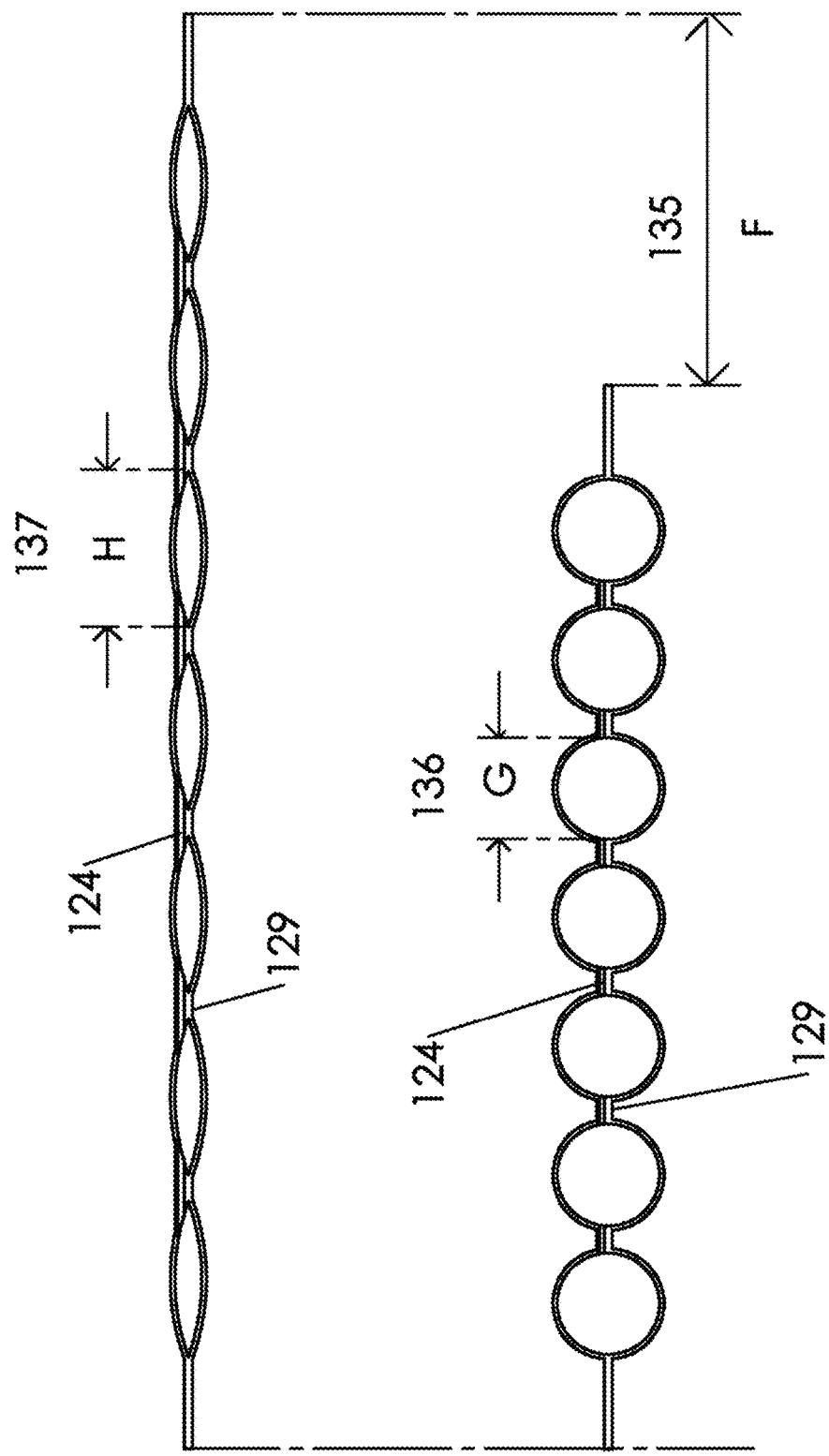

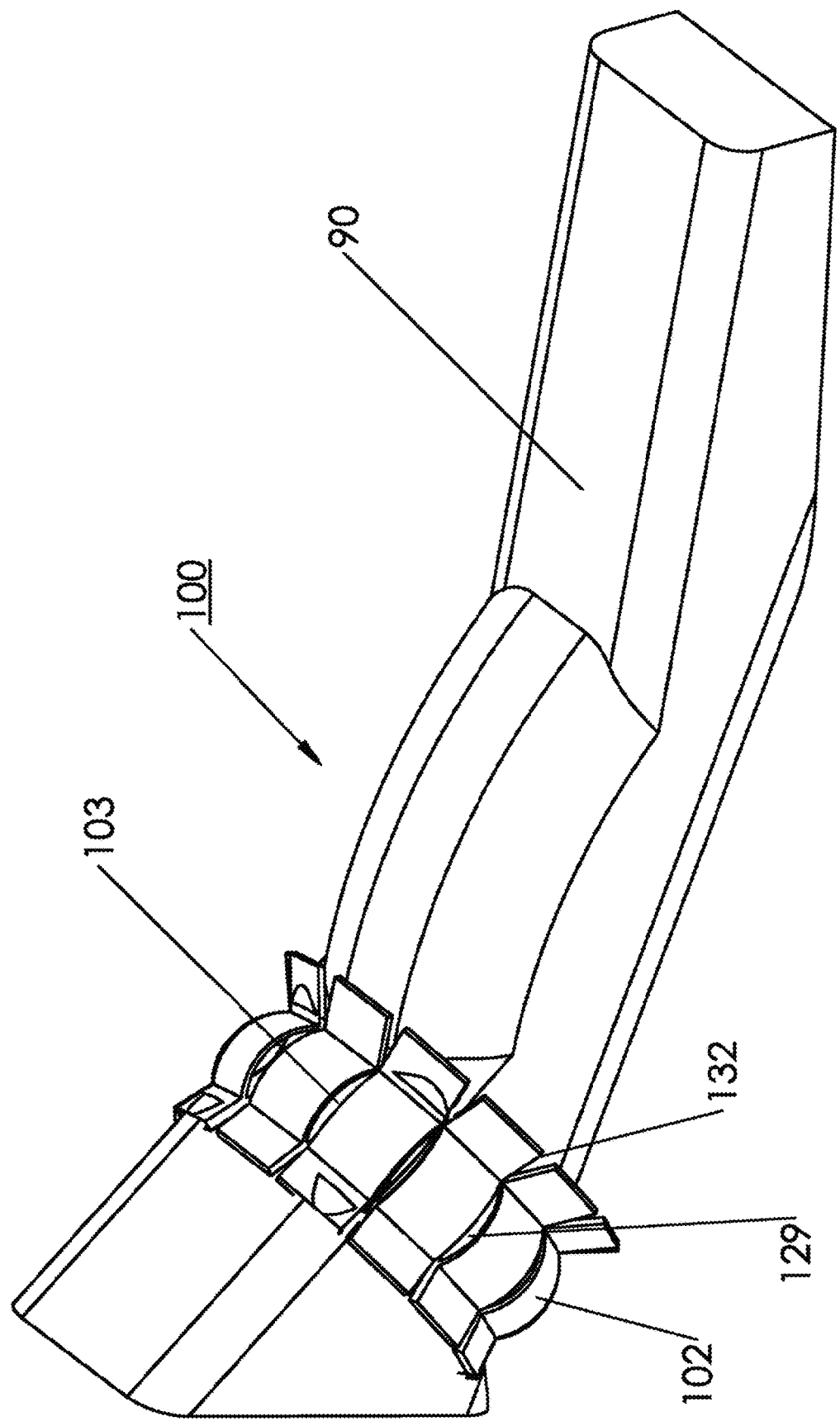

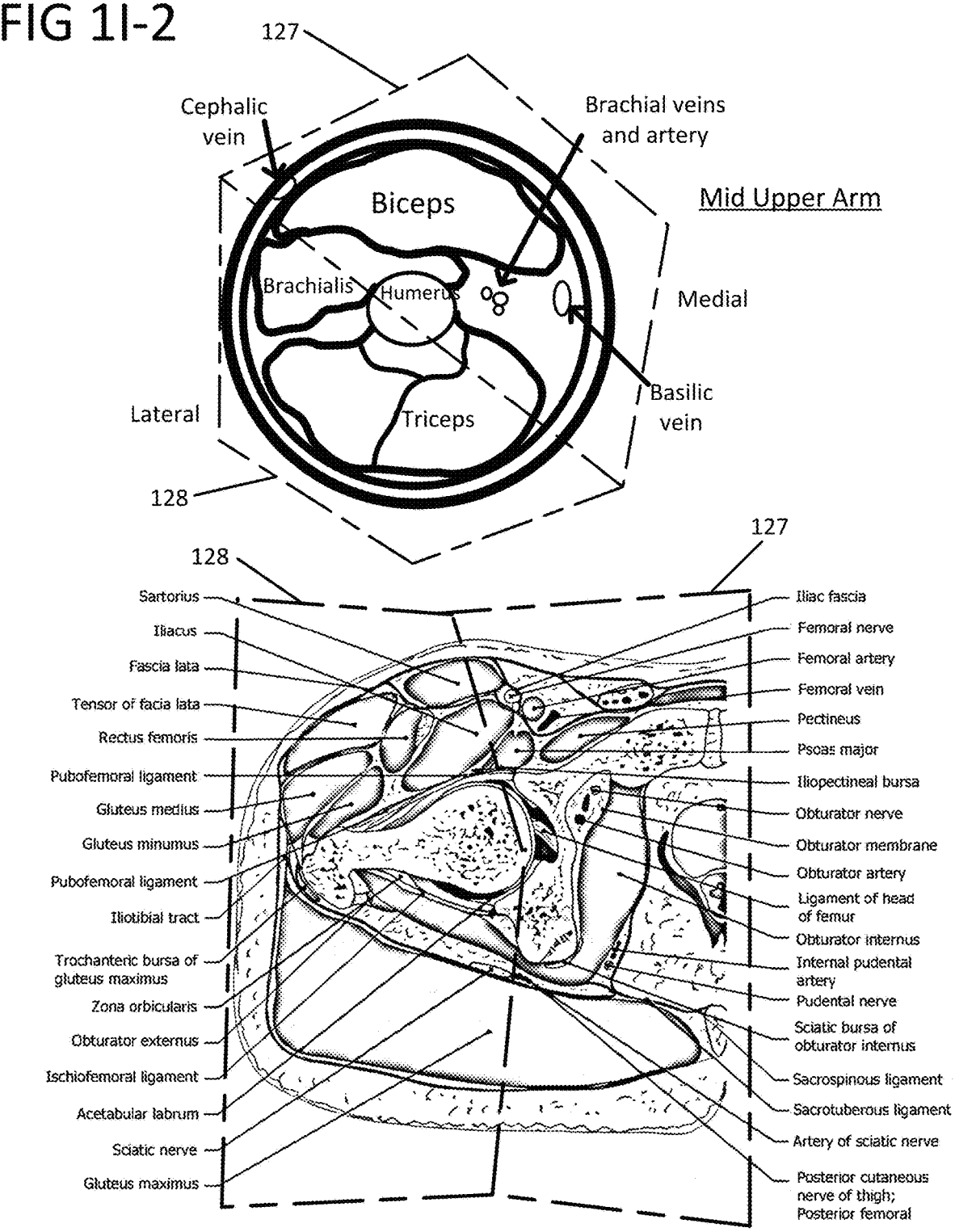

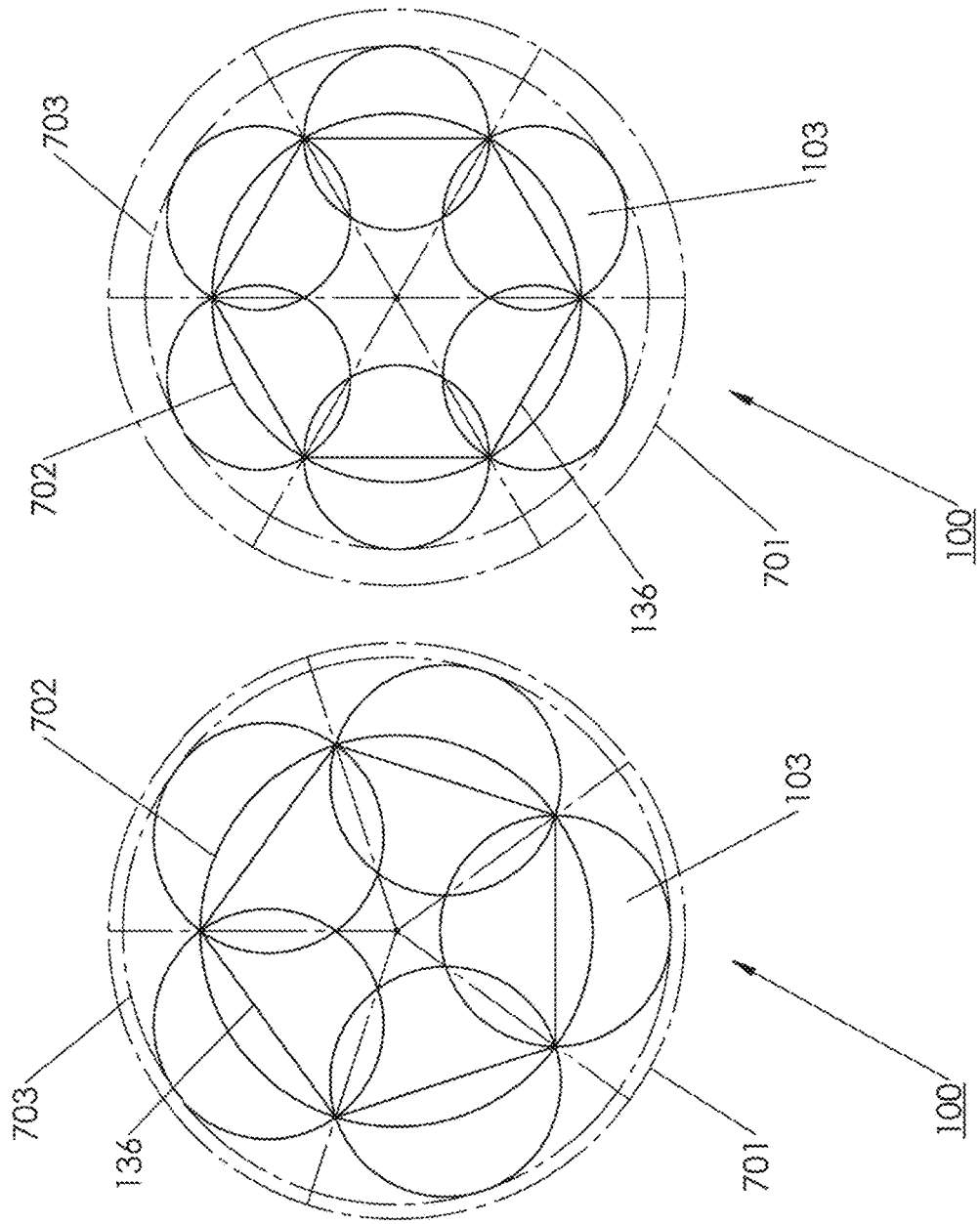

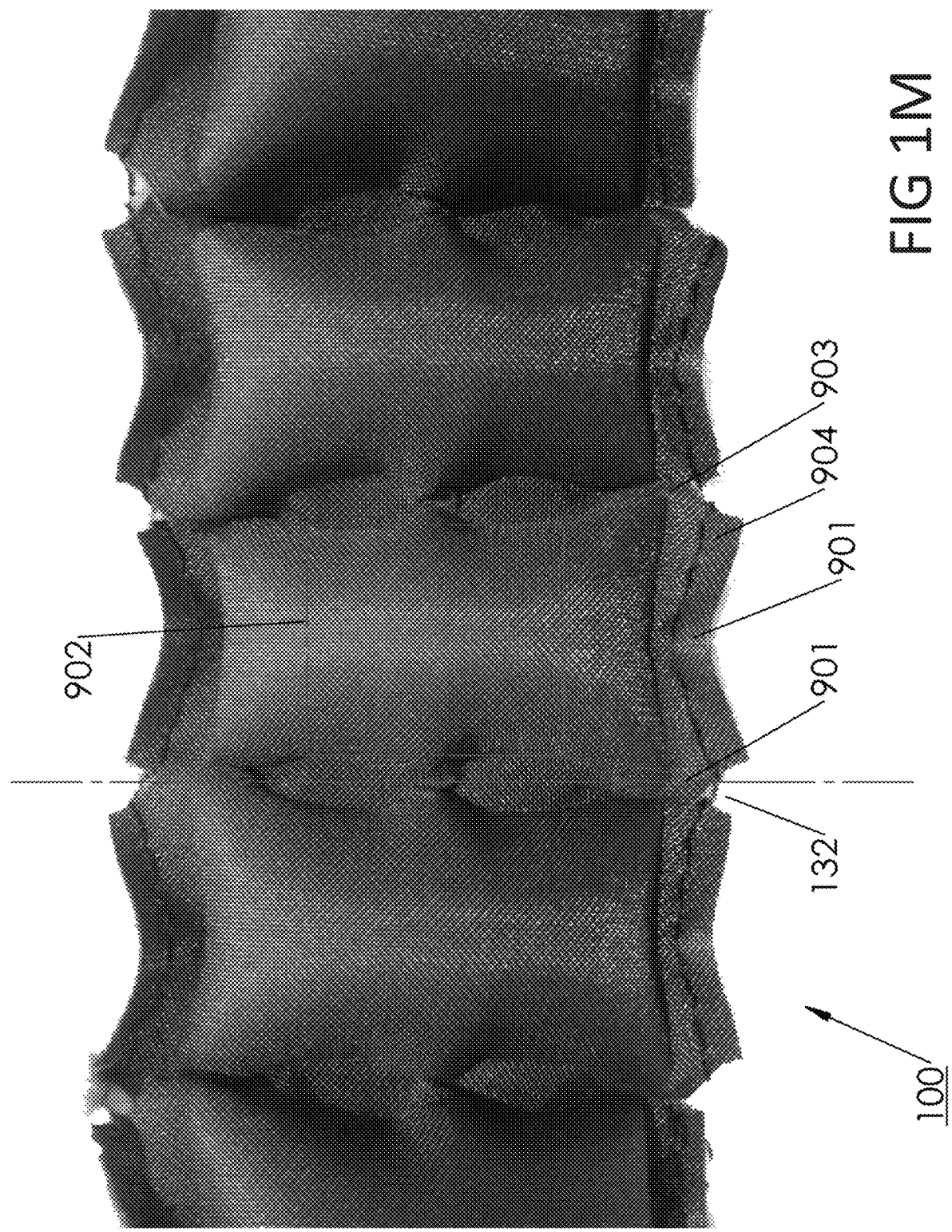

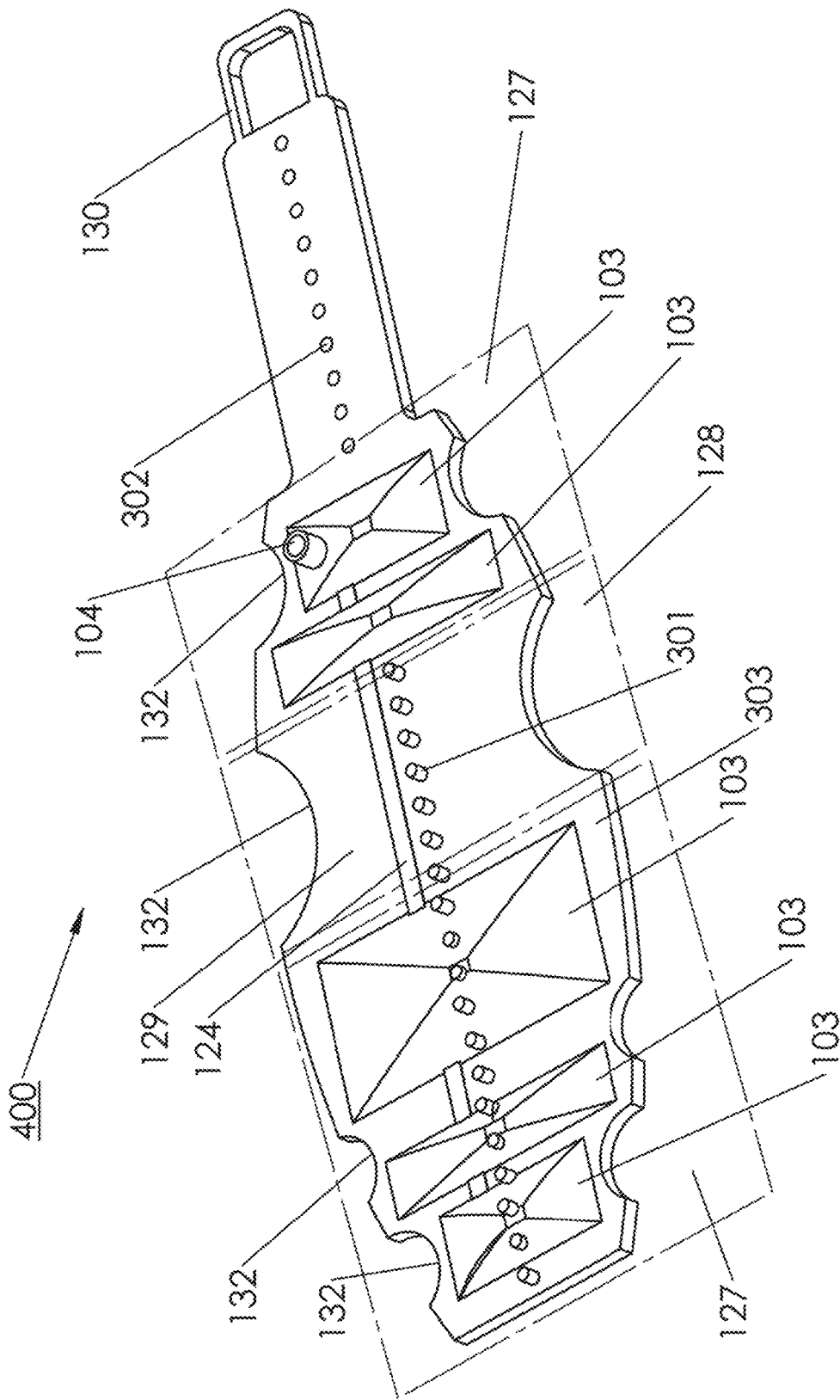

BARREL INFLATABLE BELT

CROSS-REFERENCE TO RELATED APPLICATIONS

This application is a continuation of U.S. Ser. No. 16/833,383 filed on Mar. 27, 2020 and entitled "Barrel Inflatable Belt." U.S. Ser. No. 16/833,383 is a continuation of U.S. Ser. No. 15/428,141 filed on Feb. 8, 2017 and entitled "Barrel Inflatable Belt." U.S. Ser. No. 15/428,141 claims priority to and the benefit of U.S. Provisional Application No. 62/293,536 filed on Feb. 10, 2016 and entitled "Blood Flow Restriction Belts and System," and U.S. Provisional Application No. 62/311,936 filed on Mar. 23, 2016 and entitled "Barrel Inflatable Belt." Each of the foregoing applications are hereby incorporated by reference.

FIELD OF THE INVENTION

This invention relates to blood flow restriction systems, and more specifically to an inflatable belt design for use therein, to provide a simple to manufacture, simple to use, comfortable, effective, and less expensive alternative to current designs and products in use.

BACKGROUND OF THE INVENTION

The muscle training apparatus, system, and method described in prior art, and herein in this application is spreading fast globally because of its beneficial effects as described below. In addition, national and foreign physicians as well as universities have conducted blood flow restriction research investigations, as a result of them, researchers have published many articles.

SUMMARY

In accordance with the present invention, an inflatable belt is provided for use in a blood flow restriction system, the inflatable belt comprising an outer belt material and an inner belt material, coupled together in such a manner as to create a plurality of inflatable chambers to be inflated with a gas, preferably air, and the configuration and shape of the chambers such that the circumference of the belt shrinks when the chambers inflate, compressing inward on a portion of a user's limb to provide compression on a target compression zone that in turn produces a restriction of blood flow in the venous system, and said compression level remains substantially constant during muscle contractions. The inflatable belt further comprises at least one cutout relief between at least two of the plurality of inflatable chambers. The inflatable belt may further comprise a body interfacing member that spreads the load applied to the limb, further reduces any possible pinching of the user's skin from kinking of the inner belt material, and provides sufficient friction to the user as a measure for preventing rotation of the inflatable belt should the user want to apply the inflatable belt to themselves. The applicant was unable to find prior inventions which utilize the applicant's invention of creating an inflatable belt that shrinks in length when inflated instead of expanding.

BRIEF DESCRIPTION OF THE DRAWINGS

FIG. 1C—shows the inflatable belt of FIG. 1A with dimensions marked on important features of chamber height, chamber width, inflated length, non-inflated length, and overlap length.

FIG. 1D—shows the inflatable portion of the belt of FIG. 1A in both a relaxed and inflated state to illustrate how the length shrinks under inflation.

FIG. 1G—shows an inflatable belt wrapped around a limb of a user in perspective view, and optional cutouts in the form of slits in the edge of the belt along the length to allow better shrinking and contouring on the limb.

FIG. 1I-2—shows a cross section of the arm and leg in the vicinity where the inflatable belt should be placed, and highlights the location of the veins in the arm and leg for targeting purposes.

FIG. 1I-3—shows an example of a non-rectangular gas bladder, designed for the legs, for optimizing the comfort for the user by only compressing a target compression zone, while simultaneously providing sufficient compression to achieved adequate BFR.

FIG. 1K—shows a geometric comparison between belts with differing amounts of chambers, and the effect of the chambers, and changing the quantity of chambers, on the outmost diameter when inflated.

FIG. 1M—shows a prototype inflatable belt, inflated to a closed position, and the effect of adding cutout reliefs to reduce the edge effects and improve the shrinking and elastic properties of the belt.

FIG. 4—shows an inflatable belt similar to FIG. 3A, with varying sizes of chambers to target and optimize compression to various target compression zones on a limb.

DETAILED DESCRIPTION

Figure 1A:
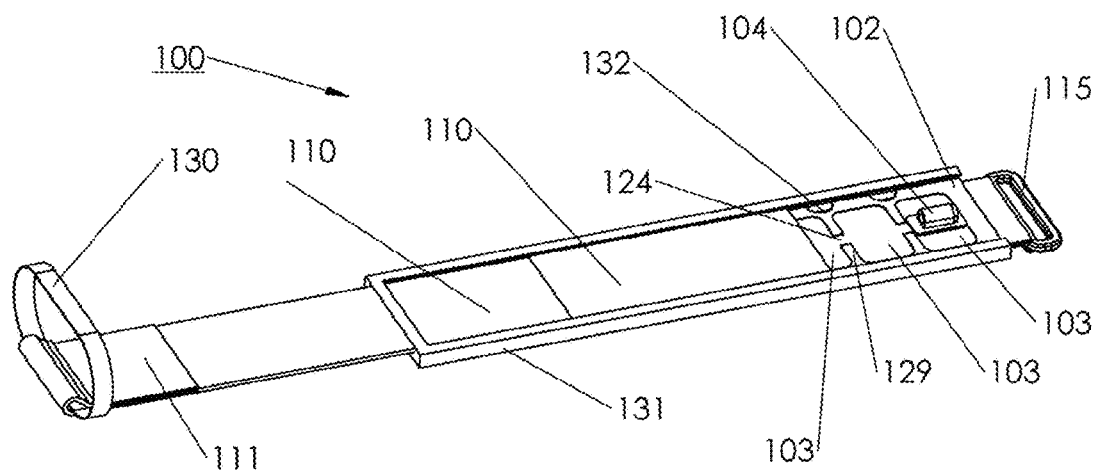
FIG. 1A—shows an inflatable belt that shrinks in length when inflated.

The muscle strength increasing method according to these patents is a distinctive non-conventional one that involves compression of an arm or leg at a position near the top thereof. This muscle strength increasing method (the subject muscle strength increasing method is herein referred to as a "Blood flow restriction muscle training method" or simply BFR).

Muscles are composed of slow-twitch muscle fibers and fast-twitch muscle fibers. Slow-twitch muscle fibers are limited in their potential for growth. Accordingly, it is necessary to the recruit fast-twitch muscle fibers in the muscle in order to develop the muscles. Recruitment of fast-twitch muscle fibers causes lactic acid buildup in the muscles, which triggers secretion of growth hormone from the pituitary. The growth hormone has effects of, for example, promoting muscle growth and shedding body fat. This means that recruitment and exhaustion of fast-twitch muscle fibers results in development of fast-twitch muscle fibers and, in turn, the entire muscle.

Slow-twitch muscle fibers and fast-twitch muscle fibers are different from each other in terms of the following. Slow-twitch muscle fibers use oxygen for energy and are recruited for low-intensity endurance activities. Fast-twitch muscle fibers provide for activities regardless of whether or not oxygen is present. They are recruited after the slow-twitch muscle fibers for highly intense activities. Therefore, it is necessary to cause the earlier recruited and activated slow-twitch muscle fibers to be exhausted soon in order to recruit fast-twitch muscle fibers.

Conventional muscle strength increasing methods use heavy load with, for example, a barbell to cause the slow-twitch muscle fibers to be exhausted first, and then to recruit the fast-twitch muscle fibers. This recruitment of fast-twitch muscle fibers requires a significant amount of force generation from the muscle, is time-consuming, and tends to increase the burden on muscles and joints.

On the other hand, muscle exercise may be performed under the restriction of muscle blood flow into the limb distal to a predetermined position by means of applying pressure upon the muscles at the predetermined position near the top of the limb. Since less oxygen is supplied to these muscles, the slow-twitch muscle fibers, which require oxygen for energy, are thus exhausted in a short period of time. Muscle exercises with blood-flow restriction by application of pressure will result in recruitment of the fast-twitch muscle fibers without needing a large amount of exercises. More specifically, when pressure is applied circumferentially upon a limb at a predetermined position near the top of the limb, venous circulation is restricted while arterial circulation is kept almost the same as the normal condition if an appropriate pressure is applied. This is because veins are closer to the skin surface of the limb, and are thinner and less muscular (less resistant against a force for pressurization) than arteries while arteries are found deep within the limb, and are thicker and more muscular than veins. By holding that condition for a certain period of time, the limb that has compressed near the top thereof becomes engorged with blood which runs from arteries but cannot flow through veins. This promotes a state of blood pooling in the capillaries where such an amount of blood is not flowing normally. The limb that is compressed at a position near the top thereof gets into a state as if it were doing heavy exercises. During this time, because of the temporal occlusion of the veins, the muscle fatigue is caused by the fact that the lactic acid that has built up in the muscles is less likely to be removed from the muscles. Furthermore, the brain receives information of strenuous exercise from muscles, and brain's physiological action is then responsible for the production of much more growth hormone than is usually produced during the daily life for muscle regeneration as well as during typical exercises.

In other words, BFR training contributes to artificially produce a state which otherwise will occur during and after heavy exercises. It is possible to cause muscle fatigue much more heavily than would be produced normally with that amount of exercises. In addition, the user can "trick" the brain into secreting a larger amount of growth hormone.

Because of the aforementioned mechanism, restriction of muscle blood flow can allow users to significantly develop their muscles.

BFR training method is premised on the theoretical concept of the muscle strength increase by the restriction of blood flow. More specifically, the BFR training method involves the application of an appropriate force for pressurization to at least one of the limbs at a predetermined position near the top thereof to restrict the blood flow restriction into the limb distal to that position. The force for pressurization serves to put an appropriate stress attributed to blood flow decrease on the muscles. Thus, the muscles can be developed in an effective manner.

The BFR training method may feature a specific modality for muscle development without any exercises because it involves developing muscles by putting a stress attributed to blood flow decrease on the muscles. With this feature, the BFR training method is highly effective for the recovery of motor ability in people with impaired motor function, e.g., the elders or an injured person.

In addition, the BFR training method can compensate for a total amount of stress that is placed on the muscles by putting on the muscles a stress attributed to blood flow decrease. When combined with some exercises, the method advantageously reduces an exercise-related load as compared with conventional methods. This feature produces effects of reducing possible risks of joint- or muscle-damages and shortening a necessary time period for training, because it can decrease the amount of muscle exercises for the muscle development.

It should be noted that, for the implementation of the BFR training method, such a device or apparatus is essential that can restrict the blood flow through the muscles that are subject to be developed and that can precisely adjust and maintain the degree of blood flow restriction.

While previously filed applications describe the concepts involved in BFR training, they do not address in any detail the anatomy of the human extremity circulation, nor do they describe the manner in which venous and potentially arterial blood flow are restricted or modulated when the tightening tool is applied. For example, In U.S. Pat. No. 8,328,693 Sato discusses the need for normal arterial flow for safety reasons, but neglects to discuss the mechanism of local tissue deformation that leads to venous flow restriction with implementation of the described tightening device.

As the applicant will describe, the details of the anatomy determine the effectiveness of specific tightening tool designs, and can significantly impact the comfort for the user. Specifically, the applicant will disclose designs that may target a portion of the limb circumference direct application of pressure by targeting only a portion of the circumference for direct application of pressure. The overall discomfort and feeling of constriction are reduced, yet sufficient venous restriction is obtained by this concept.

Arteries may run deep in the body, but veins are both superficial, on the limb surface, and deep in the deep venous system. When the tightening tool, or hereinafter referred to as "belt", "band", "inflatable belt", "inflatable band" etc., is placed on the body, a certain amount of tissue is compressed inward (minimal amounts of tissue squish out the sides). Superficial veins are temporarily partially or fully occluded, depending on the level of compression, and tissue is pushed radially inward. Tissue is incompressible relative to the capillary, venous, and arterial systems, and thus, the compliance in the system is primarily the partial or total collapse of these vascular compartments, and secondarily the shift of extracellular fluid away from the zone of pressure.

This explanation is neglected in previous patent applications, leading one to surmise that the inventors did not fully understand what was happening inside the targeted limb regarding tissue displacement and fluid shifts. As will be disclosed, what is essential in the end then, is only to cause enough displacement in the correct areas on the human body, i.e. where veins are present superficially or in the deep system, as to achieve the required level of BFR. As an example, the human anatomy is such that the deep veins may be compressed by applying pressure, to displace tissue inwards on the underside of the arm, and the inside, or groin area of the leg. While all previously disclosed bands in Sato and U.S. Pat. No. 8,273,114 to Wasowski have been of rectangular and uniform shape and construction, these rub over various muscle groups (biceps, hip flexor, etc.) causing discomfort, cramping, and pain, when in reality these areas do not have any veins under them and do not require direct, site-specific, heavy compression. Therefore bladder size, and shape overall of the band, can be optimized to reduce compression in certain places that undergo rubbing over a muscle during movement, the band thinned out over these areas, as will be disclosed below.

Understanding the full physiology and anatomy therefore is critical to designing a system that is comfortable, easy to use, and most economical to produce.

Various patent applications by two inventors, Sato and Wasowski, have been issued on the devices, apparatus, and methods used to implement BFR training, and various other methods have been published in research papers as discussed. It will be shown how there are yet many improvements to be made both on the apparatus, system and method of application to promote widespread adoption, in the areas of cost effectiveness, comfort, and ease of use. Both inventors describe in their applications the importance of reducing the cost of the system (Sato U.S. Pat. No. 8,992,397), improving the comfort level (Wasowski U.S. Pat. No. 8,273, 114), and making the system easy and safe to use, together with an instructor or by oneself (Sato U.S. Pat. No. 8,992, 397), as the principal barriers to mass adoption, and it is the aim of the applicant to solve these deficiencies in existing products and disclosed embodiments.

Additionally, various tourniquet cuff designs or blood pressure cuffs have been described in prior art that describe the full encircling of the limb, with pneumatic cuffs of fixed outer circumference and radially inward expansion for the purposes of completely stopping blood flow in the limb. These cuffs require the full encirclement of the limb in order to guarantee complete shutoff of the blood flow supply as the purpose of those inventions is surgical in nature and completely different than with BFR exercise. These cuff designs also employ outer stiffeners, stiffening members, or constructions that serve the same function as a stiffener, for fixing the outermost circumference and directing the expansion of the pneumatic bladder inwards. These devices specifically seek an inability of the cuff to lengthen and shorten when wrapped around a limb, or therein have an elastic property, because this feature works against the occlusive properties of the belt as the applicant has demonstrated during testing. Again, the purpose of occlusive tourniquet constructions is to shut off, or occlude blood flow in a limb, whereas BFR, and the applicant in particular, seeks only to temporarily restrict the flow of blood in the limb, and therefore mitigate against the medical complications and safety hazards associated with occlusion of blood flow in the limb. The differences in application between tourniquet cuffs and BFR belts are further evidenced by the repeated suggestion by authors of prior art occlusive tourniquet cuffs that their goal is to minimize the pressures applied in order to minimize underlying tissue damage, and they therefore generally seek to use wider cuffs, which require lower pressures to occlude. Using lower pressures, and in particular wider cuffs, has several detrimental effects for BFR training. First, the margin of error in finding the right pressure for a BFR session is extremely tight, and requires a sophisticated and expensive device, such as a Personal Tourniquet System (PTS) from Delfi Medical which cost about $5000 at the time of this application, to target this pressure exactly. Another negative is that wide occlusive cuffs cover the muscle and prevent expansion of the muscle during a contraction, leading to a painful experience by the user. Finally, wide cuffs, particularly if used by an inexperienced user, can easily occlude blood flow at just over systolic pressures and therefore put the user in a dangerous situation; or, alternatively an expensive device and experienced supervision is required to operate the BFR system. By contrast, the applicant has tested prototypes made with the disclosed invention herein and shown blood flow from muscle contraction is still present up to 500 mmHg, which is a multiple of systolic blood pressure vs. a fraction of it in the case of Delfi's PTS device. The benefit to this is a) it is near impossible for the individual to occlude and get in a dangerous situation so the individual requires minimal training and can do it themselves and b) there is a much wider range of pressures for which an effective BFR pressure can be found meaning both the user and the equipment do not need to be precise/sophisticated, and therefore expensive. For example, the applicant was able to achieve effective restriction at pressures of 190 mm Hg up to 250 mmHg on the arms, meaning a spread of 60 mmHg, was reasonable as a margin of error on an effective BFR pressure. If the optimal pressure was 220 mmHg this would correlate to an acceptable error of +/−30 mmHg which is easily achieved by inexpensive, commercially available palm aneroid sphygmomanometers which cost under $100 vs. $5000 in the case of the PTS device. By contrast, this level of inaccuracy would be unacceptable in the case of a wider cuff because an extra 30 mmHg would likely be the difference between restriction and occlusion, which would put the user in danger. Additionally, because occlusive tourniquet cuffs are designed to occlude, they must constantly be tethered to the measuring/monitoring devices to ensure patient safety. This tethering introduces another detriment in the context of BFR, in that exercise selection must be limited to exercises which can be done in proximity of a power outlet and within the range of the tether. Therefore few to no sport specific movements can be practiced, and the device is not really suitable as a training tool as compared to the applicant's invention. By using the inventions disclosed herein, the applicant therefore has been able to create a system that is inherently safe, does not require precise instruments and measuring equipment, allows for the use of inexpensive inflation devices and gauges for setting of the appropriate pressures, and provides freedom to the user to practice BFR wherever they choose and perform whatever exercises they choose.

U.S. Pat. No. 8,273,114

U.S. Pat. No. 8,273,114 to Wasowski describes a full body suit with the addition of cooling, electrical grounding, and a variety of other features. Wasowski's invention appears to be a variation of Sato's designs, but is significantly more costly and difficult to use. Further Wasowski does not go into any further detail on the blood flow restriction means other than to say they are like ordinary blood pressure cuffs. Ordinary blood pressure cuffs are inelastic and cover a substantial length of the limb, encompassing the bulk of the muscle that is to be expanded during contraction and exercise. In practice, a very wide cuff around the full circumference, as described by Wasowski, is extremely uncomfortable and even painful because the muscle has no room to expand when contracted and the cuff squeezes blood from the muscle making it ischemic. Wasowski therefore fails to contemplate a simple, cheap, affordable, safe, easy to use design for bands or belts for performing BFR training as will be described by the applicant.

U.S. Pat. No. 6,149,618

To the best of the applicant's knowledge, U.S. Pat. No. 6,149,618 to Sato is the original application on the subject of BFR and describes a simple, non-inflatable band concept and generic method of using the band to perform BFR training, or KAATSU Training™ method. Sato describes a simple band, or rope, made of elastic material, for wrapping around the body as a tightening tool, as well as a band or belt made of inelastic material with spring inserted and means to tell what tension is applied. It appears, Sato had not yet conceived of the method of using air pressure when coming up with this concept and thus there are no features in the design related to making an air-bladder based system function comfortably, effectively, and cheap to make. Sato correctly notes the importance of the tightening tool having some elastic property and some method of knowing what the compression force is that is applied to the body. While Sato discloses a liner for the belt, Sato only recognizes the importance to protect the user's skin from abrasion. However, because Sato has been assuming a narrow compression area from the belt width, Sato fails to note the need for a load spreading mechanism or similar feature of the design, which greatly improves the comfort of a pneumatic system and simultaneously avoids pinching of the skin. In Sato's designs for non-pneumatic belts, due to Poisson's ratio, under tension his belts will shrink in width and become more like a wire, causing additional discomfort on the limb as the belt is stretched. Sato, in U.S. Pat. No. 8,992,397, notes the economical nature of a non-pneumatic construction, and the importance thereof, however Sato's following patents are all utilizing a pneumatic adjustment, as is the KAATSU equipment currently on the market, and thus Sato has acknowledged the superiority of such a system from an adjustability, precision, safety, and efficacy standpoint. This is likely because such a construction, as described in U.S. Pat. No. 6,149,618, would be cumbersome for a user to try to adjust. It is tougher and more tedious to make small adjustments in the locked circumference compared to first locking a circumference and then adding small amounts of air pressure. Further, differences in friction along the surface of the limb lead to uneven tensioning and tightening with a non-pneumatic system. Sato, and Wasowski correctly recognize the superiority of a pneumatic system.

Further, Sato does not address the need to provide a means for users to rapidly tension the belt in a simple and cost-effective way. Using a scale as depicted is imprecise because the spring constants have to be relatively high in order to provide enough compression on the muscles. The flip side of this is that small inaccuracies in measurement from the user result in large differences in compression and may lead to unsafe conditions. Additionally, Sato's preferred fastening method is the hook and loop fastener, so just trying to apply the tightening tool initially will be cumbersome as the hook and loop fastener will tend to catch and make precise placement of the hook and loop fastener very difficult. This problem is further exacerbated by the situation when the hook and loop fastener must be connected behind one's arm because the user can't see that location and is "feeling in the dark". All in all, Sato's system for applying belt tension is costly, imprecise, and cumbersome from an ease-of-use standpoint. This is evident further by the fact that Sato has completely moved away from such systems to pneumatic systems in commercialization.

U.S. Pat. No. 7,413,527

Sato then advanced to U.S. Pat. No. 7,413,527, in which he improved upon the simplistic band design with an inflatable belt design. Sato also mentions another deficiency of U.S. Pat. No. 6,149,618, which is that Sato's design in U.S. Pat. No. 6,149,618 rotates around the limb when a user attempts to tighten it by themselves. This is a problem with U.S. Pat. No. 6,149,618 because for that device to function, significant compression to the skin must be applied by the band at the outset, to achieve the required levels of compression. This rotation therefore renders the design very difficult to use by an individual, further limiting adoption as stated by Sato in later applications. However, Sato's solution in U.S. Pat. No. 7,413,527 is to add multiple additional belt members which further complicates the sewing process, adds materials, bulk, and cost to the system. The applicant will disclose how adding frictional features to the belt to adhere to the user's limb or clothing, in addition to removing the need to apply high initial tension to the belt, will ameliorate the problem of rotation of the band style in U.S. Pat. No. 6,149,618. Sato aimed to resolve the problem of lack of precision and easy adjustment by creating a tube that slips inside a hollow bag, the bag formed by sewing two pieces of fabric together, both of which are elastic. Sato further describes the tube being replaceable and a clip being used to fold over and limit the length of the inflatable tube. However, such suggested construction of stuffing a tube into a hollow bag for each application or each individual user is impractical and a barrier to ease of use, where Sato has described himself that ease of use of the band is a critical factor toward the utility of BFR. Sato further discusses the added need for the clip such as in order to eliminate a gap between the muscles at the overlap point for the purpose of providing full circumference compression. This stated requirement for full circumferential compression further shows that Sato does not fully appreciate what is happening inside the limb and where it is important to apply pressure, and why this clip and limiter plate features are not necessary. Sato further discusses a deficiency in the design such that a limiting piece, such as a plate, or wire, is necessary to prevent expansion of the tube in the radially outward direction, similar to the action of a tire in preventing radial expansion of the compliant inner tube. Sato specifically states that the main belt has a predetermined elasticity, as do current KAATSU products. A belt made with elastic materials has the benefit of expanding slightly during muscle contraction, but requires the inclusion of the limiter plate to prevent radially outward expansion, and thus adds parts, complexity, and cost into the design. Sato describes modifying the construction of the tube itself so that it may inflate more toward the inside than the outside, however Sato is still stuck on the idea that there is a main band around the tube, and that all components, and the tube as specifically stated, are elastic, further necessitating a limiter plate. Sato describes two strip shaped elastic bodies having different spring rates, but by virtue of them both being elastic, there will be radially outward expansion and thus, a requirement for additional limiting plate hardware to force the expansion toward the limb to maintain required compression.

Sato never addresses the need to determine the initial tension of the inflatable belt, and its corresponding initial compression of the limb, and further does not discuss the by-product of higher initial limb tissue compressions as a detriment to the comfort of Sato's designs. High initial tissue compression results always in some degree of blood flow restriction and with concomitant buildup of metabolites and lactic acid even at rest. Without sufficient venous return blood flow to remove these metabolic byproducts, the limb may become uncomfortable with a pain not easily tolerated by many people.

In failing to address the initial compression guidelines, or design elements, Sato further shows he has not thought to optimize the inflation scheme as it relates to comfort of the user. As described above, a tight band is uncomfortable. Furthermore, without a large air cushion separating the muscle from the outer stiff band of the KAATSU belt, when the muscle contracts during an exercise, the muscle comes in direct contact with the outer band. This puts a higher localized stress on the muscle and can lead to pain and cramping. The user may choose to discontinue BFR Training. The applicant has witnessed such effects first hand with current KAATSU equipment where this local or point compressive loading and rubbing create the sensation that the hip flexor muscle was hit with a hard object. It is an aim of the applicant to solve this problem by spacing the inflatable bladder off the limb by a sufficient amount that it may inflate inward to form a larger air cushion than that of Sato's designs, further assisted by a body interfacing component that spreads the load on the limb.

Further still, all of Sato's designs contemplate a single rectangular tube cross-sectional shape with the long side of the tube parallel to the length of the belt. Such a design, under inflation, tries to expand outward while distorting the rectangular cross-sectional shape, hence Sato's requirement for limiter plates to restrain outward expansion of the tube and help maintain the desired rectangular shape. The limiter plates are not entirely successful. The shape of the tube turns into a hot dog, which, when bent to conform to the limb circumference, kinks and may pinch the skin, so the kinks further provide less compression to that region of the body. Whereas the shape of Sato's tube in all of Sato's designs dictates that the tube will expand outward like an inner tube, the applicant's invention actually shrinks in length when inflated. The shrinkage, in combination with the inflation of the chambers, form two modes of compression on the body. Further, because the belt shrinks when inflated, there is no need for limiter plates or other fancy features to provide adequate compression on the body.

Overall, Sato fails to recognize that the construction of the band has unnecessary components in it, and that sufficient, radially inward, more comfortable, and easier to apply, compression can be achieved with proper construction techniques and selection of materials as will be disclosed by the present inventor. By stating that economics are important, yet including unnecessary components in the main band construction in this application and in now-current product sales, Sato unnecessarily complicates the design, driving up manufacturing costs, and increasing the price to the end customer, and shows that he has not contemplated a simpler more efficient design like that disclosed by the application.
U.S. Pat. No. 7,455,630

Sato then moved to U.S. Pat. No. 7,455,630 wherein Sato depicts a simplified BFR system consisting of a manual analog valve readout, and manual squeeze ball inflation means. However, rather than expanding on a full system that would be cheap and effective to implement, Sato continues to invent around methods of directing the inflation toward the user's limb with complicated limiting plate designs. Sato seems to have come to the conclusion that the limiting plate is a key feature, (as it currently exists in the product as well), and is therefore focusing on adding components to the design, rather than rethinking the design to eliminate parts and make the construction more efficient, yet just as effective, as the current inventor has conceived. Sato further discusses the need to provide uniform compression around the entire limb with a complicated limiter plate design that bends and contours. However the limiter plate is not in contact with the skin, the air bladder is, and the air pressure in the bladder is uniform therefore the compression will be the same in all places where the bladder is in solid contact with the skin. Kinking, which is inevitable when bending a straight tube as discussed above, further results in not only pinching of the skin, but also lower pressure points around the kinking area. This is yet another confirmation that Sato does not fully understand the physics of what is happening with the band, and what is needed to achieve the proper level of venous restriction. As stated above, but restated here, the applicant's invention of a spacing method to space the air bladder (or gas bladder) off the limb, thereby provides a large inflation volume, which has the significant effect of improving comfort. Part of this is evidenced by applying a KAATSU band and the belt of the applicant's invention on the same location and measuring the air pressure spikes when performing a muscle contraction. In the KAATSU belt, placed around the quadriceps, the pressure in the belt rose from initially 350 to 420 mm Hg. In the applicant's belt design the pressure rose from initially 350 to a maximum of 380 mm Ha. This reduction in spikes in air/gas pressure during muscle contraction, means that the muscle is seeing less compressive force from the belt overall, and therefore not getting cyclic "pounding" during movement on each contraction from the applicant's band as it is with the KAATSU band. In experiments, the KAATSU bands became too painful during a dynamic training session, causing a bruising or cramping sensation that the subject had to discontinue the training, whereas the subject could complete a BFR training session, achieving muscle "failure", with the applicant's invention. Sato further does not describe any elastic aspect of the limiter plate, in fact he contemplates it as inelastic. Thus because the limiter plate is coupled to the main belt, and encompasses the limb, the main belt will be prevented from expanding under muscle contraction, further exacerbating the pressure and pain on the muscle and causing higher pressure spikes in the band under muscle contraction. All in all, U.S. Pat. No. 7,455,630 to Sato has the same deficiencies as U.S. Pat. No. 7,413,527, and further reinforces that Sato never contemplated the simplifying elements of the applicant's invention.

U.S. Pat. Nos. 8,021,283 & 8,328,693

Realizing the difficulty in facilitating widespread adoption based on significant expertise and knowledge of the body, Sato further continued to invent along the lines of automation and sensing to make KAATSU Training safe for any person. U.S. Pat. Nos. 8,021,283 and 8,328,693 to Sato principally focus on these automation aspects, assuming band designs as discussed prior. In fact, Sato even discusses the inadequacy of just measuring bladder air pressure at the beginning of a training session because of physiological changes during the workout, for example the increase in limb circumference from doing work during KAATSU Training, and Sato's belt designs inadequacy of dealing with these expansions to keep a more constant air pressure inside. Sato further reinforces the need for accurate, more constant air pressure control throughout a training session, so it is significant that Sato's band designs result in high pressure spikes during muscle contraction compared with the applicant's invention. Sato does not even address the ability of the band design itself to maintain more-constant air pressure, presumably because Sato does not recognize the significance of improving upon such feature, and the ramifications thereof in relation to comfort for the user. Whereas the applicant's invention is optimized to maintain air pressure by achieving a larger air volume than Sato's designs for a given desired radial compression on the skin, Sato's bands inflate with relatively little air as the inflatable portion rests directly against the skin to begin with, and therefore less volume into which the bands can expand before compressing the limb. Because there is less air, any increase in limb circumference with muscle contraction will proportionally correlate to a larger percent of displaced volume in the gas bag. This large percent displacement in the volume of air inside the bladder causes a high pressure spike, and overly large percentage increase in pressure over time during a KAATSU Training session, which further restricts flow, potentially beyond a safe level. The applicant's invention, which allows for a large air volume, act as an accumulator. Increases in limb circumference during training have less of an effect on the increase in band air pressure because the displacement represents a smaller proportion compared to the total volume of air in the bands. Sato, in discussing the safety aspects and need to avoid a situation where full occlusion of the venous system is achieved, fails to recognize that his system may start a session in a safe zone, but then, as the limb engorges in blood and expands, the level of restriction may become unsafe because the pressure in the bands has risen significantly. Sato describes a disconnect option, as do current KAATSU products, and thus by disconnection from the control equipment, a user is potentially given a false sense of security that they are still safe when disconnected from the monitoring and adjustment equipment. This all goes to point out that the design of the bands is critical, and a design which minimizes pressure increases during a training session, as disclosed by the applicant, is a safer inherent design. One final note is that while Sato argues for a fully automated system, the applicant argues for a hybrid system with a manual inflation means and automated pressure control. The significance is that if there is a problem, the safety procedure is always to reduce pressure and restore normal conditions, which both Sato and the applicant agree on. However in Sato's automated system, the machine can potentially continue to work and prolong the unsafe condition, whereas a re-inflation action is required to be performed by a human in the applicant's system, and the human can assess many more variables in the situation better than Sato's machine, in deciding whether to continue or not.

Relating to bands, Sato does disclose another configuration of a gas bladder, or bag, plus belt combination by stating the gas bag may be on or in the belt. Prior, the gas bag is only described as being in the belt. However, Sato does not go into detail on how exactly this works, and it is left to believe that the gas bladder is a separate item that is permanently attached to the belt, and thus still incorporating more components, and manufacturing processes than the applicant's invention. Sato further fails to describe a "doubling back" band (in relation to inflatable bands), such as disclosed in U.S. Pat. No. 6,149,618, further confirming that Sato has discarded such design as non-preferable and too difficult to use by the user because of the rotational issues, which the applicant has solved. Sato further states the importance of being able to utilize the system for longer periods of time, saying that the technique of restricting blood flow is improved with longer durations. Therefore, this further reinforces the importance of band comfort during training, and the value of the applicant's invention in improving comfort such that a user may sustain restricted flow for a longer period than with KAATSU equipment, because the comfort level is better. Sato further describes the belt as being elastic, neoprene rubber, which, as Sato has previously stated, requires a limiting plate in order to provide sufficient restriction. Thus, Sato's designs have not significantly changed from prior applications, and still remain expensive to build and cumbersome to use.

U.S. Pat. No. 8,992,397

In U.S. Pat. No. 8,992,397 to Sato, Sato comes back to the band design as a critical element to improve and reiterates, and further reveals, significant shortcomings of his previous inventions. Sato recognizes the superiority of a pneumatic system in improving the safety and pressure adjustment capabilities during setup and in the middle of a training session, but acknowledges the complexity in the design as a detriment to a pneumatic system versus a simple elastic band. Sato fails to recognize a design that is both simple and inexpensive to construct, and incorporates, and improves, the benefits of using pneumatics to apply pressure to the user. Sato describes two band structures, a straight type, and an overlap type, and how overlap types have a significant drawback of rotating on the user's arm when trying to apply initial tension. Because of Sato's band design, and the lack of a means to stand the band off the skin surface, the initial tension of a substantial degree is required to provide enough starting compression to obtain a sufficient overall compression level on the limb. In addition to solving the rotational problem, the applicant's invention does not require strong initial tension to achieve the required limb compression for most individuals, and therefore eliminates the rotational issues, while maintaining a simple construction. Sato further describes an overlap type of having a detriment that the ring employed, may cover a muscle region during rotation and cause discomfort to the user, thereby further acknowledging the critical nature of user comfort in the application. Because the applicant's design does not require significant initial tension, the displacement of the ring is not a problem. Further, the band may additionally be adjusted circumferentially after the fact as needed. Further still, Sato describes the gas bag as being divided into two chambers by the ring, and the pressures in the band not be controllable, however Sato therein, assumes that the circumference of the inflatable bladder must be longer than the limb circumference, causing the bladder to move through and wrap around the ring. In the applicant's invention, and as described prior relating to understanding the physics of what is happening in the limb, the bladder does not need to be the full length of the limb. Additionally, failing to state that the bladders may be detachable, shows that Sato considers the gas bag/bladder to be permanently fixed to the band, which is further counter to another embodiment of the applicant's invention for a detachable gas bladder.

Sato continues to state and discuss the concept of a belt plus a bag, therefore continuing to reinforce he has not contemplated a similar construction like the applicant is disclosing. Likewise, Sato continues to describe the nature of the compression force applied as necessarily 100% around the circumference, and evenly distributed, which again continues to reinforce that he does not truly understand the physics of what is happening, or contemplate other methods of targeting compression zones. Finally, Sato explicitly states the potential problem of excessive compression on the muscle during contraction and how this can lead to safety concerns, and therein cements the idea that pressure spikes are to be avoided. Sato's suggestion for how to remedy this is to make the belt material (in addition to the gas bag) elastic, however, as Sato has previously disclosed in prior patents, this necessitates a limiter plate and increases the cost and complexity. Sato's principle invention therefore is the addition of a second strap on the band to be grabbed by the user's other hand, to help avoid rotation and properly position the band. However, this is just adding yet more components to the solution instead of solving the underlying problems, in this case rotation and the need to apply significant initial tension. As a note, Sato does describe a thin inner fabric, but discusses this only in the context of creating a soft surface interface between the user and the belt. KAATSU's recommended guidelines actually suggest applying the bands over clothing (presumably to prevent pinching of the skin), and thus this design element is really not necessary. More importantly, it is clear that this inner fabric is not intended to be a spacer or load distribution mechanism as will be described by the applicant.

Sato's concept for an overlapping belt, and his requirement that the tube cover the entire range of muscles to be compressed, leads to a very long and bulky band. For smaller users, the band may wrap more than once around the limb and this creates an annoying bump on the limb that interferes with normal movement of the arm or leg. This is a big problem as it alters natural movement and will prohibit use in areas like performance training and rehabilitation where proper form and movement are necessary. The applicant's band, but shrinking in circumference when inflated, actually reduces its circumference and moves inward, and having a thinner profile (because of no limiter plates and other components), stays much tighter against the skin and ameliorates these interference problems.

KAATSU bands also come in 6 different sizes (ranging from 18-70 cm), however because of the applicant's discovery that the entire limb doesn't need to be compressed, in combination with the applicants overlapping fold-back design disclosed herein, the applicant's invention is able to accommodate a larger range with only 4 sizes of bands ranging from 19-77.5 cm. This reduction in parts means better economies of scale and easier manufacturing and inventory management.

KAATSU bands are further not meant to be washed and therefore are prone to accumulating bacteria and sweat. The applicant will disclose design features and systems for making maintenance of the belts simple, effective, and sanitary.

Sato's designs for inflatable bands incorporating a long tubular hot dog shape end up putting a concentrated pressure or focused line loading around the muscle where the apex of the tube is pushing. This becomes uncomfortable during use, and as stated above, can rub on a muscle and has been observed to cause bruising. The applicant's design of a series of chambers, and optional compliant edging with optional relief cuts, puts a much more cushiony feeling against the limb as the pressure is distributed over a larger area, contours better to the skin, and doesn't have a line load feeling because the radius of curvature of the inflated chambers, or pockets, is more than a KAATSU bladder when inflated. In practice, this dramatically improves the comfort and adherence of BFR training.

Sato's designs, as repeatedly stated above all recommend using elastic components to avoid pressure spikes and improve comfort. However, Sato has filed several patents as to how to combat the problems that this elasticity introduces due to the tendency of the tube to inflate away from the body instead of toward it. The applicant's invention has not only solved the inflation away from the body problem, but has simultaneously solved the spring requirement. Further, the applicant's invention functions with inelastic material to provide a better spring than with elastic material, and is hence completely contrary to Sato's designs in multiple ways, yet achieves similar properties with fewer materials. U.S. Pat. No. 8,182,403 & US2015/0150560A1

Sato continues to improve and perfect his KAATSU Training method in U.S. Pat. No. 8,182,403 to Sato and pending application US2015/0150560A1, however these applications offer nothing new in terms of band design, and continue to use the same language and concepts around a bag plus a belt, elasticity which requires limiting members, and precision of pressure control, which is inherently better in the applicant's invention. The patent mainly describes other methods of implementation and using automated cycling of the pressure as a warmup for the user to reduce the chance of occlusion when higher pressures are used. Sato explains that without cycling, a certain lower pressure will lead to occlusion than with cycling, and that a higher pressure is more optimal in terms of effect of the technique. In relation to the blood flow restriction system itself, the system of Sato is substantially the same as previously described in U.S. Pat. Nos. 8,021,283 & 8,328,693, and therefore the shortcomings of a full automated system, when compared with a manual inflation plus electromechanical pressure control system, are likewise similar to previously laid out. However, Sato offers yet another important comment that further supports the fact that, while he has invented a very useful technique with supporting hardware, he still fails to understand the interplay of the human physiology and how it relates to the design of the belts themselves. Sato describes in detail how cycling of the pressures between a minimum and maximum value, and doing so prior to training, serves as a valuable warmup and preventive measure against over compression and venous occlusion. Sato further lays out specific pressure ranges and discusses minimum step increments of 30 mmHg. However, not once does Sato mention the importance of band design, and in particular the width, and its effect on the various pressure levels. In fact, a wider cuff, when inflated to a given pressure, will displace a larger amount of tissue on the limb than a narrow band, and therefore lead to occlusion at lower pressures, even lower than what Sato has recommended. Similarly, minimum steps would need to be adjusted downwards for wider belts. Because Sato does not discuss this aspect at all, one is led to believe that he doesn't understand the ramifications of the specific band design, and in particular the width, as it relates to what is going on in the limb. This is further evidenced by Sato's discussion of the upper range or pressures to which to cycle being equal to systolic pressure for the arms, and systolic+20 mmHg for the legs, however Sato fails to give any guidance as to how these numbers should be varied based on the band design or user body type. Finally, the object of the invention is to provide an optimal cuff width for a given limb circumference as will be described below. As Sato fails to detail the importance of cuff, it seems he doesn't understand that two small a width will result in pressures that are so high they are painful and almost cut the skin vs. cuffs that are too wide and impede muscle movement or occlude blood flow. It is therefore beneficial, as the applicant will show, to have a band design that inherently makes it difficult to reach occlusion pressures during BFR training, and reduces the need for a cycling, or warmup phase, as a countermeasure to occlusion at suboptimal pressures. Further still, the applicant's manual inflation means not only reduces the cost and complexity, but forces the user to do muscle contractions that squeeze some blood past the obstruction, and itself serves as a warmup as previous stated, rendering an automated cycling process less efficient. Finally, Sato continues to reinforce the key aspects of the band design, that the band outer piece should be elastic, necessitating a limiter plate, and that the pneumatic bag be a separate piece attached to the band and approximately equal to the circumference of the limb.

In relation to the issue of comfort, which Sato and Wasowski both deem of critical importance, Sato also fails to recognize that the band design he sets forth will result in kinking, and that these kinks will reduce the uniform compression Sato says is important, but even more importantly, that these kinks will pinch the user's skin. The applicant has witnessed such effects first hand, and as the pressures are increased this pinch can be quite painful on sensitive surfaces like the inner arm or inner thigh. The application will provide a band design that shrinks under inflation, as opposed to expansion, and thereby eliminates any possibility of kinking.

Overall it seems that Sato's inventions are additive vs. integrative, meaning that he made a concept, and came across problems, and so added more features, such as the limiter plates, to try and solve those problems, rather than stepping back and figuring out how to make the design more efficient. The applicant has taken an integrative approach and the result is a belt design that has fewer components, is simpler to construct, and performs better in terms of comfort to the user. Sato's various additions in looking at a manufactured KAATSU belt appear to include the following:

a. Inflation Bladder—
   a single long narrow elastic (latex or neoprene) bladder. Unconstrained inflation shape is a long straight tube that expands in length and diameter with increasing pressure. When placed around a cylinder or limb, the bladder inflates radially outward (away from) the limb, the opposite of what is required.

b. Constraint from Radial Expansion of the Band—
   In order to force inward expansion rather than radially outward expansion—to apply pressure to the skin—the bladder is constrained by an outer stiffer band, or stiffener plates. The band is now forced to expand against the skin and may extrude out the sides under high pressure if the bladder is sufficiently flexible.

c. Band Shape Distortion when Around a Limb—
   Constraint from radial expansion as the bladder inflates causes the inner annulus of the bladder to buckle, i.e., kink, at points around the circumference (not ideal).

d. Bladder Constraint from Lateral Extrusion—
   It appears stiffener tubes or ribs extend the length of the bladder on each side in order to prevent bladder extrusion and act to contain the bladder within the width of the outer stiffer band.

e. Maintenance of Band Cross-Sectional Profile Under Pressure—
   Square or rectangular plastic plates cover the outer surface of the stiffer band to add lateral stiffness which helps to maintain a flat band profile, presumably to maintain a more uniform skin pressure across the band.

f. Band Elasticity for Venous Return—
   Stretch is provided by an outer neoprene band which also acts to constrain the bladder from outward expansion—it expands some, but not much.

g. Packaging and Size—
   The above structural elements are contained and held in place with a fabric sleeve. With the various elements stacked together, the total package is quite thick, approximately to ½ inch uninflated and close to 1 inch inflated.

h. Conforming to Limb on Inflation—
   The KAATSU band has limited ability to conform to the limb unless placed on a cylindrical section because of its thickness.

Conversely, the applicant has invented a simplified design with the benefits of:

providing springiness during muscle contraction, staying low profile against the body where the outermost diameter of the inflated belt is less than the outermost diameter of the non-inflated belt, compressing the body both via the shrinkage of the circumference up to a theoretical maximum of 36% and the bulging of the chambers up to a maximum of the chamber width, W, divided by Pi (W/Pi), contouring to the body to allow overlap of a portion of the band in a fold back configuration that leads to few required sizes, anti-rotation features to apply a fold back design to one's own arm, elimination of kinking and pinching the skin, and targeting specific ranges on the body to compress.

The applicant's design leads to an optimal inflatable belt design and BFR training system over current inventions and existing products.

It is worth pointing out again that the design of the belt and understanding the physics of what is happening is critical to providing an effective, yet comfortable BFR experience. By keeping the pressures more constant and reducing the spikes, it is also safer. Sato's efforts to combat this problem were purported to be solved by adding active control means to the system but this has multiple downsides. To start, this means tethering the user to the pressure control system, and thus preventing them from doing dynamic movements, which is an important aspect taught in KAATSU Training. Secondly, the muscle contractions would squeeze out a significant amount of air during a single contraction, and the pumps employed in KAATSU equipment are not strong enough to re-inflate the bands in time to prepare for the next contraction. Significantly larger pumps would be required, thereby exacerbating the stated arguments of why electromechanical pumps are bad. The applicant's inflatable belt designs have been shown to keep the pressure in the inflatable belts at a more constant level than Sato's designs, and thus all such problems related to pressure regulation have been substantially reduced by the applicant's invention.

Finally a summary comparison of the KAATSU band vs. the applicant's design as disclosed herein is as follows:

a. The KAATSU inflatable chamber grows in length and diameter on inflation; the applicant's belt shrinks in length on inflation.

b. The KAATSU inflatable chamber needs an additional outer stiffer layer to prevent bladder expansion away from the skin; the applicant's inflatable chamber requires no additional structural member because the inflatable chamber itself contracts uniformly around the limb.

c. The KAATSU inflatable chamber kinks on the inner annulus when inflated around a limb; the applicant's inflatable chamber has no tendency to straighten and conforms without force around a limb.

d. the KAATSU inflatable chamber has stiff edges, likely to prevent lateral extrusion of the chamber; the applicant's inflatable chamber has no such tendency and needs no additional structural element.

e. the KAATSU band needs stiff limiter plate pieces around the circumference to maintain a flatter band cross-sectional profile, presumably because the overlap profile would require affixing the overlapped portion on a curved surface otherwise, which would be unstable; the applicant's design requires no such additional structural element because each inflated cylinder provides the needed lateral stiffness.

f. The KAATSU outer stiffener made of separate plates, or a wire doubles to provide some band stretch (elasticity) for venous return; the applicant's design requires no such added structural element because the inflatable chambers (which are the entire band) are its own spring element when inflated, either fully or even partially.

g. The KAATSU band with all the extra materials is on the order of ½ to 1 inch thick; the applicant's design is on the order of 0.050 inch thick without soft neoprene backing and ~0.200 inch thick with the neoprene backing.

h. The KAATSU band has some restricted conformability around a limb because of thickness and stiffness when inflated; the applicants inflatable chambers (and the entire band) has no such limitations because the sealed seam separating cylinder chambers acts as a hinge with an additional rotational (~±30 degrees of rotation) to accommodate more non-cylindrical cross-sections.

Accordingly, besides the objects and advantages of an inflatable belt for use in a blood flow restriction system described in this specification, several objects and advantages of the present invention are:

a. to provide an inflatable belt that is simple and cheap to build, b. to provide an inflatable belt that is designed to improve the comfort for the user, c. to provide an inflatable belt that distributes the compression load onto the user's body in a more even manner to improve the comfort for the user, d. to provide an inflatable belt that keeps pressure spikes to a minimum in the belt during muscle contraction via a spring property of the belt, e. to provide an inflatable belt that is easy for a single person to don and remove, f. to provide an inflatable belt that is compact, lightweight, and easy to transport, g. to provide an inflatable belt that works for a range of user body types, h. to provide a countermeasure to rotation when putting an inflatable belt on one's own body, i. to provide a means of limiting pressures in an inflatable belt to ensure that uneducated user's cannot use the inflatable belt unsafely, j. to provide a pre-inflated belt that does not require connection or inclusion of an inflation means, yet provides the benefit of the inflatable concepts, k. to provide a countermeasure to kinking of the inflatable belt and pinching of the user's skin, l. to optimize the compression range of a targeting inflatable belt for performing BFR, wherein the compression region is only so large as to sufficiently compress necessary blood vessels, but does not encompass the entire limb, or overlap key problematic muscles such as the hip flexor or tricep, m. to provide a fully molded inflatable belt that incorporates sufficient features and dimensions to hold its location on the user's body, yet provide sufficient compression to accomplish the desired BFR effect, n. to provide an inflatable belt that stays low profile against the body, o. to provide an inflatable belt that compresses the body both via the shrinkage of the circumference and the inflation of chambers, p. to provide an inflatable belt that contours to the body, q. to provide an inflatable belt that allows overlap of a portion of the belt in a fold-back configuration that leads to few required sizes to cover a full range of limb girths, r. to provide additional members that facilitate a snap on bracelet for performing BFR, similar to polyurethane coated marker bracelets used by runners, and incorporating sufficient features so as to provide enough compression to attain the desired BFR effect.

Still further objects and advantages will become apparent from a consideration of the ensuing description and drawings.

| DRAWINGS REFERENCE NUMERALS |
| --- |
| 90 limb |
| 100 inflatable belt |
| 101 inner belt material |
| 102 outer belt material |
| 103 inflatable chamber |

-continued

DRAWINGS REFERENCE NUMERALS 104 input port
105 belt fastening means
106 inflation means
107 belt valve
108 gas flow shutoff means
109 airflow
110 first fastening means
111 second fastening means
112
115 loop coupler
116 blood flow restriction system
117 pressure limiting valve
118 adjustable release valve
119 gas hose
120 valve coupling
122 height
123 width
124 chamber connecting tube
125 coloring element
126 reflective element
127 target compression zone
128 compression relief zone
129 chamber connection joint
130 handle
131 edging
132 cutout relief
133 inflatable length
134 non-inflated length
135 shrinkage factor
136 chamber inflated diameter
137 chamber deflated width
138 pressure gauge
139 overlap length
200 body interfacing component
201 friction surface
202 attachment pocket
300 single piece inflatable belt
301 distance locking peg
302 distance locking hole
303 single piece body
400 targeting inflatable belt
600 storage apparatus
601 post
602 venting means
701 open position circumference
702 closed position circumference
703 outermost circumference
801 open position
802 closed position
803 working position
804 working position circumference
901 buckling zone
902 cylindrical zone
903 edge effect zone
904 edge
1000 snap-on inflatable belt
1001 single inflatable chamber
1002 coil spring
1003 snap-on belt body Preferred Embodiment Description. A preferred embodiment of an inflatable belt 100 for use in a BFR system is shown in FIG. 1A. The inflatable belt 100 is comprised of an outer belt material 102 which is preferably substantially inelastic, or non-stretch, such as single or double side urethane coated ballistic nylon of 200 denier. Such class of material is commonly referred to in the fabrics world as non-stretch, and where the term inelastic is used in this application, the reader shall understand the applicant's intent is to refer to this non-stretch class of material. The reader shall further understand that non-stretch fabric is understood in the industry to have certain characteristics regarding stretch, such as in the warp and fill directions, and other materials which may not necessarily be considered fabrics, but that have similar non-stretch properties shall also be considered "non-stretch" or "inelastic" within the context of this application. The reader shall understand that material properties of the belt may be changed to alter the elastic compressive response as described in the operation section of the preferred embodiment. For example, a stiffer material may provide a harder, stronger response, and a more elastic material may provide a softer response. This may be advantageous when designing the inflatable belt 100 for different types of users. For example those with big strong limbs may desire a stronger, harder response while the elderly or frail may desire a softer response from the belt. The strength/weight of the fabric may be lighter or heavier, such as 50 denier or 800 denier, and lighter fabric may provide additional advantages in terms of cost, weight, and compliance for conforming to the body. Preferred aspects of the outer belt material 102 are: it doesn't stretch or stretches to a very small degree, can hold a gas, or is substantially airtight, and can be connected in an airtight fashion to an inner belt material 101, forming a series of inflatable chambers 103. The quantity of chambers may be changed depending on the desired width of the inflatable belt 100 and desired range of limb sizes the belt must cover, and whether the concept of targeted compression zones will be used as discussed later, but it is preferred there are at least two inflatable chambers 103. Ideally the outer belt material 102 is also machine washable. A substantially inelastic outer belt material 102 removes the need for complicated and expensive limiting plates and other such constructions as described by Sato. The reader shall note that the outer belt material 102 could also be elastic, it would just be less effective. Additionally, limiter plates, or alternatively a strip on inelastic fabric, could be added around, or fixed to the elastic outer belt material 102 to limit expansion past a certain degree without departing from the spirit of this invention, but this is not necessary. The connection between the outer belt material 102 and the inner belt material 101 is preferably heat sealed, or RF welded, or as otherwise described in the prior art, however the reader may note that many means for attaching two fabric like materials in an airtight fashion, such as bonding, may be considered within the scope of this invention. The width of the outer belt material 102 may be approximately 1-3 in for inflatable belts 100 intended for the arms and approximately 2-4.5 in for inflatable belts 100 intended for the legs. However, the reader may note that, as described in other embodiments the shape may also be non-rectangular and may span a wider or narrower region at different points around the circumference as further illustrated in FIG. 4. In general, for areas where freedom of movement is needed a narrower section may be beneficial, and for areas where a directed compressive load needs to be applied, a wider section may be beneficial.

The inner belt material 101 may be an elastic material or preferably an inelastic material, and may have a significantly higher degree of elasticity than, or identical elasticity to, the outer belt material 102. In the case of bigger more muscular limbs, the inner belt material 101 being elastic may allow the inflatable chambers 103 to bulge more into the limb and provide a better compressive action for the user. The reader shall understand the applicant contemplates mixing and matching materials and material properties to alter the behavior to best suit the user of the inflatable belt 100. The inner belt material 101 is preferably also washable, but not necessarily so. The inner belt material 101 similarly may be connectable to the outer belt material in a substantially airtight fashion, and may itself be made of a substantially airtight material. Ideally the inner belt material 101 is also machine washable. For example the inner belt material 101 may be polyurethane coated nylon stretch fabric, or may be exactly the same material as the outer belt material 102, providing fewer amount of different parts and therefore better economies of scale in fabrication.

Figure 1B:
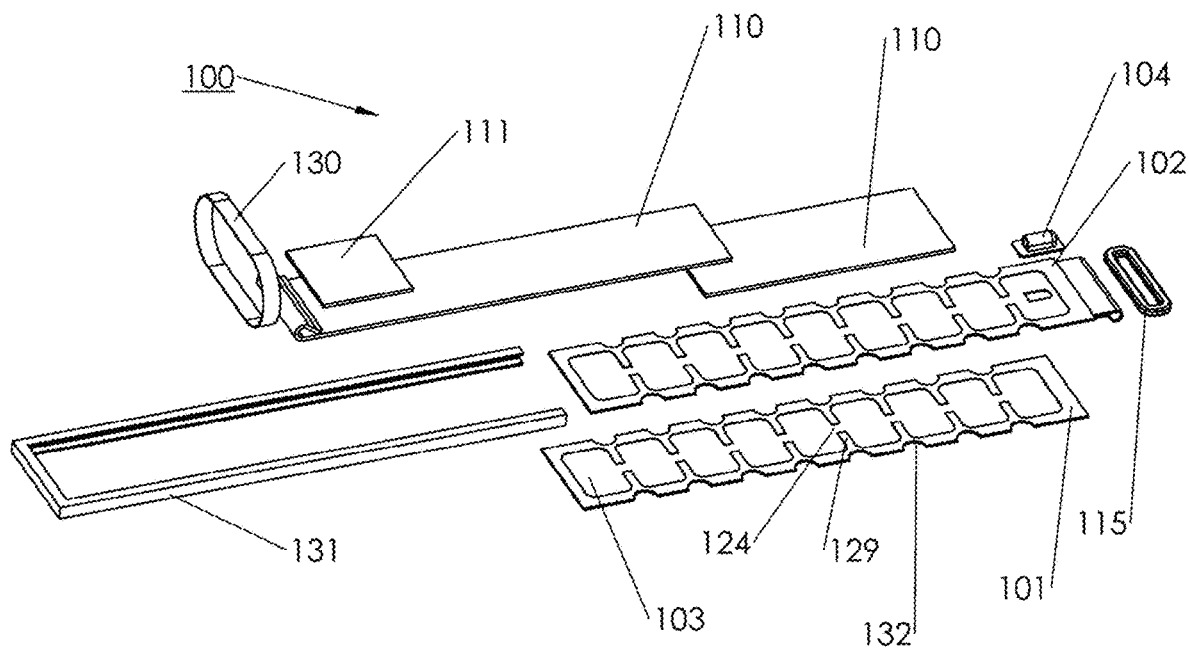
FIG. 1B—shows the inflatable belt of FIG. 1A but in an exploded view.

When the outer belt material 102 and inner belt material 101 are connected, they form a series of interconnected inflatable chambers 103 as shown in FIGS. 1A,1B. The connection profile forming the inflatable chambers 103, may be along the entire length of the inner belt material 101 or outer belt material 102 as shown in FIGS. 1A,1B, or may be along only a portion thereof, forming clusters of inflatable chambers as seen in FIG. 1I. An inflatable chamber 103 that is formed along a portion of the length of the inflatable belt 100 may have the advantage that it only applies compression to a specific region on the limb and thus reduces the overall sense of compression to the user, improving a feeling of comfort. The interconnected inflatable chamber 103 also need not be of equal size. The inflatable section of the belt may have a non-rectangular profile comprised of cylinders of different sizes as shown further in the embodiment of FIG. 4. Further still, in the configuration of FIG. 1A, the inflatable chamber 103 may not run through a loop coupler 115 and consequently would avoid the potential issues discussed by Sato in U.S. Pat. No. 8,992,397. The inflatable chambers 103 may be located anywhere along the length of the inflatable belt 100 and are not restricted to starting at one end.

The diameter of a cylinder and the ratio of cylinder length (height 122 in FIG. 1C) to cylinder diameter—known as the cylinder aspect ratio—are two important shape factors that affect the performance of the belt system as described in this application. Through theoretical considerations, experimentation, and practical considerations described in greater detail below, the applicant has arrived at ratios that work very well. The inflatable chambers 103, shown in their non-inflated state, have a height 122 to width 123 ratio (height/width) of approximately 3:2. This corresponds to cylinder aspect ratio (length/diameter) on inflation of approximately 2.4, meaning the inflated chamber length (length being substantially equal to height 122) is about 2.4 times longer than the diameter when fully inflated.

The inflatable chambers 103 in their deflated state have a height 122 greater than a width 123 and at a ratio of about, but not limited to (height:width) of (3:2). The height 122 and width 123 may vary in size and ratio without departing from the spirit or scope of this invention. For example the height-to-width ratio may be 9:8 on the low side to 6:1 on the high side and still achieve some amount of shrinking capability. The reader shall note that the height 122 and width 123 referred to herein, and as marked by the reference numerals, are for un-inflated dimensions and not for inflated dimensions. As discussed elsewhere in this application, the reader shall note the effect of increasing this height-to-width ratio reduces the end or edge effects providing better shrinking and compression. The downside is for a given inflatable belt 100 width, a larger ratio means shrinking the width, and therefore adding more chambers, which increases the number of chamber connecting joints 129, which do not shrink. Chamber connecting joints 129 forming a greater percent of the overall belt length acts counter to the goal of creating a maximally shrinking belt. Additionally, for a given length of belt and quantity of chambers, if the chamber connecting joints 129 form a larger proportion of the belt, the diameter of each chamber, when inflated will be smaller and so the additional compression achieved from the pressure of the inflatable chamber 103 pushing on the adjacent portion of the limb 90 itself is reduced.

A range of limb girths may be accommodated with varying lengths of belts and chamber sizes. Limb girths ranging from 19 cm to 32.5 cm may correlate to chamber height 122 of approximately 3-4 cm and chamber width 123 of 2-2.5 cm; limbs ranging from 30 cm to 47.5 cm may correlate to chamber height of approximately 3 cm-5 cm and chamber width of 2-3.5 cm; limbs ranging from 42.5 cm to 60 cm may correlate to chamber height of approximately 4.5-6 cm and chamber widths from 3-4 cm; limbs ranging from 55 cm to 77.5 cm may correlate to chamber height of approximately 4.5-7 cm and widths of 3-4.7 cm; and limbs from 72.5 cm and up may correlate to chamber height of 5 cm to 9 cm and chamber width of 3.3-6 cm. The reader shall note that these ranges are only some examples, but that dimensions stated herein may be increased or decreased without departing from the spirit of this invention. For example small arms of a child may use a chamber height of 2 cm whereas a body builder may use a chamber height of up to 10 cm for arms. For legs, a small child may use a chamber size of 3 cm whereas a body builder may use a size of up to 20 cm. These are but examples, and the reader shall understand that the applicant prefers a narrower belt for the benefits of avoiding complete stoppage of the blood flow, however such wider belt configurations may function with similar characteristics as narrower belts and as such, shall be considered within the scope of this invention.

The inflatable chambers 103 may be interconnected with a chamber connecting tube 124, or may have separate inflation sources. An advantage of the interconnection is a single inflation source is needed and air passes from one inflatable chamber 103 to the other. The chamber connecting tube 124 is smaller in width than the height 122 of the inflation chamber 103, and preferably connects the inflation chambers in the center of the inflatable belt 100, but may alternatively do so along any portion of the height of the inflatable chamber 103, including the ends of the inflatable chamber 103, or even on the width of the inflation chamber 103. The chamber connecting tube 124 may be formed within the welding process, as in the preferred embodiment, or may be a separate component that connects each chamber. The chamber connecting tube 124 is preferably just small enough as to let sufficient airflow 109 pass from one inflatable chamber 103 to the next without blocking airflow due to inadvertent kinking of the inflatable belt 100 prior to or during inflation. There may be only one chamber connecting tube 124 or multiple chamber connecting tubes to facilitate airflow 109. The corners of the chamber connecting tube 124 are preferably slightly rounded to reduce stress at this joint, and to facilitate opening and airflow 109 during inflation and deflation. Experiments indicated that a chamber connecting tube 124 dimension of approximately 0.1875"-0.375" wide and 0.1875"-0.375" long works very well, although the reader shall note these dimensions are but examples and not meant to limit the scope of this invention. For example, an inflatable belt 100 that has targeted inflation as described later, may have a gap of 1 in or more between clusters of inflatable chambers 103 and therefore require a longer, and potentially wider chamber connecting tube 124. The chamber connecting tube 124 is formed adjacent to at least one chamber connection joint 129. If the chamber connecting tube 124 is in the middle of the inflatable belt 100 as shown in FIG. 1A, then a chamber connection joint 129 is formed on either side of the chamber connecting tube 124. The chamber connection joint 129 may have one or more optional cutout reliefs 132 to allow the edges of the inflatable belt 100 along the width 123 of the inflatable chamber 103 to curl up and over a portion of the limb 90 as shown in FIG. 1G. The cutout relief 132 may be in the form of a semi-circle as shown in FIG. 1A, a slit as shown in FIG. 1G, or any other form that allows for additional compliance of the inflatable belt 100 for conforming to a limb 90. FIG. 1M further illustrates the purpose of the cutout relief 132 in showing a test inflatable belt 100 with all the inflatable chambers 103 exposed. In FIG. 1M the reader can clearly see buckling zones 901 located between each inflatable chamber 103 and in the middle of each inflatable chamber 103. The buckling zones 901 are created because as the centerline of the inflatable chambers 103 shrinks to form a circle, at cylindrical zone 902, the edge 904 similarly wants to shrink. However because the edge 904 is just fabric, the fabric must buckle in length, which is counter to its natural flat state, and there isn't enough material to form a cylinder, leading to edge effect zone 903 of the inflatable chamber 103. The less of an edge 904, and the more compliant the edge, the less buckling will be needed and the more cylindrical edge effect zone 903 becomes, and the more shrinkage the inflatable belt 100 can achieve. But, because the belt materials benefit from some stiffness as previously described, there will always be stress on the edges, which in turn want to straighten out. The tendency to straighten out acts as a counterforce to the belt wanting to shrink, and works against the goal of the applicant's design. The cutout reliefs 132, act to break up the edge effect, by removing part of the edge periodically, and therefore reduce the counterforce produced by the edge 904 on the inflatable belt 100, and improve the belt's elastic properties.

Figure 1E:
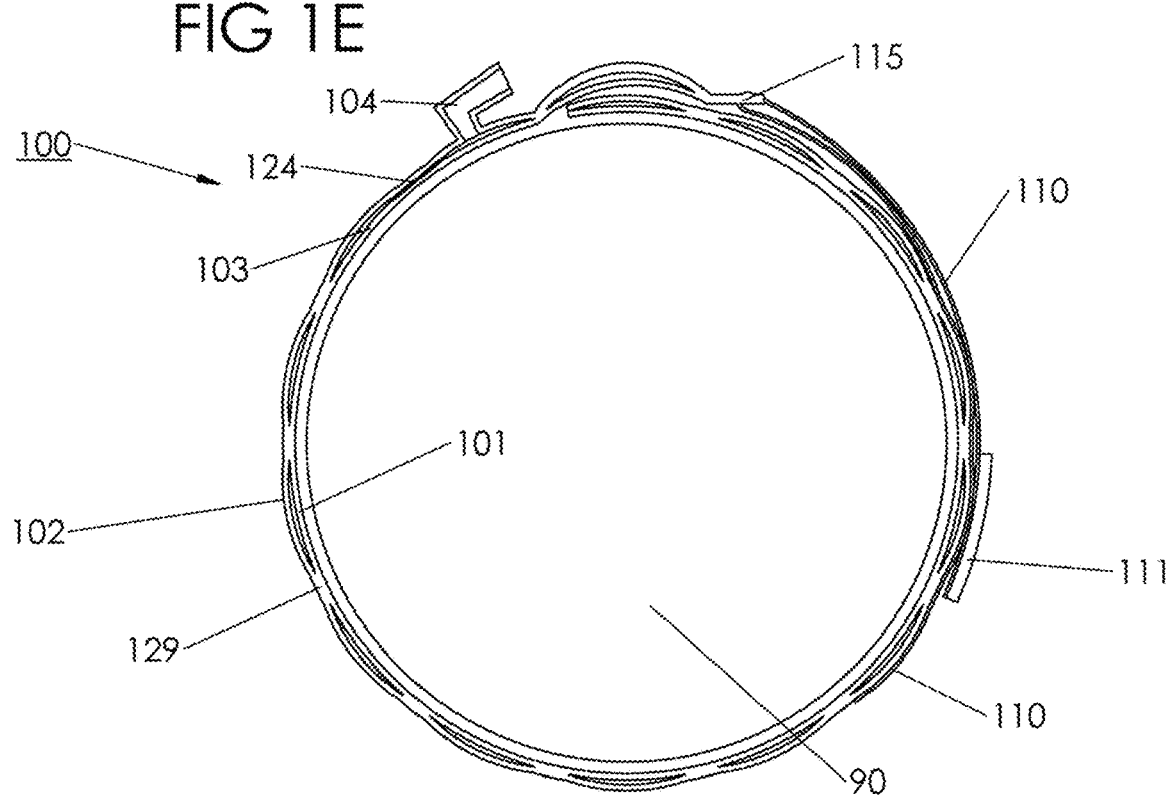
FIG. 1E—shows the inflatable belt of FIG. 1A in a deflated state, wrapped around a limb of a user and how the belt may overlap.
Figure 1F:
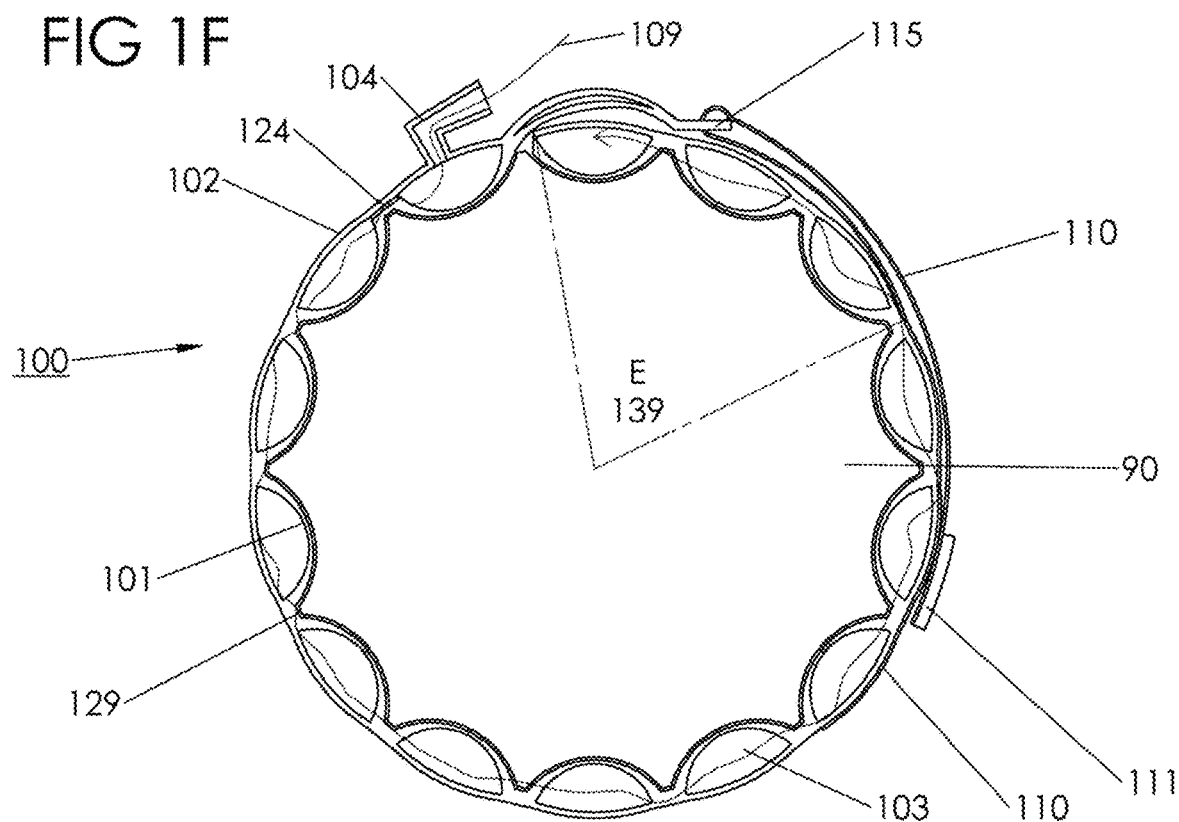
FIG. 1F—shows the inflatable belt of FIG. 1E, when inflated with a gas and how the belt may overlap.
Figure 1H:
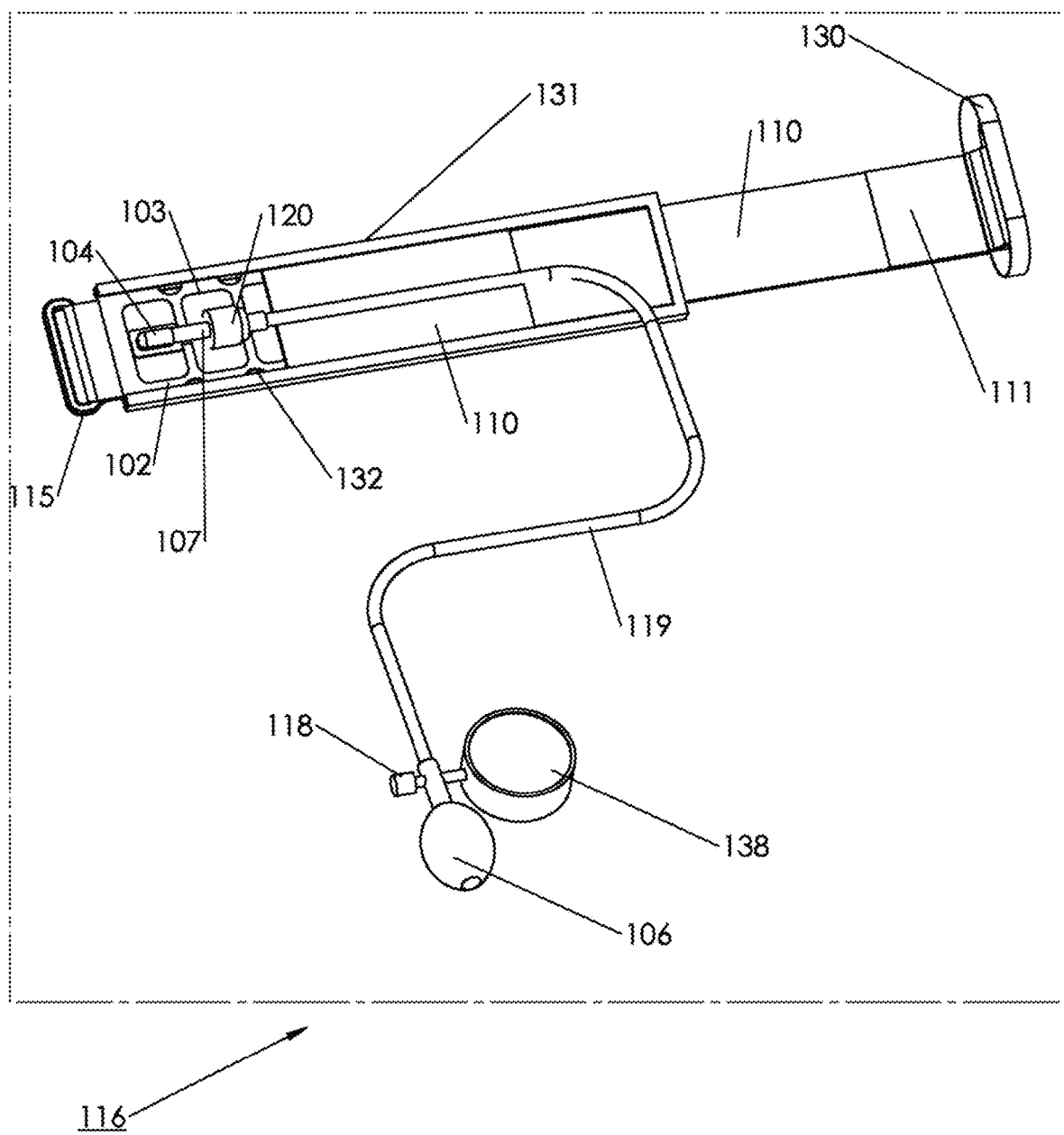
FIG. 1H—shows a BFR training system incorporating the inflatable belt of FIG. 1A and a manual inflation means with pressure readout.
Figures 1, 1I:
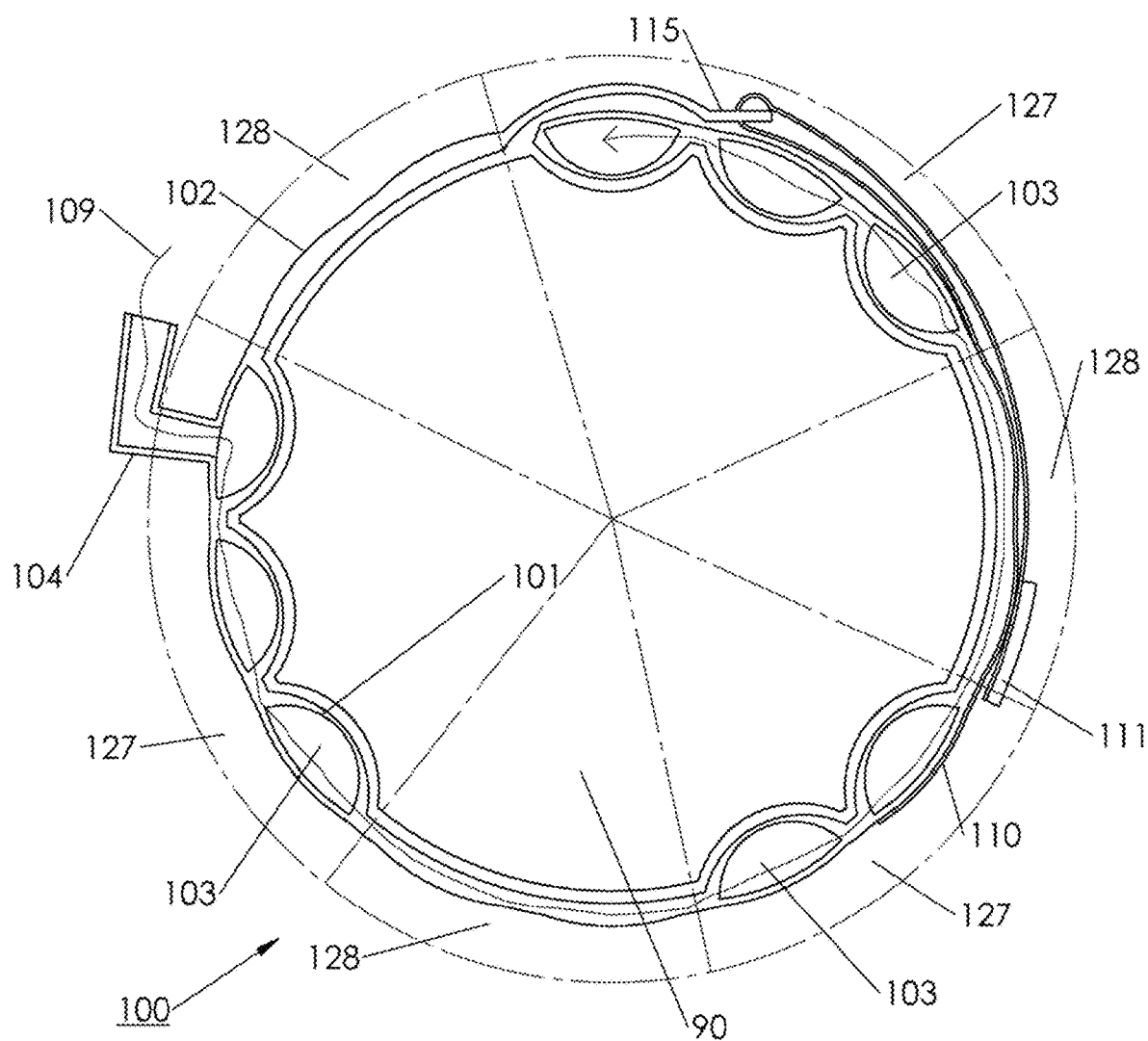
FIG. 1I-1—shows an inflatable belt similar to FIG. 1A, but with clusters of interconnected chambers to create target compression zones and compression relief zones.
Figures 1, 1I, 2, 3:
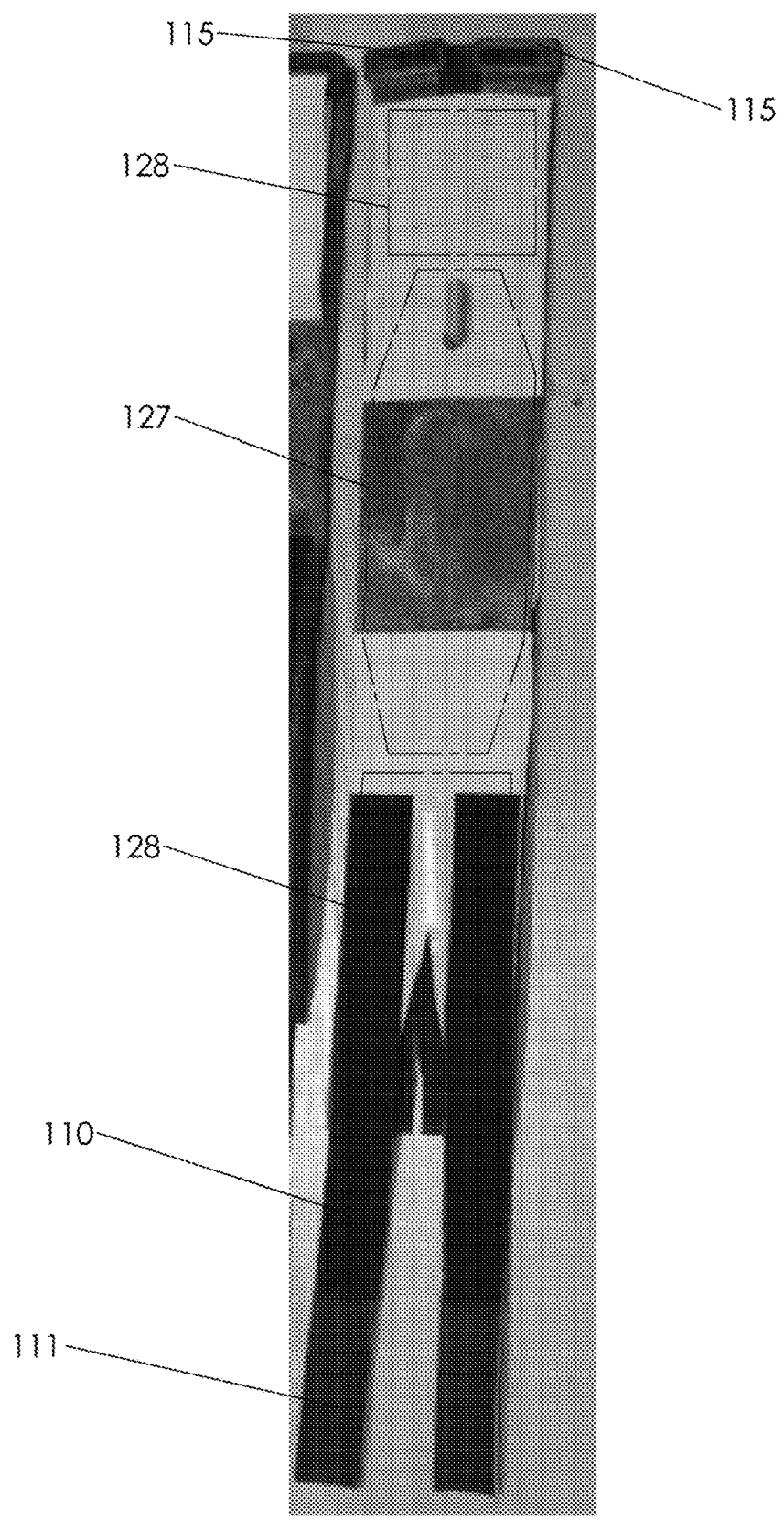
Figure 1J:
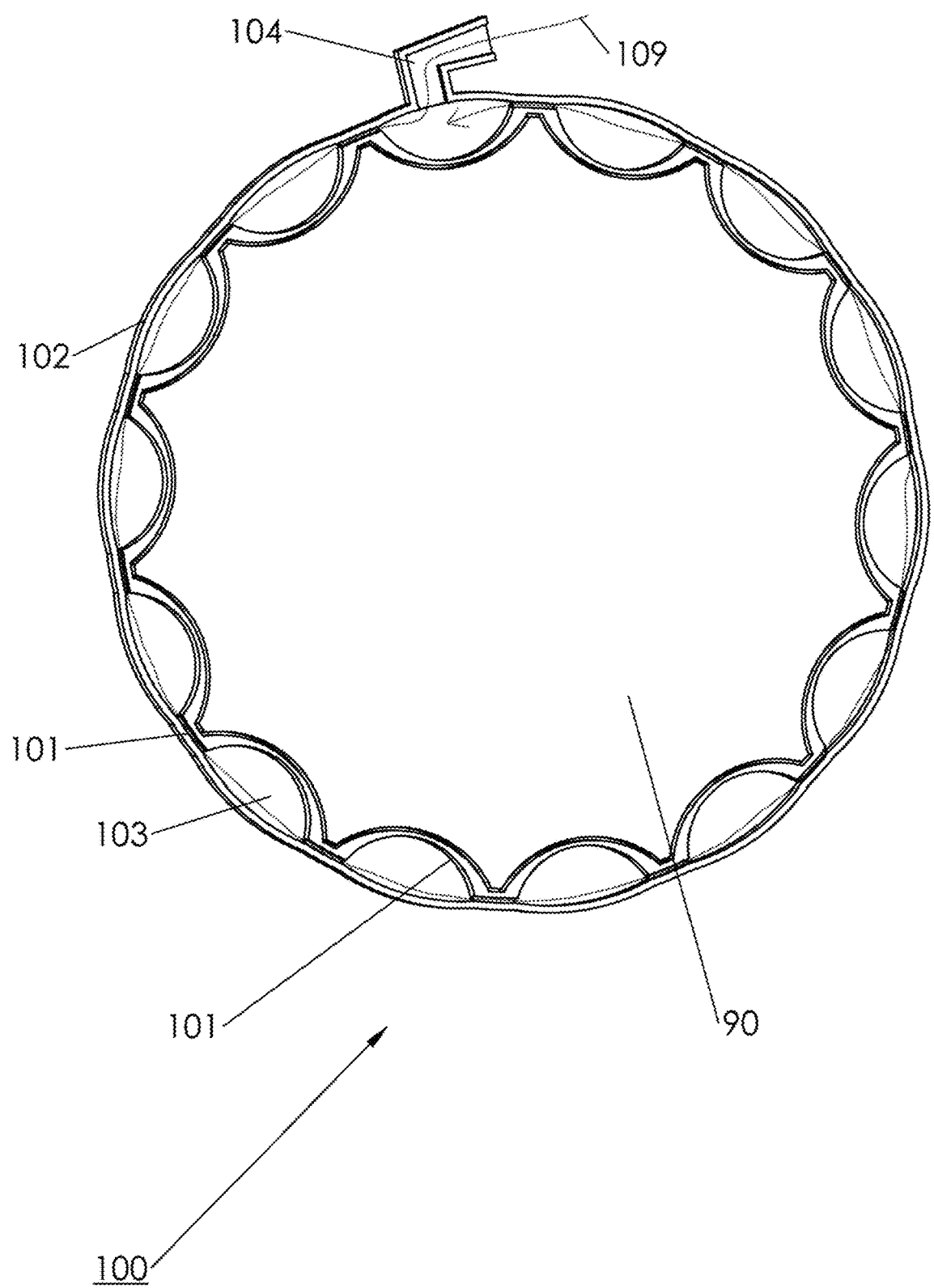
FIG. 1J—shows an inflatable belt similar to FIG. 1A, but of a fixed deflated circumference, relying fully on the shrinkage and bulging under inflation properties to compress a limb.
Figure 1L:
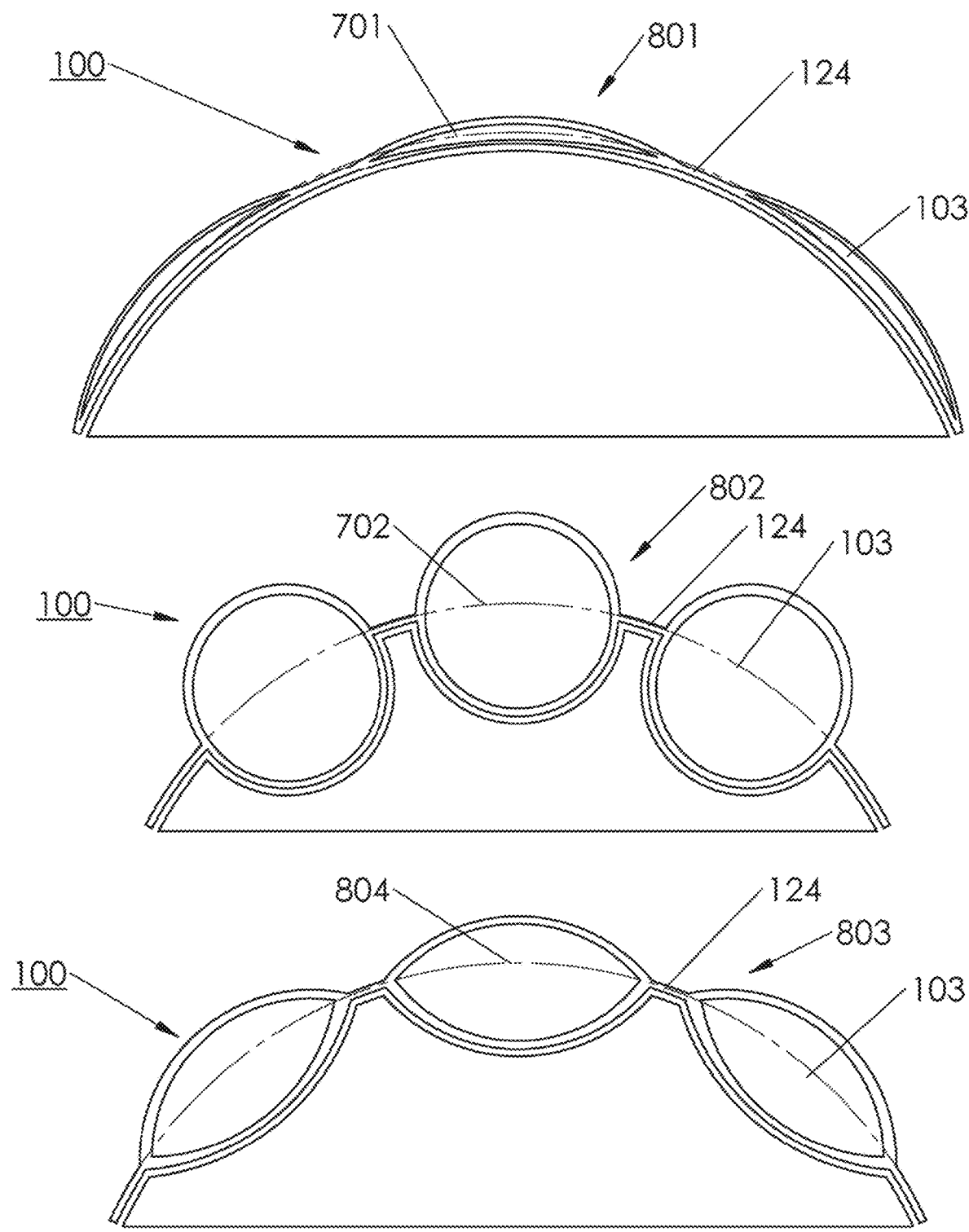
FIG. 1L—shows a section of an inflatable belt around a limb in an uninflated open position, an inflated closed position, and a slightly expanded working position reached during a muscle contraction.
Figure 1N:
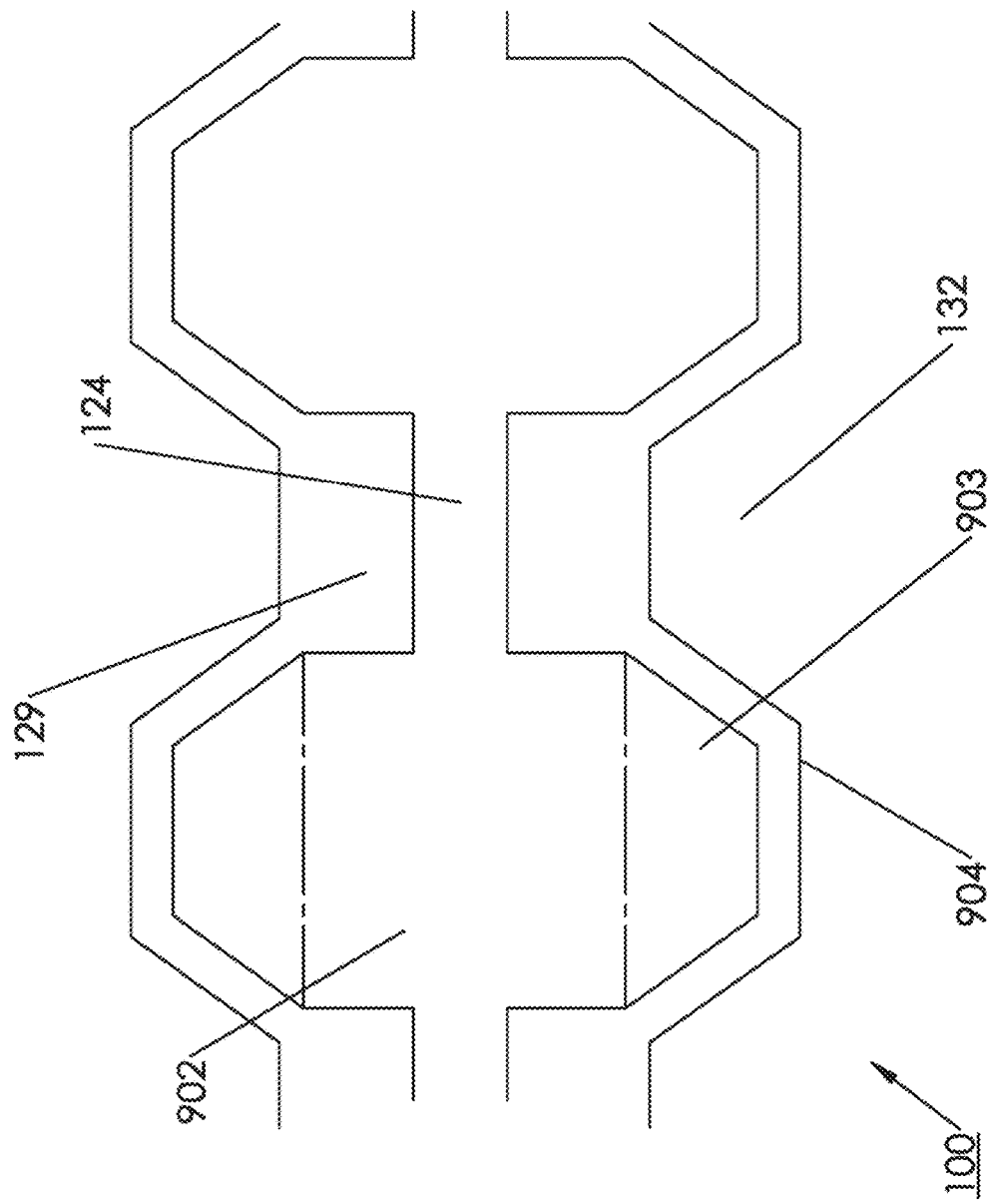
FIG. 1N—shows another configuration illustrating how modifying the shape of the inflatable chamber at the ends, so that the edge of the belt is non-linear, can improve the elastic properties of the belt by reducing the edge effects.

As another example to illustrate how the inflatable chamber 103 design may be modified to improve the edge effects, FIG. 1N shows polygonal chambers. The reader shall note this is but one illustration and curved chambers, or other shapes may similarly be used without departing from the spirit of the applicant's invention. In FIG. 1N, the portion of edge 904 that is must subjected to buckling is narrower and substantially shorter than inflatable chamber 103 width. Less material to compress and buckle means less of a counterforce and more effective curving of the cylindrical zone 902 for a given applied pressure. The reader shall note that edge effect zone 903 is shown as relatively large compared to cylindrical zone 902 for visual clarity only, but that the goal of any such modified design would be to increase the cylindrical zone to be as large a percentage of the overall width of inflatable belt 100 as possible to make the belt as efficient as possible for a given applied pressure. Similarly the reader shall note that chamber connecting joints 129 and chamber connecting tube 124 are shown relatively wide, but that the actual widths of these sections may similarly be reduced to make these non-inflated portions of the belt as small a percentage of the overall length as possible.

An input port 104 is in communication with the inflatable chamber 103 to allow a gas to flow into and out of the chamber. The input port 104 may be an RF weldable valve component, or simply a tube welded or heat sealed between the inner belt material 101 and outer belt material 102 as in an Intravenous (IV) bag. The input port 104 may protrude out one edge of the inflatable chamber 103 as shown in the previously filed provisional application 62/293,536, FIG. 1A-1, or may be connected perpendicular to the outer belt material 101 as shown in FIG. 1A. The input port 104 may be a straight, right angled, or slightly angled port. A port perpendicular to the inflatable belt 100 surface may have a benefit of being easy to connect an inflation means 106 (shown in FIG. 1H) versus a port that is parallel with the user's limb as would be in FIG. 1A. The specific material and method of fastening is not critical as long as an inlet is created in an airtight fashion. One or more valve configurations, such as a belt valve 107 (shown in FIG. 1H) may further be placed into the input port 104 as part of the inflatable belt 100, but this is not necessarily part of the assembly. As discussed in other embodiments in the previously filed provisional application referenced herein, there are many such valve configurations and combinations that produce beneficial results and the inflatable belt 100 of FIG. 1A may include any one of them, or none at all. The input port 104 may be placed anywhere along the length of the inflatable length 133 such that it is in communication with at least one inflatable chamber 103 to allow airflow 109 into the inflatable belt 100. The input port 104 is preferably located, but not limited as such, on the first inflatable chamber 103 adjacent to the loop coupler 115 as shown in FIG. 1A. The non-inflated length 134 in FIG. 1C is defined as the length of the first fastening means 110 protruding past the end of the inflatable length 133, and up to the second fastening means 111 such that when the inflatable belt 100 is formed into a loop, with the circumference equal to the maximum limb circumference the belt is designed for, then only the second fastening means 111 is looped back through the loop coupler 115, and fixed back immediately onto the first fastening means 110. This leaves a portion of the circumference under the first fastening means 110 that is not covered with inflatable chambers 103, and this distance is the non-inflated length 134. Similarly, the inflatable length 133 refers to the length of the inflatable belt 100 that is comprised of inflatable chambers 103, and forms substantially the rest of the circumferential length. The reader shall note that there is some extra small section of the circumference under the loop coupler 115 itself that forms a portion of the circumference when formed into a loop, and that dimensions of certain components in practice are designed to take into account this extra length. As it represents a very small portion of the overall circumference, this extra distance will be ignored for the purposes herein of explaining the construction and function of the inflatable belt 100. The reader shall further note it is possible to construct the end of inflatable belt 100 in such a way that loop coupler 115 rests on top of an inflatable chamber, for example by sewing, welding, or otherwise connecting the loop coupler 115 offset from one end of the inflatable belt 100. Prior art regarding occlusive cuffs discuss the discontinuities in pressure associated with edge overlaps, for example the loop coupler 115 concept, but since the applicant preferably has the loop coupler 115 placed over a portion of the limb 90 that is not critical for compressing the underlying vasculature, the applicant further differentiates his invention meant to restrict blood flow from other designs meant to occlude blood flow in the limb.

An optional belt spring (not shown) may be an elastic stretch webbing and may be coupled to the end of the outer belt material 102, through means known in the art, such as stitching. However, the belt spring may also be connected elsewhere along the length of the outer belt material 102, for example at the mid-point of the outer belt material 102. The main requirement of the belt spring is that it resides at a point along the circumference under tension, and is in direct, or indirect communication with the outer belt material 102. The belt spring concept is covered in the referenced previously filed provisional patent application 62/293,536 and all such concepts and descriptions shall apply to this invention. While the belt spring is not necessary in this invention, it may be implemented as an additional source of compliance under muscle contraction, but is not required for this invention to function.

A belt fastening means 105 (not indicated in the figures) is depicted in FIG. 1A by a first fastening means 110, shown as a strip of hook or loop fastener, and a second fastening means 111 depicted by a strip of mating hook or loop fastener. The belt fastening means 105 is used to lock an outer circumference of the inflatable belt 100 when applied around a user's limb (not shown). The reader may note that many such fastening means are known in the art, and hook and loop fasteners are but one version. Further such variations are described further below, and the reader may note these are but a few examples and may not limit the scope of this invention. The first fastening means 110, or second fastening means 111, may in fact have itself elastic properties and serve as the function of a belt spring (described above), thereby eliminating that optional component. The first fastening means 110 is in communication with the second fastening means 111 via attachment means such as sewing or welding, and additionally in communication with the outer belt material 102, also through suitable means such as, but not limited to, sewing or RF welding. As previously stated, if sewing is used, care is taken not to puncture the inflatable chambers 103. The first fastening means 110 may run along the length of the outer belt material 102, or only along a portion thereof. FIG. 1A shows the first fastening means 110 in communication with the outer belt material 102 only along a middle portion and stopping at a distance from one end, denoted in FIG. 1C by E which is the overlap length 139. Preferably the overlap length 139 ranges from 5 cm to 10 cm, but may be shorter or longer without departing from the spirit or scope of this invention. As noted elsewhere by the applicant, the inflatable belt 100 may also be constructed with no overlap length 129 without departing from the scope of this invention. Further, should the inner belt material 101 be made wider than the outer belt material 102, the first fastening means 110 may only be attached to the inner belt material 101. The reader may note this is one example of the many combinations and possibilities of combining components, varying their sizes, etc., and all such configurations may be considered within the scope and spirit of this invention. The first fastening means 110 may overhang one end of the inflatable length 133 as shown in FIG. 1C (the inflated length is represented by C in FIG. 1C) to provide a length of the inflatable belt 100 that is not covered by the inflatable chambers 103 when the inflatable belt 100 is laid flat on a table, the non-inflated length 134 represented by D in FIG. 1C. In this manner, the total length of the inflatable belt 100, when laid flat, is only partially covered by the inflatable chambers 103. The length of C+D plus whatever length may be added by the loop coupler 115 as discussed above, equals approximately the maximum available circumference to circle a limb that may fit inside the inflatable belt 100 when wrapped around a limb. In the preferred embodiment, the total lengths (C+D+loop coupler width) for the 4 main sizes of bands are approximately, but not limited to, 32.5 cm, 47.5 cm, 60 cm, and 77.5 cm. The length of the non-inflated length 134 in the configuration at the larger end of the limb circumference range, where not all of the limb is covered (i.e. targeted compression as described later), may cover approximately 70% of the overall limb circumference. These guidelines regarding targeted compression range, and inflation coverage of the limb are covered further in the alternate embodiments below and shall be construed to apply as referenced herein.

Figure 5:
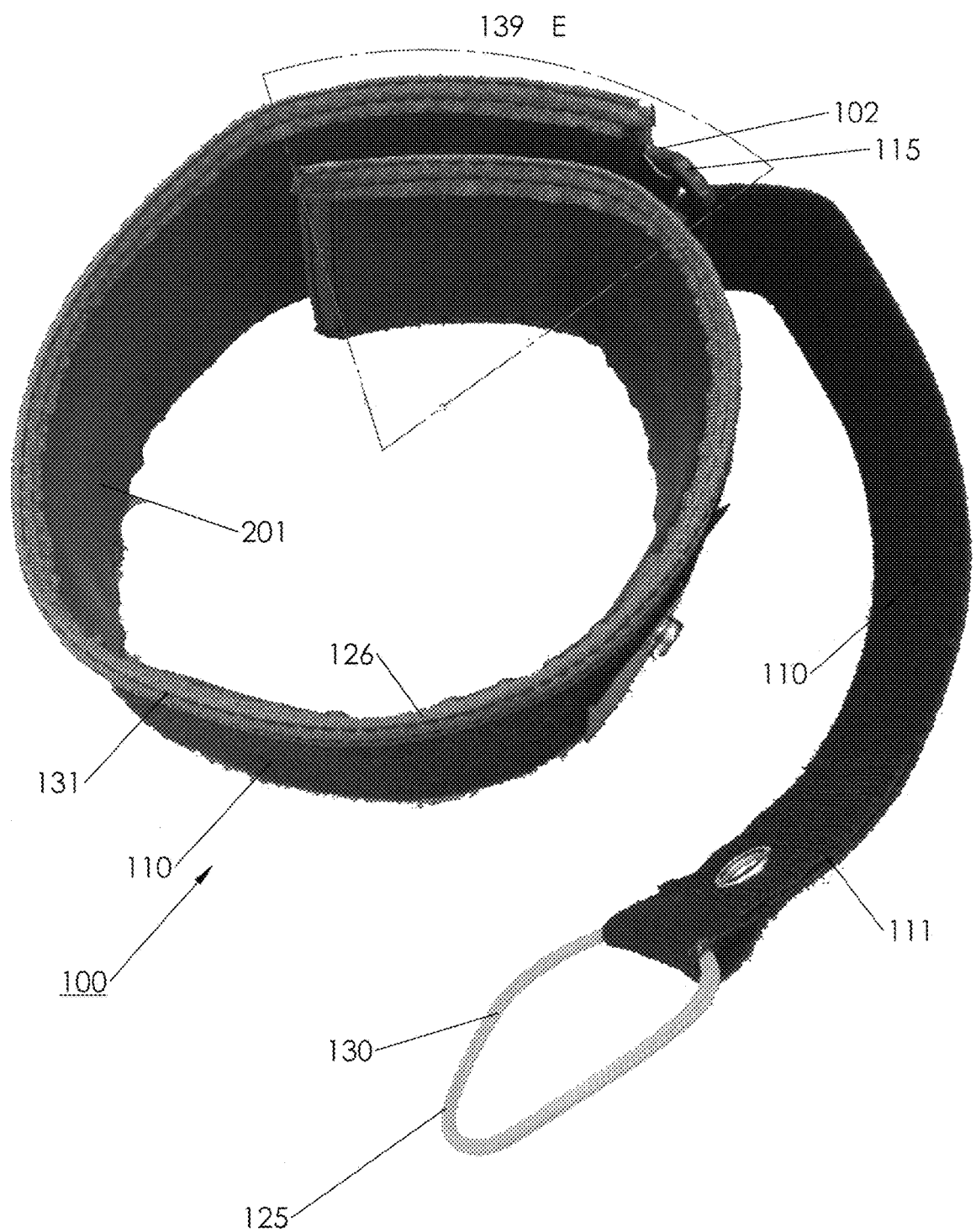
FIG. 5—shows a prototype inflatable belt built to accommodate an overlap region for accommodating a larger range of limb circumferences, further incorporating color identification and reflective features.

The overlap length 139, represented by E in FIG. 1C, subtracts from the inflatable length 133, represented by C in FIG. 1C, such that the target minimal size of the limb to be compressed is approximately equal to C minus E (configuration depicted in FIG. 5). In the preferred embodiment these minimum targets may be, but are not limited to, 19 cm, 30 cm, 42.5 cm, and 55 cm. A prototype inflatable belt 100 is shown in FIG. 5 in its minimal circumference configuration, where the overlap length 139 is fully overlapped by the other end of the inflatable length 133. As an extreme example, for a limb of 100 cm in circumference, the minimal coverage by the inflatable bladder required may be approximately 30 cm, yielding a bladder length of 30 cm. If 10 cm of these may be overlapped, the unavailable length is 20 cm and thus the belt may cover between 20 cm and 100 cm in limb circumference, giving 80 cm in range of muscles to be compressed. The reader shall note that while various dimensions and ranges have been suggested herein, these by no means shall limit the scope of this invention as additional sizes, or few sizes with less overlap may be perfectly suitable as described herein. Nor shall the inventions be limited to the overlap constructions depicted, but other straight-style belts, or other configurations may similarly be adapted to take advantage of the applicant's invention.

An optional handle 130 may be coupled to the end of the first fastening means 110 or the end of the second fastening means 111. The optional handle is preferably not rigid or stiff and instead be fabricated from ribbon, rope, thin plastic, or any other such tough and durable yet flexible material. While flexible material is preferred, the handle 130 may also be made of plastic or harder material. The handle 130 may optionally be colored, and may also be reflective. Coloring adds the function of distinguishing easily between different inflatable belt sizes. Reflective properties add the benefit of showing up at night for safety reasons if exercising outside, for example, on the street. The handle 130, shown as a loop may be any form that is easy to grab for tightening and loosening the inflatable belt 100.

A loop coupler 115 is provided at the opposite end of the inflatable belt 100, and may be attached via looping the outer belt material 102 and or inner belt material 101 over itself to capture the loop coupler 115, or may be attached with a separate material, or directly, should the loop coupler 115 have a sew-on, or weld-on tab. The loop coupler 115 may be any loop coupler known in the art, such as, but not limited to a metal or plastic fabric square loop. The loop coupler 115 may further be constructed as a hole in the end of the outer belt material 102 and/or inner belt material 101 thereby eliminating one component.

Figure 2A:
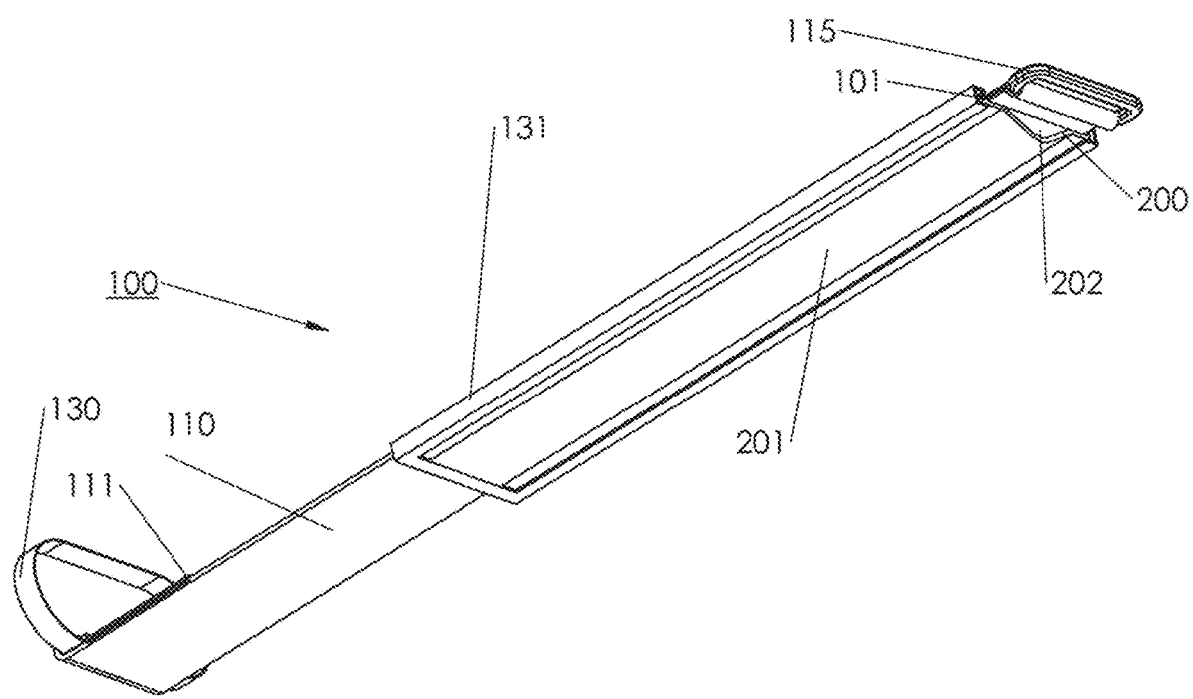
FIG. 2A—shows the inflatable belt of FIG. 1A with an added body interfacing component.

An optional body interfacing component 200 is provided in communication with the inner belt material 101. The body interfacing component 200 is not required for sufficient functional operation of the inflatable belt 100 of FIG. 1A, or other embodiments for that matter, but can offer some distinct advantages. As depicted in FIG. 2A, the body interfacing component 200 may be a strip of neoprene closed-cell foam rubber similar to wetsuit material, approximately 2-3 mm thick, but may be as thin as 1.5 mm. Strips up to 5 mm thick were tested and all provide sufficient properties as herein discussed. The body interfacing component 200 preferably has a high friction surface 201, or in the case of the neoprene rubber, a "skin" side that is faced inward to contact the user. This high friction surface 201 may grab the user, or user's clothing such that rotation during initial tensioning, and slip along the limb during exercise, is not observed. Further, the body interfacing component 200 spaces the inflatable chambers 103 off of the limb, in the case of FIG. 2A, by 2 mm. This gap between the inflatable chambers 103 and the user's limb (not shown) prescribes a certain additional volume that the inflatable chambers 103 may inflate into as the inflatable chambers 103 begin to compress the skin on the user's limb. In the case of FIG. 2A, where the body interfacing component 200 is neoprene closed-cell neoprene foam rubber, the inflatable chambers 103 will compress and squish the foam material directly underneath, and while the full volume filled by the neoprene is not vacated, enough of it is deformed to allow for substantially more air to fill into the inflatable chambers 103 than if the inflatable belt 100 were placed directly on the user's limb without the body interfacing component 200.

The body interfacing component 200 is further useful to facilitate donning of the inflatable belt 100 because, should the user want to employ this concept of spacing the inflatable chambers 103 off the surface, without the body interfacing component 200, there would be no friction or connection to the body (the gap would be filled with air) and this would cause the inflatable belt 100 to slip down on the arm, and be very difficult to put on. This phenomenon was demonstrated in experiments leading to the invention of the body interfacing component 200.

The body interfacing component 200 further helps to guard the user's skin against pinching. Pinching is a result of kinking of the inflatable chambers 103 that can be observed in the previously filed provisional application 62/293,536, FIG. 1L, where there are kinks in a non-pre-stretched belt of that provisional filing. Sato's bladder designs have this kinking problem, and while the invention of a series of inflatable chambers ameliorates and even solves the kinking issues, the body interfacing component 200 further distributes the load and eliminates any chance of pinching the skin. This pinching phenomenon was another observed problem with Sato's equipment where Sato only contemplates a thin liner, and not something that will disperse and eliminate kinks. The body interfacing component 200 further serves to distribute the applied load from the inflatable chamber 103 across a certain width, and on to the user's limb. It is an important property of the body interfacing component 200 that it be squishy to a sufficient degree so as to maintain a soft squishy interface to the user to provide maximum comfort, but be able to move and allow room for the inflatable chamber 103 to expand prior to compressing the user's limb.

Figure 2B:
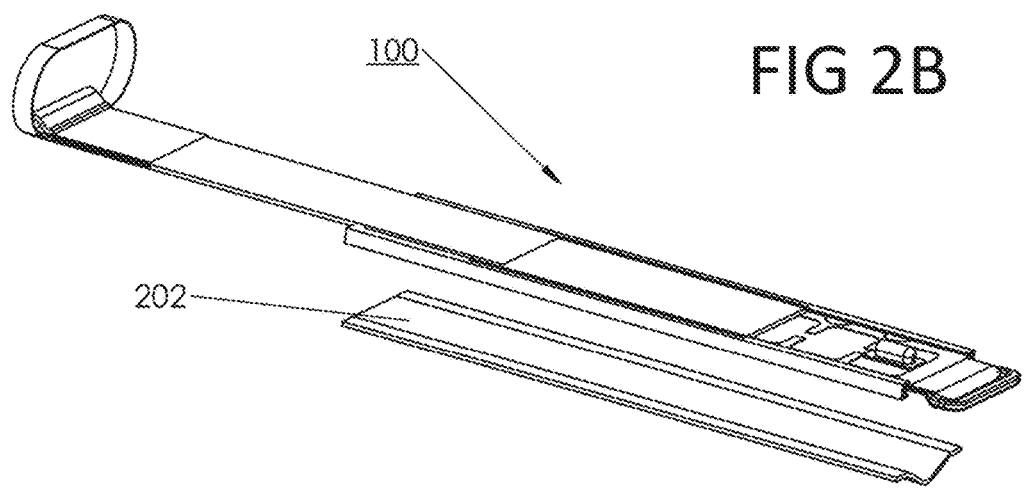
FIG. 2B—shows the inflatable belt of FIG. 2A with the body interfacing component being removable or detachable.

The body interfacing component 200 may be permanently connected to the inflatable belt 100 as shown in FIG. 2A, or may be removable as shown in FIG. 2B, or may be applied prior to application of the inflatable belt 100, and not attached to the inflatable belt 100 at all. In the case the body interfacing component 200 is attached to the inflatable belt 100, such attachment may be done with sewing, bonding or similar means. In the case the body interfacing component 200 is detachable, the body interfacing component 200 may further comprise or have fixed to it, a fastening means (not shown) and a mating fastening means similarly attached to the inflatable belt 100. The attachment means may be any such means, such as hook and loop fasteners, described or inferred to herein. The body interfacing component 200, in the detachable case, may serve an important function in that it may be measured by the user to match an arm circumference, or slightly less, for example 80-95% of an arm circumference. In this way, a standard prescribed length of the body interfacing component 200 can be instructed to all users, in a consistent guideline requiring no prior BFR experience, since measuring an arm circumference is something any ordinary user is capable of. This is another detriment to Sato's designs, in that there is no guidelines for where to start the initial tension of the belt, and this has been shown to have a dramatic effect on the efficacy, safety, and comfort of KAATSU Training. KAATSU, the company, publishes protocols for determining this starting tension, but the protocols require much trial and error and even multiple KAATSU Training sessions to start to narrow in on what is right for the individual. Solving this problem, of recommending in a consistent way, to novice users, how to properly tension the bands, provides a very big advantage in ease of use, to spread mass adoption. The length prescribed may be such that only very mild tension is initially applied once the inflatable band 100 is placed on the user's arm. Once the measurement is made, the user may cut the provided body interfacing component 200, or similarly fold it back, but in some way reduce the length to the prescribed amount for a given arm girth. Then the user may apply the body interfacing component 200 to the inflatable belt 100, connecting the two mating fastening means. In this way, the body interfacing component 200 now serves as a reference guide so that when the user goes to place the inflatable belt 100 on their arm, they must only pull the portion of the inflatable belt meant to feed through the loop coupler 115 (which may or may not include the inflatable chamber 103) until the two ends of the body interfacing component 200 butt up together. In fact the shape of the body interfacing component 200 may be such that it physically cannot go through the loop coupler 115 and thus serves as a simple, hard stop, requiring no thinking or expertise by the user in how tight to apply the initial tension, and further guaranteeing that the user cannot over tension the inflatable belt 100 which is a major advantage. The attachment means for connecting the body interfacing component 200 to the inflatable band 100 may be two strips along each side or may be a single flat strip across the entire width. In the case of a single strip however, since the attachment means is blocking the inflatable chamber 103, the attachment means must itself have similar squishy properties as the body interfacing component 200, or else it will block the air bladder from expanding sufficiently and compressing enough of the limb. Of course the use of hook and loop fastener is mainly discussed here because of its simplicity, but adhesive backed tape, magnets, or other non-permanent fastening means may also be used.

Further utility, features, connection means and configurations, etc. of the body interfacing component 200 have been described in the previously filed provisional application 62/293,536 referenced herein, and shall not be repeated for the sake of brevity. The reader shall recognize that all such features of the body interfacing component 200 benefit the inventions described in this invention, and may be added to the invention herein to achieve similar benefits as to the previously filed provisional application's invention.

Thus it can be seen that, while optional to the function of the inflatable belt 100 in providing BFR, the body interfacing component 200 can serve a variety of important roles to improve both the comfort, ease of use, and safety of the inflatable belt 100. The body interfacing component 200 may be of sufficient width, length and quantity to serve one or all of the above described functions, and does not need to fulfill all the requirements above to be considered valuable.

Edging 131 is placed around the perimeter of the inflatable length 133 to finish the edges and provide a smooth, soft, interface to the body. Edging 131 may be soft material such as felt, compliant, and may further be elastic. Elastic edging 131 adds the benefit that it will contour better to the body and should the inflatable belt 100 incorporate optional cutout reliefs 132, this elasticity may help such that the length of the edging 131 may increase or decrease slightly as the edge diameter needs to stretch, for example over an expanding bicep as shown in FIG. 1G. Should the optional body interfacing component 200 be used, the edging 131 may capture the body interfacing component 200, the outer belt fabric 102 and the inner belt fabric 101, and the first fastening means 110 all in a single stitch for example so that there is only one stitch used in assembling the construction. As described in prior art, the components, if properly coated may also be RF welded, or bonded together in a single operation. This improves cost savings and speed of manufacturing as sewing is the most labor intensive process. The potential cost savings are significant compared to Sato's construction which involves multiple connection steps, and more components. Should the body interfacing component 200 be used, the edging 131 may leave one end open, preferably the end close to the loop coupler 115 so that an attachment pocket 202 is formed as shown in FIGS. 2A-2B. This attachment pocket 202 may be used to air out the inside of the pocket after washing in a washing machine or after the bands during swimming, thus avoiding bacterial growth. As the inflatable belt 100 may be used in a hospital or medical setting, sanitation and washing is a key attribute not contemplated or mentioned in any of the prior patents.

Not shown is an optional stop mechanism that prevents the second fastening member 111 from exiting the loop coupler 115, and thus keeps the inflatable belt 100 in a substantially ring like shape. This can aid in donning the inflatable belt 100 as the user does not need to fiddle with feeding the second fastening means 111 through the loop coupler 115. Such a stop mechanism may be a physical barrier such as a bar or tab that is fixed with suitable means, such as sewing, to the second fastening means 111 or first fastening means 110 and mechanically interferes with the loop coupler 115 such that the first fastening means 110 cannot physically pass back through the loop coupler 115. This is but one example and the reader may note there are many ways to prevent an object such as the first fastening means 110 from passing back through the loop coupler 115. The handle 130 may similarly act as the optional stop mechanism.

FIG. 1B shows an exploded view of the preferred embodiment for illustrating more clearly all components and features, and their connections to each other. While the outer belt material 102 and inner belt material 101 are shown to have the inflatable chambers 103 and chamber connecting tubes 124 built into them, the reader shall note that these lines are simply for illustration purposes so it is more clearly what the chamber pattern looks like. In reality, the two materials are flat sheets of fabric as stated above that are connected together via a suitable process. The applicant's preferred method of connecting the two flat sheets together is RF welding, and a die is created such that it welds the inner belt material 101 to the outer belt material 102 to create the seam profile as shown in the internal pattern depicting the inflatable chambers 103 with a single welding operation. Optional cutout reliefs 132 are further depicted, and while inflatable belts 100 were built without such features and demonstrated to function fine, particularly around the legs, feedback showed that such features may be useful in allowing better contouring and more efficient radial compression, particularly around the arm. Such cutout reliefs 132 may be on only one, or both fabric materials, and if the inner belt material 101 is elastic fabric for example, use of cutout reliefs may not be necessary as the fabric is itself conforming and stretchy. The input port 104 is depicted as a right angle connection, but may be perpendicular as well for insertion of a belt valve 107 (shown in FIG. 1H). The input port 104 is preferably placed close to the loop coupler 115, but not limited to such location as shown in FIG. 1B. The loop coupler 115 may be connected through a loop formed by the outer belt material 102. There is a hole in the outer belt material 102 to allow a gas to flow through the input port 104 and into the inflatable chambers 103. Only one input port 104 is shown, however the reader shall recognize that in lieu of chamber connecting tubes 124, multiple input ports 104 may be used to inflate various sections of chambers.

Two sections of first fastening means 110 are depicted for the reasons described below. However the reader shall recognize that such pieces may be combined into a single component. The wider and shorter first fastening means 110 is preferably, but not limited to, an adhesive backed loop fastener. The adhesive backing facilitates in assembly of the overall inflatable belt 100 as it holds the first fastening means 110 onto the outer belt material 102 during sewing to make alignment through the machine easier. In the case of welding, the adhesive backing may be a thermoplastic coating suitable for RF welding or ultrasonic welding. The width of the shorter and wider first fastening means 110 is preferably equal to the width of either the outer belt material 102 or the inner belt material 101, to make the final sewing step lock together all necessary components as described below. Alternatively the width of both sections of first fastening means 110 may be equal. As previously described the width of the shorter wider first fastening means 110 may preferably range from 1.75 in to 3.5 in—depending on whether the inflatable belt 100 is of an arm or leg—but is not limited to these dimensions and may range from 2 cm-20 cm in width. The longer narrower first fastening means 110 is preferably, but not limited to, a loop fastener that has fabric loop on both sides, giving a soft, finished feel to the piece. This "double loop" component may only have loop on the top surface as well, as typically seen in standard loop fastener. The width of the longer narrower first fastening means 110 is preferably a standard width to pass through a standard loop coupler 115, but may be the same width as the inflatable belt 100 allowing the first fastening means 110 to be made of a single piece of material. For example, in FIG. 1B, the width of the wider first fastening means 110 may be 2.25" and the width of the narrower first fastening means 110 may be 1.5" to match a 1.5" loop coupler 115. The two sections of first fastening means 110 may be connected together via means known in the art such, but not limited to, ultrasonic welding, or stitching. The opposite end of the longer first fastening means 110 may be coupled to an optional handle 130. The handle 130 may assist in pulling tight or ripping off the inflatable belt 100 from the limb 90. In this preferred embodiment, the handle 130 is trapped inside a loop formed by wrapping the first fastening means 110 back onto itself and fastening via means known in the art as previously described, but the handle 130 may also be sewn directly to the first fastening means 110 or second fastening means 111. Properties of the handle 130 have been previously described.

A small section of second fastening means 111, preferably but not limited to, hook fastener, may then be affixed to the top surface of the first fastening means 110 next to the loop in the first fastening means 110 that secures the handle 130. Only a small section of second fastening means 111 is necessary, in this embodiment approximately 5 cm in length and width. Different levels of aggressiveness in the hook component were tested and the optimal style is one that is strong in shear but weak in peel.

The two first fastening means 110, handle 130, and second fastening means 111 may be formed as one assembly, and then, using the preferred adhesive backing of the shorter first fastening means 110, stuck down to the assembly of the outer belt material 102, inner belt material 101, input port 104, and loop coupler 115, in preparation for sewing. Alternatively all layers may be RF welded together, or bonded together in a single operation as described in prior art occlusive cuffs. If an optional body interfacing component 200 is used, it may similarly be adhered or welded at this time to the underside of the belt fabrics, for example with glue or tape, such that it too remains in place when pushed through a sewing machine. The edge of the shorter first fastening means 110 where the longer first fastening means 110 as attached, forms the start of the overlap length 139 and may therefore be inset from the end of the inflatable length 133 as shown in FIG. 1C and previously described and according to the dimensions previously mentioned as being optimal.

The final step is to bind the edges with a binding tape or edging 131 that may be inelastic, but is preferably soft and elastic. This edging 131 is what contacts the user's skin and so a soft cushy material, such as used on the sleeves of a fleece jacket is an ideal material. The edging 131 is applied via suitable means, but preferably stitching in this embodiment, and this stitching operation captures both the belt fastening means 105 (not explicitly labeled but described as a combination of first fastening means 110 and second fastening means 111) and the inflatable chamber 103 assembly, and the optional body interfacing component 200 (not shown in FIG. 1B), into a final assembly with a single, fast, simple, stitching operation. In this manner the full inflatable belt 100 assembly may be easily and simply assembled to keep costs low and allow high volume manufacturing, which Sato says is a key toward mass adoption, yet counter to the design of current KAATSU belts. As previously stated, with proper coatings, the assembly of FIG. 1B may be created with a single welding operation as well.

The applicant wishes to point out again that there are several factors that contribute to the ultimate goal of taking an inflatable belt 100 around a limb in an open position, inflating it to initially compress the limb to a closed position, and providing elasticity for the limb to expand, and the belt similar to expand to a working position, all the while maintaining compressive force and restriction of venous return of blood to the heart. The reader shall note that the open, closed, and working positions described are for reference comparisons only and, where ranges are given, for example for limb circumferences, the open, closed, and working position may constitute the median value of such range.

Preferred Embodiment—Operation. The inflatable belt 100 of FIG. 1A is applied as follows in conjunction with a BFR system. First, a user (not shown) selects an appropriate size of inflatable belt 100 based on their upper arm girth if exercising the upper limbs, or upper thigh girth if exercising the lower limbs. If a body interfacing component 200 is provided, and if the body interfacing component 200 is detachable, the steps to get set up shall be substantially similar to those described in the previously filed provisional application referenced herein.

Next, the user takes the inflatable belt 100, which may be held in loop form, but is not necessarily so, and slips it over their arm or leg into the desired position as described in Sato and referenced herein to form a position as shown in FIG. 1E. Then the user takes the handle 130 (not shown in FIG. 1E) and pulls it until the desired tension is reached, which may be dictated by the body interfacing component 200, if provided. The user then fastens the second fastening means 111, which may be hook fastener, to the first fastening means 110, which may be loop fastener, to secure a starting outer circumference of the inflatable belt 100 around the limb 90 as shown in FIG. 1E, and this position known as the open position when wrapped around a limb. If no additional optional elastic members are provided at some point along the circumference, this starting circumference in the open position forms substantially the maximum circumference of the belt. The inflatable chambers 103 encompass enough of the limb 90 as to provide the proper targeted compression. As shown in FIG. 1F, if the limb 90 is small enough, the inflatable chambers 103 may overlap themselves up to an overlap length 139 represented by E.

In applying the belt to the open position on a limb, as the user starts to pull the handle 130, if provided, the side of the inflatable belt 100 opposite the loop coupler 115, first comes in contact with the user's skin or clothing. As preferred, the optional body interfacing component 200 is employed with friction surface 201 facing inward and the friction surface contacts the user's skin or clothing. Because of the high frictional coefficient, the body interfacing component 200 grabs the surface and resists rotation, allowing the user to pull the inflatable belt 100, reasonably snug into the open position. Should the inflatable belt 100 require a high initial tension, as in the case of KAATSU equipment, the rotational force would likely overcome the frictional force resisting rotation and the inflatable belt 100 could spin in an undesirable manner. This of course applies to putting the band on oneself, as only one hand can easily reach the inflatable belt 100. Because the optional body interfacing component 200 is spacing the inflatable chambers 103 sufficiently off the limb's surface, thereby providing significant volume increase for the inflatable chambers 103 to expand into, a lower initial tension just to keep the band in place is all that is required and thus rotation is not a problem. The reader shall note that the body interfacing component 200 is an optional piece and the applicant's invention may function just as well without it depending on the initial tension requirements of the user 90.

For each size of inflatable length 133, there may be an optional overlap length 139, as shown in FIG. 1E, to allow users with limb girths smaller than the inflatable length 133 to use the inflatable belt 100, and thus reduce the number of sizes needed. In the case where the user's limb girth is smaller than the inflatable length 133, the inflatable belt 100 is wrapped around the limb, and as the two ends of the inflatable length 133 approach each other, the overlap length 139 separates from the first fastening means 110, and moves under the loop coupler 115, passing the loop coupler 115, and resting under the opposite end of the inflatable length 133 as shown in FIGS. 1E,1F and FIG. 5. As the inflatable belt 100 is inflated (described below), as shown in FIG. 1F, the portion of the inflatable length 133 covering the overlap length 139, holds the overlap length 139 in place from pushing out to one side, via radial pressure and the friction surface 201 on the body interfacing component 200, if provided. This aspect ensures that radial compression is translated to the limb, even in the case of these overlapping conditions. The reader shall note that other belt constructions as described in the prior art may be adapted to employ the applicant's invention instead of using limiter plates or other complicated construction. For example, the straight belt described in U.S. Pat. No. 8,992,397 to Sato could be adapted to implement the applicant's invention to use the inflatable chambers concept to shrink the belt length in order to apply compression instead of the elastic materials and limiter plates he describes. Additionally, the overlap length 139 could be eliminated and the first fastening means 110 connected directly to one end of the inflatable chambers 103. The reader shall understand that many such configurations and geometries are possible and shall be considered within the scope of this invention.

This ends the most basic description of the method of operation of the inflatable belt 100, which includes the construction of an inflatable belt, positioning the inflatable belt on the user, and preparation of the inflatable belt for inflation. For completeness, the full blood flow restriction system 116 operation will further be discussed in this preferred embodiment as related to system embodiments depicted in FIG. 1H.

The previously filed provisional application referenced herein, discusses a myriad of combinations of valves and compressors, and manual vs. automated inflation. All such variations and combinations shall be applicable to this disclosed invention and for the sake of brevity, the only system configuration discussed will be that of a manual inflation means 106, an adjustable release valve 118, a pressure gauge 138, a gas hose 119, and belt valve 107 and a valve coupling 120. The belt valve 107 may employ a gas flow shutoff means 108 (not shown) as described in the referenced provisional application.

Gas, preferably air, is injected into the inflatable chambers 103 by inflation means 106 until a desired pressure is reached as read from the pressure gauge 138, transforming the inflatable belt 100 from FIG. 1E to FIG. 1F. In place of a pressure gauge 138, a pressure limiting valve 117 (as shown in the previously filed application) may provide an upper pressure limit, and the pressure limiting valve 117 may release air until the pressure has dropped such that the pressure limiting valve 117 resets and seals the opening. Such check-style, or pop-off, valves are well known in the industry and any such method or means for accomplishing pressure limiting may be considered within this scope. The pressure limiting valve 117 may be easily swappable, allowing for quick replacement for different users, or may be permanently connected, or may itself be adjustable, with or without markings to indicate the relief pressure setting. An advantage of the pressure limiting valve 117 may be that the user does not need to think or try and precisely inflate the bands, but can just pump the manual inflation means 106 until the pressure limiting valve 117 activates, further simplifying use. Finally, an electromechanical pressure control system such described in the referenced provisional application may be used to serve a similar function to the pressure limiting valve 117.

Once the desired pressure is achieved in the inflatable belt 100, the valve coupling 120 may be disconnected from the belt valve 107 and the user is free to move around and do various exercises without additional equipment attached that adds weight, bulk, and encumbers movement. The reader shall note that a more complicated electromechanical monitoring system as described in the prior art could also be used in conjunction with the applicant's belt design without departing from the spirit of this invention for a blood flow restriction training system.

When the user is through with the desired exercises, the user may release the pressure in the inflatable chambers 103 and deflate the inflatable belt 100 to a low tension on the arm. The user then removes second fastening means 111 and pulls the inflatable belt 100, still preferably kept in loop form, off of their limb. The user may then remove the body interfacing component 200, if the component is configured to be removable, and may wash it, or replace it with another component for a next user.

This general procedure illustrates the full process of how the system is used, however there are some very novel and counter-intuitive features to explain. It has been stated previously that the construction of the inflatable belt 100, where the inflation is created with a series of inflatable chambers 103 linked side by side, as opposed to end to end, each having a height 122 greater than a width 123, will shrink in length when inflated. Typically objects expand outward under inflation as in Sato's patents, or other generic occlusive cuffs or blood pressure cuffs, and thus necessitate stiffeners or constructions serving an equivalent purpose. FIG. 1D illustrates how the shrinking is achieved. FIG. 1D shows the portion of the inflatable belt 100, formed by the outer belt material 102 and the inner belt material 101, which in turn form inflatable chambers 103, with chamber connecting tubes 124 disposed between each of the chambers to allow an airflow 109 to pass from chamber to chamber. The belt starts at an open position with each inflatable chamber 103 at a deflated width represented by H, the chamber deflated width 137. The reader shall note that the open position simply refers to the deflated state and may be with the belt flat, as described below to explain the shrinking effect, or wrapped around the limb of the user. The reader shall note that while FIG. 1D shows a slightly inflated chamber, this is for illustration purposes only to make it clear that the chamber is in fact present, but in reality, this chamber deflated width 137 may be completely flat and void of any significant amount of gas. This chamber deflated width 137, multiplied by 2, because there are two sides, one from the outer belt material 102, and one from the inner belt material 101, forms the maximum circumference of the inflatable chamber 103 when it inflates into a cylinder (assuming the two materials are substantially inelastic as preferably described). When the inflatable chambers 103 are inflated with a gas, they turn cylindrical—except at each end as previously discussed—and this chamber deflated width 137, turns into the chamber inflated diameter 136, represented by G. This inflated, shrunken state is the closed position of the inflatable belt 100, and the reader shall note that the closed position as described herein represents the inflated state of the belt, preferably when the pressure source is disconnected and the belt encapsulates a certain amount of gas, whether the belt is lying flat or applied around the limb of a user. In the case where the belt is wrapped around a limb of the user, the closed position is the inflated position that is desired sufficient to restrict the desired amount of blood flow around a limb size at the median of the designed size range of the belt and represents substantially the smallest circumference the belt reaches during a single use. As described below, the reader shall note that while FIG. 1D shows the chambers in a fully round position, the closed position may actually be somewhere between a flat and fully round, or pillow-shaped state depending on the initial tension when applied to the user, or the geometry of the chamber when lain flat. Geometry tells us that the diameter G is related to the circumference by the equation Pi*G=circumference. The circumference is related to the chamber deflated width by circumference=2*H. This the relationship of H/G, and subsequent decrease in length, shown as the shrinkage factor 135, represented in part by F, is thus Pi/2 or ~1.57, meaning for each inflatable chamber 103 of width 123, or similarly chamber deflated width 137, the inflatable chamber width will shrink by up to 36% when fully inflated (as width is transformed into diameter) as shown in FIG. 1D represented by G. As the width 123 is aligned with the inflatable length 133 of the belt, the inflatable length 133 may similarly shrink by approximately 36%. Actually, each inflatable chamber 103 itself can shrink by 36% (which is 100*(1−2/Pi)), but since some amount of belt must be accounted for with the chamber connection joint 129, the applicant approximates a reasonable potential shrinkage of the full belt to be about 33%. In the case of a belt that targets a specific zone on the limb (as will be described later), or in the extreme, where a design might have many high and narrow chambers, the chamber connection joints 129 may form a large proportion of the length, and the applicant contemplates that the lower bound of usable belt shrinkage from the change in chamber dimensions would be about 5% if the belt were inflated while not on a limb. The reader shall note it is possible to approach the theoretical maximum shrinkage of 36% by thinning the chamber connection joint 129 to an infinitesimal limit, and all such variations that incorporate such shrinking more than 33% shall be considered within the scope of this invention. While chamber connection joints 129 don't change in length, in the preferred embodiment, they represent a small fraction of the inflatable length 133 and thus the inflatable length 133 can assume to shrink by about 33%, if the chambers are allowed to fully inflate. As the inflatable belt 100, which may be wrapped around a limb when in use, is inflated, the inflatable belt 100 contracts in length, radially inward on the limb, and because the circumference wants to decrease, as more gas is pumped in, the inflatable belt 100 gets tighter and tighter on the skin. The actual amount of shrinkage observed is a function of initial belt tightness and skin compliance because at some point the limb becomes incompressible and pressure ramps up inside the inflatable belt 100 without further radial shrinkage of the belt. It should be noted that the belt in normal operation is not intended to fully inflate such that maximum shrinkage is observed. The important point is the belt, using the applicant's unique construction, will contract on any amount of inflation, regardless of initial tension around the limb to apply a radially inward compressive force on the limb, both from the shrinkage of circumference as well as from the inflated inflatable chambers 103 which further depress into the portion of the limb adjacent to each chamber as shown in FIGS. 1E,1F. The chambers, when inflated, bulge inwards as they try and turn cylindrical, or pillow shaped in nature. This bulging may be accentuated on the inner face of a chamber by use of an elastic material for the inner belt material 101 as previous stated. If an elastic material is used, the material itself may expand more, and therefore grow larger in size to transfer more of the compressive force from the internal pressure to the limb, rather than the force being taken up by the wall tension of the inner belt material 101. This shrinking in length of the inflatable belt 100 is completely contrary to Sato's "hotdog" shaped bladder, or gas bag, and other prior art occlusive cuffs that will increase in length under inflation, and by extension the band, which expands in length (and width) under pressure, and thus necessitate limiter plates and the like.

To further elaborate on the physics of the belt shrinkage, FIG. 1K shows a comparison of two inflatable belts 100 with the same starting circumference in the open position, but one belt with 5 inflatable chambers 103 and one belt with 6 inflatable chambers 103. FIG. 1K illustrates the effect on adding inflatable chambers 103 and the ability to decrease the outermost circumference 703. The outermost circumference 703 represents the points on the inflatable belt 100 that can contact adjacent body parts and chafe or interfere with normal motion and mechanics. It has been previously discussed how it is important for the inflatable belt 100 to maintain a low profile on the body, thus a diminished outermost circumference 703 is highly desirable in an inflatable belt 100 for BFR training. With designs of the prior art, the outermost circumference 703 increases with pressure due to expansion of prior art bladder and gas bag designs, and thus adverse interference with adjacent body parts leads to poor mechanics of movement and discontinued use. Sato, and prior art occlusive cuffs, attempt to alleviate these effects with stiffeners or constructions that provide similar limitations on growth of the outer wall, but, as in the case of Sato, the belt is still elastic, and the stiffeners themselves allow circumferential expansion, Sato's belts grow circumferentially with increased pressure. In the case of occlusive cuffs, their intention is for surgical use and thus no consideration for dynamic movement by the user considered, while they still employ stiffeners to force inflation of the bladder inwards. On these designs, similar effects are seen as the bladders attempt to expand outward under pressure and press against the stiffener, which attempts to resist further expansion. All these prior art designs that expand when pressurized, behave opposite to the applicant's invention, which shrinks both in nominal circumference as illustrated by the reduction from the open position circumference 701 to the closed position circumference 702, and in the outermost circumference 703.

As a concrete example of this, assume chamber width 123 is 1 in. In a 5 chamber belt of FIG. 1K this produces a 5 in length. The reader shall ignore the chamber connecting joints 129, and recognize that chambers as shown will not overlap in reality, but instead will push together, but that the circles representing inflatable chambers 103 shown in FIG. 1K are depicted as pure circles for sake of visual clarity. The open position circumference 701 is then 5 in and the corresponding open position diameter Do is 1.59 in (5 in/Pi). When each inflatable chamber 103 is inflated to its maximum, the chamber inflated diameter 136 that is reached is 0.64 in for each chamber. When connecting the 5 inflatable chambers 103 together in a ring, the closed position circumference's 702 corresponding diameter is measured at 1.08 in. Therefore the closed position diameter is less than the open position diameter and the belt has shrunken in nominal diameter, and corresponding nominal circumference. In referring to the outermost circumference 703, the corresponding diameter is 1.51 in and thus is less than Do, the open position diameter. So overall, we see that not only does the nominal circumference of the belt shrink from the open position to the closed position, but the outermost circumference 703 similarly shrinks compared to the open position circumference 701.

FIG. 1K also shows the effect on an inflatable belt 103 by adding another inflatable chamber 103 while keeping the overall open position circumference 701 the same. The open position diameter Do is still 1.59 in as in the previous example. However now, the chamber inflated diameter 136 is 0.51 in. This is calculated from 5 in/6 chambers=0.8 in per chamber, and 0.8 in*2/Pi=0.51 in. The effect can be easily seen that the nominal diameter in the closed position is even smaller at 1.02 in vs 1.08 in in the 5 chamber example, and the outermost circumference 703 is similarly smaller, and measured as 1.39 in vs 1.51 in in the case of the 5 chamber example. This illustrates that effects of the belt can be accentuated by adding more inflatable chambers 103 to further reduce the nominal diameter and correlated achievable compression by the inflatable belt 100 on the limb, while simultaneously reducing the outermost circumference

703 to reduce interference with adjacent body parts and improve comfort and utility for the user.

As the inflatable chambers 103 inflate, an airflow 109 passes through the input port 104 and into the first inflatable chamber 103, but then quickly dissipates through the chamber connecting tubes 124 into the other inflatable chambers until the pressure is equalized around the limb as shown in FIG. 1F. FIG. 1F also illustrates an important property of the present invention to prevent kinking, in that the reader can see how the chamber connection joints 129 between each inflatable chamber 103 form virtual hinge joints allowing the band to fold freely around the limb 90 of the user. At no time during inflation or during exercise is an inflatable chamber 103 trying to bend or fold, which would produce a kink. The "no kinking" characteristic of this design is in direct contrast to Sato's belt which, unconstrained, inflates to a long straight tube and must be forced to conform around a limb 90, with the unavoidable consequence that the belt kinks at various points along the belt, forming potential pinch points because the inner radius of the bent chamber is less than the outer circumference. FIG. 1F also illustrates that along with the overall reduction in length of the inflatable belt 100, as explained above, radial inward compression of tissue is also achieved by expansion of the inflatable chambers 103 toward the center of the limb. Thus a twofold compression of tissue is achieved: 1) compression of skin tissue from the belt tightening around the skin as the circumference of the inflatable belt 100 shrinks during inflation, and 2) compression of skin tissue from direct expansion of each inflatable chamber 103 into limb soft tissue. During a muscle contraction, the muscle bulges and expands in size in the zone of the belt containing chambers which are inflated, and this bulging moves the inflatable belt 100 from the closed position to the working position, and correspondingly the circumference changes from the closed position circumference 702 to the working position circumference 804 as shown in FIG. 1L. The reader shall note that users come in all shapes and sizes and this bulging may be as little as 1% for those with very small arms and little muscle mass. Nonetheless, the applicant's invention is still applicable and useful for accommodating any amount of muscle contraction. The inflatable chambers 103 will, under this increased load, change shape and reduce their volume—primarily by elongating slightly in the width-wise direction, causing the belt to elongate in the circumferential direction—thereby slightly increasing the pressure in the chambers (if the volume inside the inflated portion of the belt is fixed as in being disconnected from the inflation device in this preferred embodiment), and causing the length of the inflatable belt to increase, and accommodating the muscle contraction in a spring-like fashion without a significant spike in chamber pressure or, equivalently, without significant compression on the tissue. Because air is trapped in the chambers upon disconnection of the inflation device, the pressure will increase as the belt is pushed longer by the muscle contraction, but will return to its shrunken state as the muscle relaxes, to reduce the pressure back to where forces in the inflatable belt 100 and wall tensions of the inflatable chambers 103 are in equilibrium, thus maintaining compression on the muscle. Therefore, not only has the applicant invented a compressive solution that shrinks in size when inflated, but simultaneously the applicant has created a form of radial air-spring that serves to maintain compression against the limb at a more constant pressure, while also allowing the underlying limb to increase in size without significant additional compression being added. As stated previously, the spring-like qualities of this design maintain a more even compressive force on the muscles and reduce cramping and reduce surface pressures that can lead to nerve damage as stated in the prior art.

As stated, an additional benefit of this multi-inflatable chamber 103 design is that the inflatable belt 100 itself gains increased elastic properties under inflation, and acts as a spring. Whereas in Sato's patents, the material itself must be elastic or spring-like with additional limiting plates to prevent outward expansion, the applicant's design transforms the inflatable belt itself, which may be made of inelastic material, into a spring as follows. The inflatable belt 100 starts out in an uninflated state, either flat as in FIG. 1D, or in open position 801 in FIG. 1L when wrapped around a limb. FIG. 1D and FIG. 1L illustrate the spring or elastic concept. FIG. 1D shows the inflated state when laid flat, also referred to as the closed position and depicted as closed position 802 in FIG. 1L, when wrapped around a limb, which shows the inflatable chambers 103 in a fully round state for illustration purposes. In reality, when a user initially places the inflatable belt 100 around their limb, their limb will resist the inflation of the chambers and therefore, the fully rounded state as shown is hardly ever achieved, but merely drawn as such to illustrate the principles of the invention clearly to the user. If the initial tension around the limb is very tight such that the limb can't compress much before sufficient blood flow restriction is achieved, the inflatable chambers 103 may only slightly bulge before sufficient restriction of blood flow is attained for example. Therefore, while FIGS. 1D, 1L show inflatable chambers 103 that are in the fully rounded shape, the reader shall note that the closed position may actually be achieved at a state where the chambers are between a flat position and a fully rounded, or pillow shape position as shown in FIG. 1M due to the edge effects discussed later. In FIG. 1D, as the two ends are pulled apart, the inflatable chambers 103 will start to flatten out and revert back to their deflated state as shown in FIG. 1E and FIG. 1L, increasing both the air pressure slightly in the chambers and increasing the circumferential tensile membrane stress in the air-tight fabric material by flattening the curvature which must resist the internal air pressure. This same behavior will happen during use, for example during muscle contractions as shown in FIG. 1L where the muscle is expanding and trying to pull the inflatable belt 100 apart, and transforming the belt from the closed position 802 to a working position 803, which desires a larger circumference, the working position circumference 804, due to the underlying contracted muscle which is now larger. This flattening out, allows the overall length of the inflatable belt 100 to expand as shown in FIG. 1L, therefore under muscle contraction, and thus reduces pressure spikes, and pressure on the muscle, as would be seen with a stiff chord, or stiff elastic belt as described in Sato et al. When the muscle relaxes, the inflatable chambers 103 revert back to their more cylindrical shape in the closed position 802 as shown in FIG. 1L, and equilibrium is restored, thus transforming from a working position 803 back to the closed position 802. Thus, the inflatable belt 100, allows increasing and decreasing of its length under muscle contraction, and does so without requiring any form of elastic material or spring-like elements, saving cost, complexity, and reliability via cycling of a belt spring over time. A further benefit of this spring-like action is that the overall profile of the inflatable belt 100 off the limb surface is much lower in the applicant's design than in Sato's. As the muscle contracts, the profile actually shrinks as the belt expands from the muscle contraction, meaning that in an activity such as running, there is less interference with the other parts of the body, and better mechanics are maintained. Being low profile provides a better experience, better adherence, and more proper form than a belt that stands far off the surface. This is particularly important between the legs and between the chest and arm. The inflatable belt 100 is preferably oriented so that the input port 104 is facing forward, on the bicep, and pointed in toward the body. Thus as the handle 130 is pulled back, the overlapping section moves to the outer surface of the arm and away from the body. Similar orientation is recommended on the legs with the input port 104 resting over the outer section of the quadriceps, so that as the handle 130 is pulled back the belt overlaps to the outer surface of the leg and avoids interference between the legs. The ranges of limb circumferences that can be accommodated are similarly chosen, such that there is minimal chance of interference from overlapping and the inflatable belt 100 can remain low profile in locations where it is important. The reader shall note that these preferred orientations may be changed, or the inflatable belt 100 placed in a different orientation on the user without departing from the inventive concepts disclosed herein.

The dimensions of the inflatable chambers 103 have been mentioned above and shown in FIG. 1B, and it is important to understand the various design aspects in choosing how to arrive at these numbers. For example, if the width 123 of the inflatable chamber 103, when not inflated, were to be equal to the height 122, when not inflated, the inflatable chamber 103 will not shrink much along the width 123 as desired; it will instead resemble an inflated pillow with flaring out of the edges and pinching in at the middle of each side. This will not significantly impact the overall length of the inflatable belt 100 as needed for the present invention to work.

To expand, a true circular cylinder is a three dimensional structure comprised of two flat circular end plates and a lateral surface that unfolds to a flat rectangle. This 3D structure cannot be fabricated exactly from two flat sheets bonded together as described in this application. However, a long flat rectangle formed by bonding two sheets together when inflated, will form a true right circular cylinder in the middle region of the long side but the ends will be squished—the distortion extending about ½ to one diameter in length down the cylinder on each end. The center region of this tube behaves like a true cylinder; the ends don't. Thus, the longer the cylinder, the less impact the ends have. The aspect ratio of a cylinder is defined as the ratio of length to diameter.

Therefore the height 122 must be larger than the width 123, and the greater the difference, the stronger the contraction force will be. However, should the width 123 become too narrow, there will be a large number of inflatable chambers 103, and their magnitude relative to the length of the chamber connection joint 129 will start to diminish significantly to the point where a significant portion of the inflatable length 133 is made up of chamber connection joints 129. This construction is undesirable because the goal of the design is to produce the largest shrinkage factor 135 and the chamber connecting joints 129 don't shrink. Also, the cylinders will be too small to penetrate sufficiently into the soft tissue. Further, the height 122 is also limited by the fact that the inflated cylinder, which spans approximately the width of the inflatable belt 100, cannot cover too much of the muscles, or it will interfere with muscle movement, thus the maximum height is also limited for a given target limb length and girth. Taking all these factors into account, experiments have yielded the recommended ranges mentioned in the preferred embodiment. The reader shall note that it is possible to deviate from these ranges without departing from the spirit and scope of this invention, but that doing so may create a sub-optimal construction.

The reader shall further note that in reference to the two methods of compression going on in the preferred embodiment, the bulging may be accentuated by making the inner belt material 101 out of elastic material, for example urethane coated stretch fabric, thus allowing the inner surface to expand radially inward more for a given construction than an inelastic material. There will be some spring factor generated, the exact amount of which is determined by the material properties of inner belt material 101 and outer belt material 102 and the difference in their elastic properties. The reader shall note that the author contemplates the ability to mix and match materials to achieve a variety of different combined "compression factors", comprised of the compression due to shrink in circumference when inflated plus compression due to pressure from the chambers on the adjacent portion of the limb when inflated.

The optional cutout relief 132 can perform a useful function in assisting in the contraction and expansion, and springiness of the inflatable belt 100 by reducing the end or edge effects described above. The cutout relief 132 reduces the amount of material on the edges so that as the inflatable belt 100 is pulled flatter under tension, most of the force goes to flattening the inflatable chamber 103 rather than pulling the non-inflatable edge portion flat. This results in the fact that for a given force, more expansion is achieved in the inflatable belt 100. This feature is accentuated in the configuration where the inner belt material 101 is elastic, and experiments showed that adding cutout reliefs 132 in that configuration contributed to significantly more expansion and much better efficacy, and lower pressure spikes. The cutout relief 132 may also serve an important function in contouring the muscle being compressed as shown in FIG. 1G. Slits are used for the cutouts, but it is easy to see how the non-inflated edges of the inner belt material 101 and outer belt material 102, are allowed to curl up along the slope of the muscle where the circumference of that section is larger than the circumference where the inflatable chambers 103 are located. The flexibility avoids impingement, restriction, and chafing of the muscle, which has been shown to be an issue with users of small, short limbs, particularly on the arms, and is similarly discussed as a problem in the prior art. While edging 131 is not shown in FIG. 1G, if edging were used, it would ideally (but required) be elastic to similarly stretch and accommodate the expansion of the adjacent muscle. Similarly, the stitching described in the construction of the inflatable belt 100 for locking together the fastening means and the inflatable section, may ideally be an elastic stitch, such as a zig zag or overlock stitch. Alternatively, components may be bonded together with RF welding or other fastening means as described in the prior art for occlusive cuffs and blood pressure cuffs.

Alternate Embodiment—#1. FIGS. 1I-1,2,3 show a modified version of the preferred embodiment for an inflatable belt 100 that has clusters of inflatable chambers 103 placed strategically radially adjacent to target compression zones 127 and strategically avoiding compression relief zones 128. The target compression zone 127 is ideally at least 30% of the full circumference and placed over a portion of the limb where the deep venous system may optimally be accessed and compressed as shown in FIG. 1I-2 for the arm and leg. The length of the gas bladder in such a configuration may therefore be the girth of the smallest limb that is desired to be compressed, thereby covering 100% of that person, and covering up to 30% of the girth of a user who has a limb girth of 333% of the smaller limb girth, giving a substantial range of limb girths. The targeting inflatable belt 100 of FIGS. 1I-1,2,3 is applied in a circumferential position to the limb such that there is optimal coverage of the target compression zone 127 over the deep veins, in order that the tissue compressed during inflation, displaces radially inward, and cause compression of the deep veins. On the arms, this is position is on the inner medial surface and on the legs, this position is on the inner medial surface in the groin region, slightly rotated toward the thigh as shown in FIG. 1I-2. The compression relief zone 128 is preferably located over the outer medial surface of the arm and on the outer medial surface and over the hip flexor muscle on the legs. By creating a relief space in these areas, the muscles that move perpendicular to, and underneath, the inflatable belt 100, in particular the hip flexor muscle during raising of the knee in running or "high knee" exercises, avoid a hard, pointed, compression feeling from the inflatable chamber 103, which can get quite rigid when inflated with substantial air. Thus, overall comfort is improved while maintaining the effective levels of BFR.

FIG. 1I-3 is another example of a targeting inflatable belt 100, designed specifically for the leg. This version was designed and tested to demonstrate a couple key aspects of the physics of what is happening with the compression levels. It has been previously discussed that wider bands require less pressures to cause a given level of venous restriction, and it has been reported that user's wearing blood pressure cuffs report higher levels of comfort than with KAATSU equipment. What is known is that blood pressure cuffs are much wider, but also use much lower pressures than KAATSU equipment because of the previous effect discussed of cuff width on tissue displacement and degree of restriction. However, the applicant has tried a blood pressure cuff, and while the static comfort may be higher, the wide cuff compresses so much muscle, is totally inelastic, and therefore the muscle has nowhere to go and to try a movement, like running, is impossible. The applicant therefore has invented a concept of a wider targeting inflatable belt 100 with a gas-filled, non-rectangular, inflatable chamber 103, over non-rectangular target compression zone 127, shown by the diamond shaped profile in FIG. 1I-3, and compression relief zones 128 on either side of the target compression zone 127. The target compression zone 127 under the inflatable chamber 103 is meant to cover the inner groin area of the leg at the widest part, and tapers down to a thinner width as the targeting inflatable belt 100 is wrapped around the leg. The target compression zone 127, ends prior to overlapping the hip flexor muscle which resides underneath the compression relief zone 128. Hook and loop fasteners are employed as first fastening means 110 and second fastening means 111 respectively in a fold-back style for application to the user's leg. Because of the contour of the leg, dual fastening means are used so that they may separate and contour better to the conical surface of the leg than a single fastening means which would apply uneven tension and be loose on the bottom edge where the leg circumference is less. Spring elements 114, in the form of stretch fabric, are employed between the loop couplers 115 on one side and the second fastening means 111 on the opposite side. A similar targeting inflatable belt 100 employing the applicant's invention of shrinking inflatable chambers 103 is further described in another alternate embodiment related to FIG. 4.

This extension of the concept of a targeting inflation belt 100 illustrates yet another of the many configurations, combinations, and quantities of concepts and design elements invented by the applicant in designing the optimally comfortable and effective solution for a BFR belt concept. As is such, all prior discussion and concepts of spring elements, fastening means, etc., shall further apply to this embodiment.

The reasons for creating such zones has been covered extensively in the referenced provisional patent application and shall apply as well to this variation of that invention. It is worth repeating however several aspects here. First, the target compression zones 127 are particularly useful in that they allow a portion of the limb to remain uncovered by inflatable chambers 103, the compression relief zones 128, and this minimizes the inflated length 133 needed for a given range of muscle circumferences. As stated in the preferred embodiment, if the non-inflated length 134, represented by D in FIG. 1C, may be longer yet the technique still effective, this increases the range of limb circumferences that a single size may accommodate. The overall effect is a reduction in the number of sizes to cover a full population, which simplifies manufacturing and inventory requirements.

Compression relief zones 128 may further relieve high pressure points on the muscle and improve overall comfort of the product. The inflatable chambers 103 in FIG. 1I-1 may be interconnected with chamber connecting tubes 124, or may have separate input ports 104. The pattern and location of the inflatable chambers 103 may be any such pattern and easily formed via a properly designed welding die for simple fabrication.

The reader may note that while the targeting inflatable belt 100 is shown in FIGS. 1I-1,3 in a fold-back style configuration, the same concepts can be easily adapted to a straight overlap configuration.

Alternate Embodiment—#2. FIG. 1J illustrates an alternate embodiment of the same concepts as the preferred embodiment, except that there are no adjustments or fastening means provided if enough inflatable chambers 103 are used. Therefore the need for loop coupler 115, first fastening means 110, and second fastening means 111, are eliminated. This simplified concept takes advantage solely of the circumference shrinkage and inward bulging properties to put compression on the limb 90.

The inflatable belt 100 of FIG. 1J would always be in a loop form, and if made of inelastic material, the uninflated circumference of this loop limits the maximum circumference of the limb that may be inserted. As the inflatable chambers 103 are inflated with a gas, the shrinkage and bulging occur to put compression on the limb 90 as shown in FIG. 1J. Air flows through the input port 104 into the full series of interconnected inflatable chambers 103. As in other embodiments, the chambers may be separated, and each having its own input port 104. The user would slip their limb through the inflatable belt 100 and start the inflation process. The shrinkage factor is as previously described in the preferred embodiment and since the entire length around the limb 90 is made of inflatable chambers the belt may shrink by up to 33% in circumference. Thus, a significant shrinkage factor can be achieved and a user may not need to have a continuously adjustable belt, and the extra steps in fabrication and application to the user's limb, that are associated with having to make this adjustment, or the rotational problems described by Sato. A user may simply slip the limb through the opening and start pumping up as the belt shrinks to contact the skin, and then further shrinks to compress the limb to the required amount. This design provides a simple belt that is easy to make and has the distinct advantage that it requires no instructions by the user in terms of how tight to set the initial tension prior to inflation.

Figure 3A:
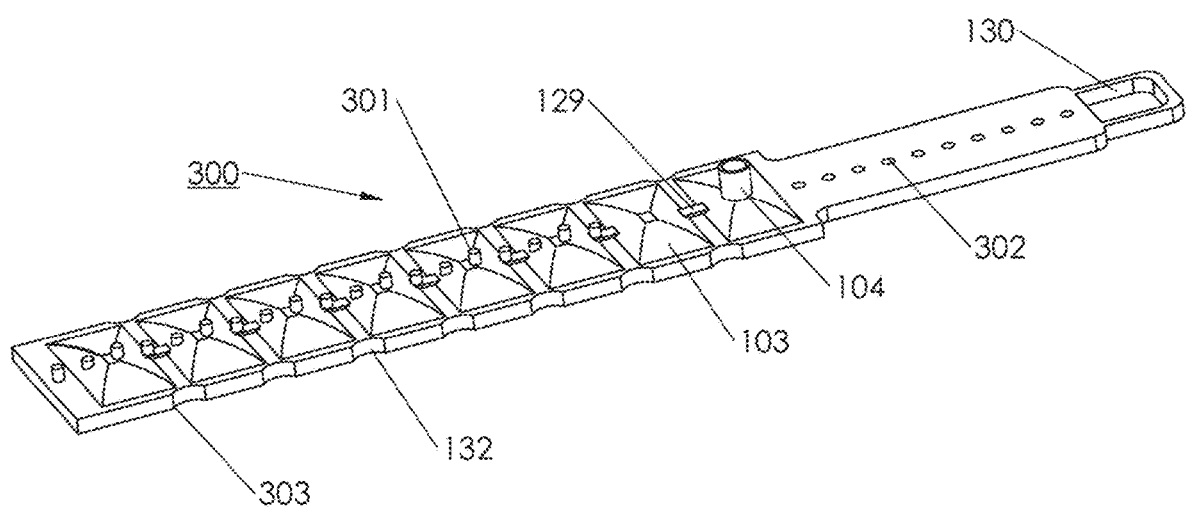
FIG. 3A—shows an inflatable belt, fabricated as a single component, with similar properties and features to that of FIG. 1A, that shrinks in length when inflated, and with locking means to fix a maximum circumference around a limb.
Figure 3B:
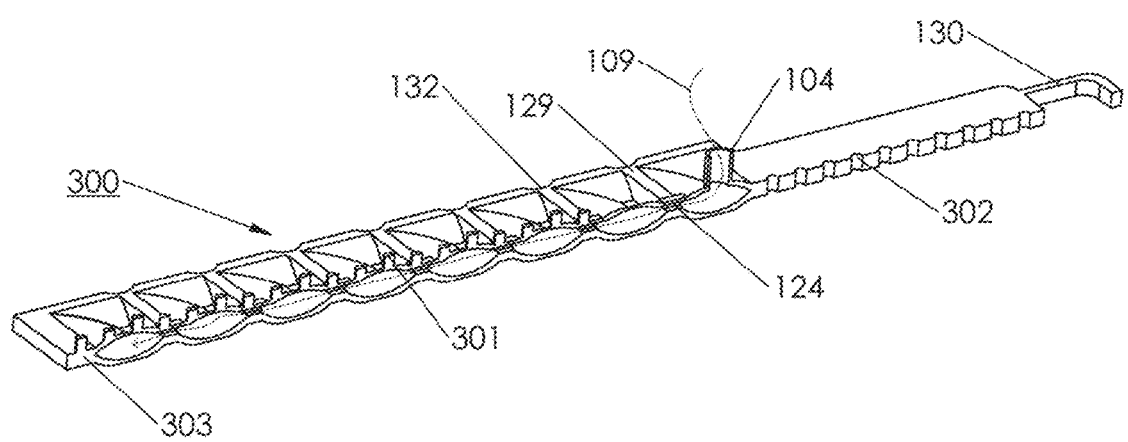
FIG. 3B—shows a section view of the inflatable belt of FIG. 3A.

Alternate Embodiment—#3A. FIGS. 3A,3B illustrate an alternate construction to the preferred embodiment via creating the inflatable belt 100 out of a single piece inflatable belt 300. The single piece body 303 may be a molded or case material such as latex rubber or polyurethane, or glass fiber reinforced rubber, to name a few materials. The elasticity, or rather inelasticity of the single piece body 303 and inflatable chamber 103 features molded in, may be controlled precisely by the thickness, dimensions, or composition of various sections of the single piece body 303, and with addition of embedded or over molded members to add structure as needed. Where stiffness may be desired, for example on the outer surface of each inflatable chamber 103, or where the distance locking holes 302 are located or in the handle 130, the thickness and/or width may be increased, or reinforcement fibers introduced into that particular section. Where flexibility may be desired, for example in the chamber connection joint 129 or on the perimeter with optional cutout reliefs 132, the thickness may be reduced to make the single piece body 303 more flexible to take advantage of the shrinking belt concept. Similarly the outer surface of the inflatable chamber 103, corresponding the outer belt material 102, may be stiffer than the inner surface, corresponding the inner belt material 101, providing larger bulging of the inner surface against the muscle. The shape, size, location, etc., of the single piece inflatable belt 300 itself, and its components such as the molded chambers may be substantially similar to the designs and features described in the preferred embodiment and elsewhere in this application. The reader shall note that many such variations and design features may be formed in to the single piece body 303, or the single piece body 303 may be formed of multiple smaller bodies that are suitably combined to create the equivalent single piece body 303. The reader may further recognize there are many variations of material type, material properties, and construction properties, such as wall thickness, that may provide certain advantages, and as long as the single piece inflatable belt 300 is configured to resist movement on the limb, and apply an adequate compression force against the limb under inflation and when restrained, all such variations may be considered within the scope of this invention.

An input port 104 may be similarly formed as part of the single piece body 303 to create this feature, or it may be attached to the single piece body 303 via any suitable method such as bonding. The input port 104 location may similarly be placed anywhere as long as it is in communication with at least one inflatable chamber 103. As in the preferred embodiment, the inflatable chambers 103 may be interconnected with chamber connecting tubes 124 or may be separate and require more than one input port 104.

A handle 130 may be formed into the single piece body 303 as stated above, and such handle 130 may be further colored or coated with reflective element 126 (not shown) to provide additional identification features as described previously.

Distance locking pegs 301 and distance locking holes 302 form the belt fastening means 105 (not called out in the Fig) equivalent to the hook and loop fastener system described in the preferred embodiment, or the other positive locking systems as discussed herein. The distance between distance locking pegs 301 may be such that sufficient granularity is achieved to accommodate a range of varying limb circumferences, but shall be initially 0.5 cm between peg centers. Such distance locking pegs 301 may further be labeled according to a prescribed setting of where to fasten the distance locking holes 302 based on the measured circumference of the limb to be inserted. Distance locking pegs 301 may similarly be replaced with other fastening means such as hook and loop fastener and the reader shall note that many such locking schemes known in the art may be employed without departing from the spirit of this invention.

Cutout reliefs 132 may be optionally formed in to the shape of the single piece body 303 and the properties of the single piece body 303 may be altered around the edges as described above. The cutout reliefs 132, if used, provide similar benefits in terms of comfort and effectiveness as described in the preferred embodiment.

Finally, the reader shall note that while the configuration shown is a straight overlap configuration, as opposed to a fold-back style as in the preferred embodiment, the single piece belt may easily employ a loop coupler 115 (not shown in FIGS. 3A,3B), or have molded features that serve this function, and fold back on itself as in the preferred embodiment. Because the single piece body 303 is shown as symmetrical about the distance locking holes 302, all that is needed is to add a loop coupler 115, or similar features in molded form, to the opposite end of the single piece body 303 via suitable means known in the art, such as sewing, bonding, trapping inside a loop at the end of the single piece body 303, etc.

Operation of the single piece inflatable belt 300 is substantially similar to that of the preferred embodiment. The belt is wrapped around a limb to the desired tightness, as may be indicated by markings on the distance locking pegs 301 corresponding to a specific limb girth. The end of the single piece body 303 with distance locking holes 302 is placed over the corresponding distance locking pegs 301 to lock the single piece body 303 in a loop form at an initial circumference. If the outer surface of the single piece inflatable belt 300 is all substantially inelastic, this initial circumference shall constitute approximately the maximum circumference of the belt. Airflow 109 is passed through the input port 104 into the inflatable chambers 103 as shown in FIG. 3B and passes from one inflatable chamber 103 to the next through the chamber connecting tubes 124. The effect on the shape of the single piece body 303 and subsequent compression on the limb 90 is substantially the same as if the single piece body 303 were made with the components shown in the preferred embodiment. Thus an equally effective BFR training system may be produced with a single molded component.

The reader shall note that one or more features of the single piece inflatable belt 300 may be separate and later attached in the manufacturing process, and any such modifications or alterations shall be considered within the scope of this invention.

Alternate Embodiment—#3B. FIGS. 7A-D shows another embodiment of a snap-on inflatable belt 1000 similar in construction to FIG. 5, but with some important differences. The snap-on inflatable belt 1000 is comprised of a snap-on belt body 1003, substantially similar in properties and constructions to the inflatable belt 100 of FIGS. 3A,3B and FIG. 4. The snap-on inflatable belt 1000 may, or may not incorporate anti-roll features (not shown for simplicity). An input port 104 is provided in substantially the same manner as described in relation to FIGS. 3A,3B and FIG. 4. The snap-on belt body 1003 further comprises a single inflatable chamber 1001 for receiving a gas, and the underside of the inflatable chamber 103 is in contact with the user's limb. The reader shall note that the construction disclosed in FIGS. 7A-D may also be adapted to take advantage of other inventions in this application such as multiple inflatable chambers 103 that produce radial contraction, or targeting features of FIG. 4 and all such adaptations shall be considered within the scope of this invention. The single inflatable chamber 1001, as applies to FIGS. 7A-D, may have a height that is comparable to the width of the body interfacing component 200, such that an initial air volume is provided to increase the total air volume available for dampening pressure spikes from muscle contraction. By one example, the single inflatable chamber 1001 height is 2 mm. The snap-on belt body 1003 further is in communication with a first fastening means 110 and second fastening means 111, wherein the first fastening means 110 and second fastening means 111 are connected once the snap-on inflatable belt 1000 is applied to the user's limb, in order to contain a specific circumference. The snap-on belt body 1003, further encompasses, and preferable has molded into it, a coil spring 1002, preferably in the form of a metal or plastic strip of spring steel with crescent profile. The principle of using a metal guide to snap the belt onto the limb provides certain advantages. All comments in relation to FIGS. 3A,3B and FIG. 4, around construction variations, optional addition of other components, variations of material type, geometry, etc. shall apply to this snap-on inflatable belt invention. Similarly, the single inflatable chamber 1001 is shown for illustration purposes as open, but in fact is hermetically sealed at both ends to trap a fixed volume of gas inside during operation and once inflated.

Figure 7A:
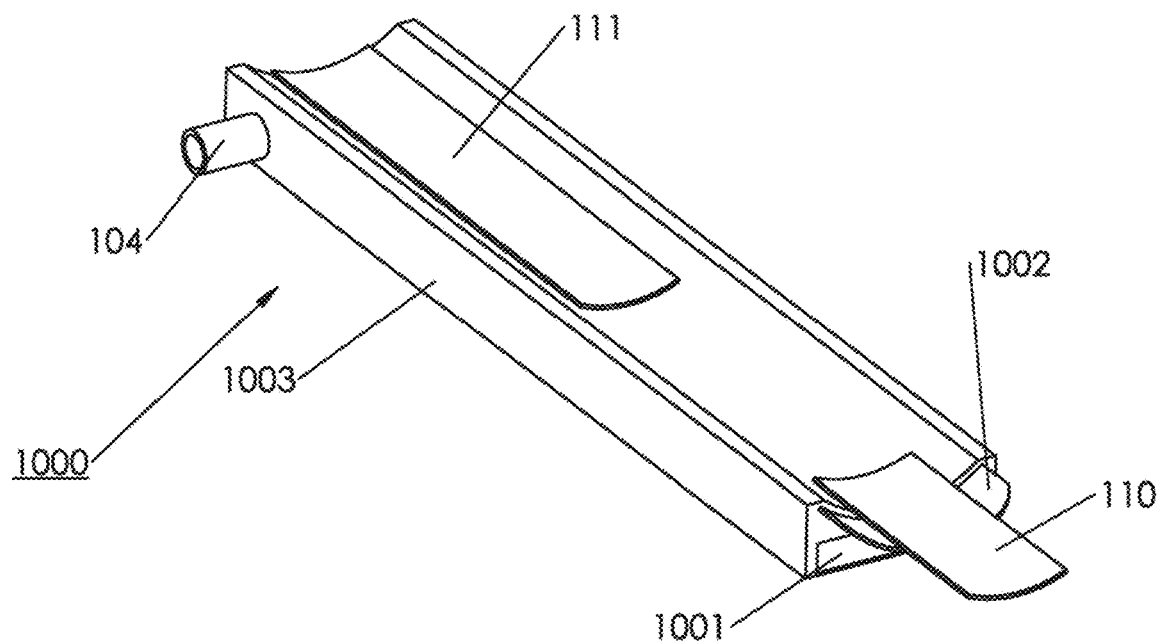
FIG. 7A—shows a molded snap bracelet style inflatable belt assembly comprised of a molded elastic bladder, further comprising an inflatable chamber, and input means for introducing a gas into the chamber, a coil spring designed to hold the belt assembly straight when uncoiled, and coil the belt assembly when snapped around a user's limb, and fastening means for securing the circumference of the belt assembly once snapped to a user's limb.
Figure 7B:
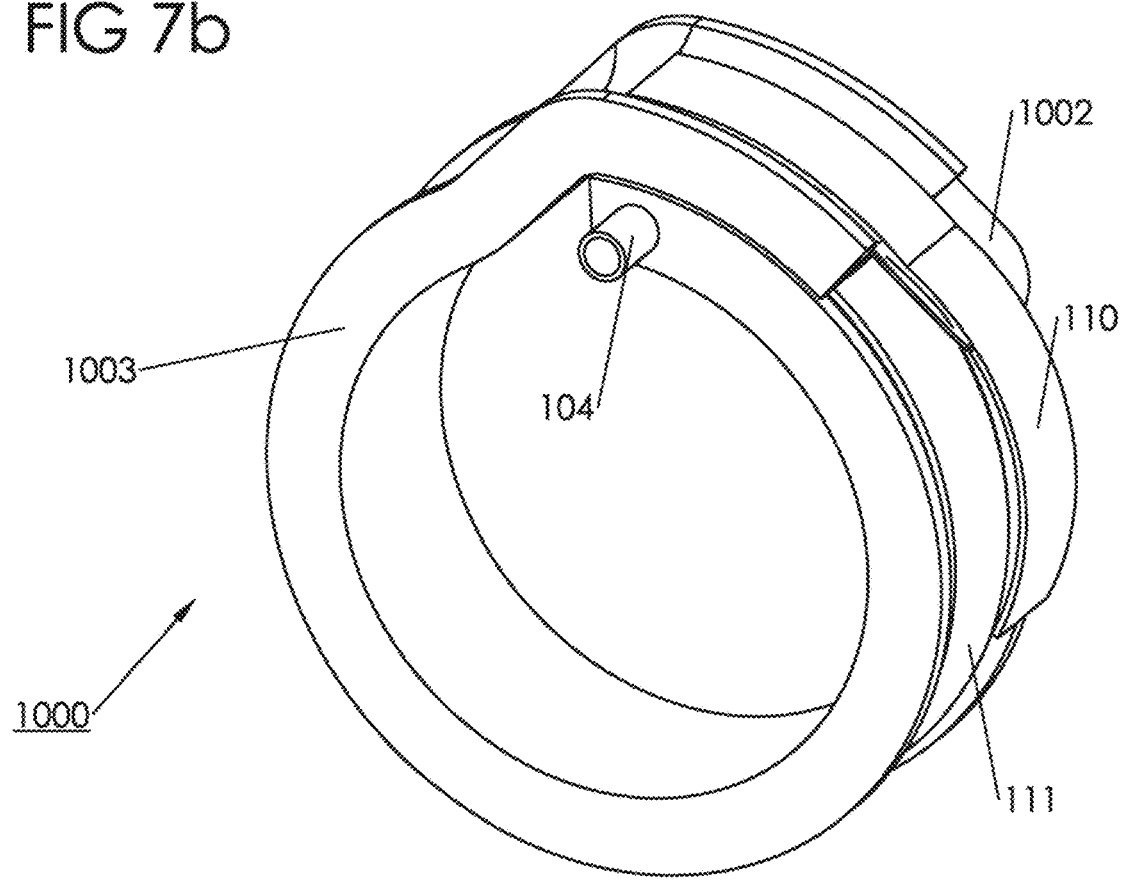
FIG. 7B—shows the belt assembly of FIG. 7A coiled as it would look when coiled around a limb.

The snap-on inflatable belt 1000 functions as follows. The user may take the belt in one hand, which is not the hand of the limb they are expecting to apply the belt to, and unroll or extend the belt into a straight position. The coil spring 1002 unravels and when held completely straight, bends slightly and forces a rigid straight piece as shown in FIG. 7A, and as all snap bracelets do. The user then moves the belt over the correct location on the limb and in the correct orientation where at least the target compression zone 127 (not shown) is covered, and forcefully lowers the belt against the limb. The belt contacts the limb, and the momentum causes the rest of the belt, distal to the connection point between the belt and the limb, to bend, and then break the straight line shape and begin to wrap around the limb as shown in FIG. 7B, starting at the connection point with the limb. The user then takes the end they were holding, which also contains first fastener means 110, and wraps this around the limb to fasten to second fastening means 111. As the snap-on belt body 1003 may be made of a material with substantially high friction coefficient, such as latex rubber, the coil spring 1002, is biasing the inflatable bladder 601 against the skin in trying to coil up, and thus providing sufficient normal force as to allow the user to even apply significant tensioning force to the belt. When the single inflatable chamber 1001 is filled with air, the belt will try to unravel, but is restrained by the fastening means. The length along the single inflatable chamber 1001 is further restrained and kept from expanding by the coil spring 1002 and fastening means, if the fastening means is not elastic. Similar comments about introduction of a belt spring, properties and locations of the fastening means, etc. apply to the embodiment of FIGS. 7A-D. As with the embodiment of FIGS. 3A,3B and FIG. 4, this invention has the benefits that it is simple and cheap to construct and apply without any, or minimal sewing operations.

Figure 7C:
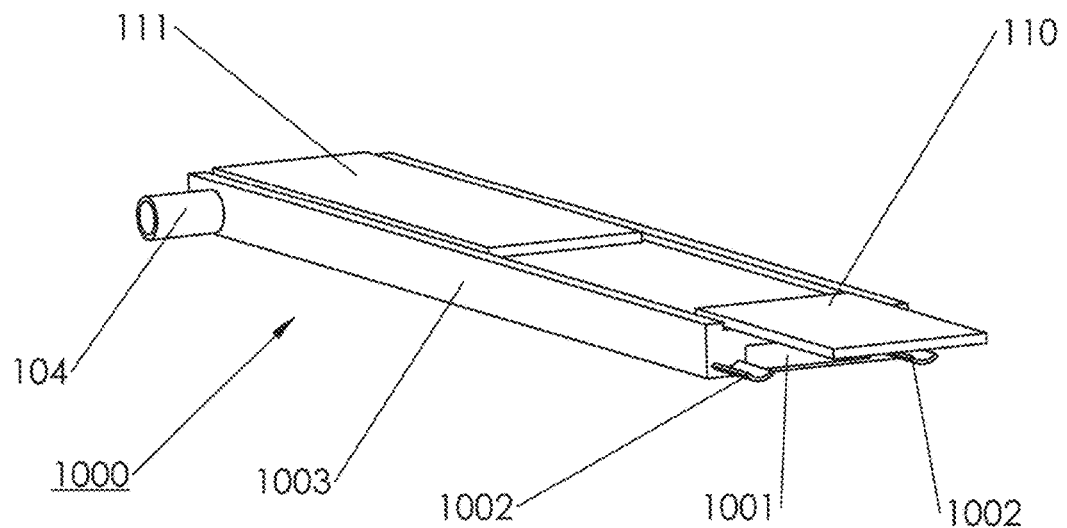
FIG. 7C—shows a variation of the belt assembly of FIG. 7A, wherein instead of residing on top of the inflatable chamber, the coils spring, or two as is illustrated, reside underneath the inflatable chamber.

FIG. 7C shows an alternate construction of a snap-on inflatable belt 1000 wherein the coil spring 1002 is separated into two coil springs 1002, and placed under the single inflatable chamber 1001 versus on top shown in FIGS. 7A,7B. The advantages of such a construction would be that the amount of kinking would be potentially less. While a body interfacing component 200 (not shown), if used, will help mitigate these issues, having less kinking is only helpful. While two such coil springs 1002 are shown, only one is absolutely needed to fulfill the requirements of this invention. FIG. 7C illustrates another configuration without the outer belt material 102 and using inelastic first fastening means 110 and inelastic second fastening means 111, and a gap there between. This gap allows circumferential stretch of the snap-on belt body 1003 itself when under inflation and trying to unravel.

In FIGS. 7A-D, the coil springs 1002 do not necessarily run the length of the snap-on inflatable belt 1000, and may stop short and be contained inside the snap-on belt body 1003. In particular, where the snap-on belt body 1003 is to be used as the spring elements 114, it may be advantageous for the coil spring 1002 to be absent from this section of the snap-on belt body 1003. For example, the coil may be absent from a short section of the snap-on belt body 1003 just to the interior side of the connection point of the first fastening means 110.

Figure 7D:
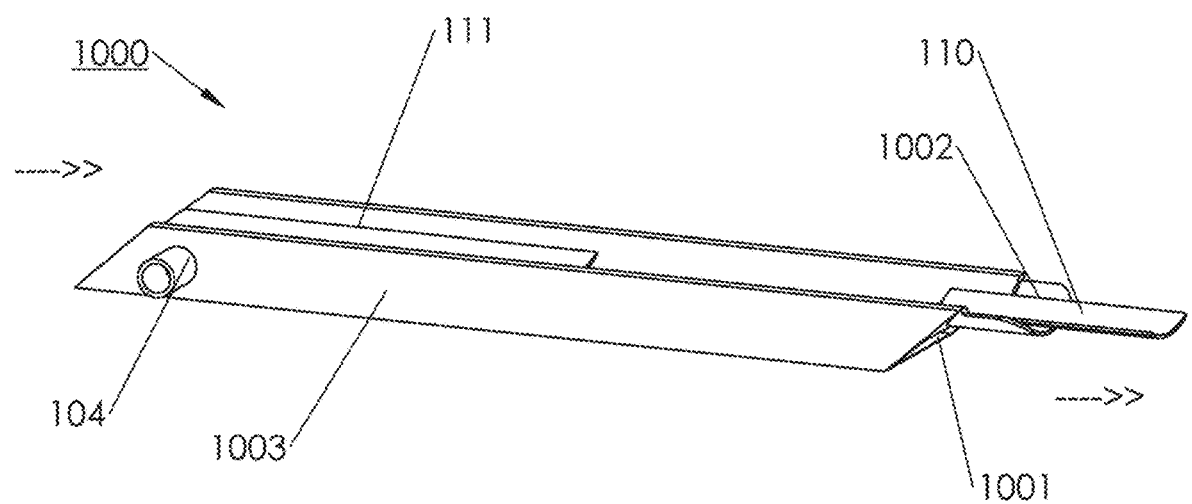
FIG. 7D—shows the intention of the belt assembly of FIG. 7A, to provide for some shear displacement in the longitudinal direction as gas is introduced to the inflatable chamber, or the muscles contract, and the coil spring wants to uncoil.

In both FIGS. 7A,7B and FIG. 7C, anti-friction padding (not shown) may be added to the top side of the snap-on belt body 1003 to help the belt slide along itself if overlapped. This small movement and expansion of the circumference during muscle contraction will add all the benefits previously described in relation to the belt spring (not shown). Alternatively, as shown in FIG. 7D, the snap-on belt body 1003 itself may shear sufficiently to provide enough relative circumferential displacement to accommodate muscle contractions adequately.

The reader may note that many advantages have been demonstrated in relation to a molded design in FIGS. 3A,B, FIG. 4, and FIGS. 7A-D such as reduction in part count, ease of application, additional locating features, etc. and that these concepts may apply to any of the molded concepts or contemplated configurations herein. The reader may further note that while the figures depict a starting state as typically in a straight fashion, the molded components may have a curl pre-molded into the shape to reduce kinking on the skin, as is analogous to adding pre-stretch into the inner belt material 101 as previously illustrated. Such "coiled" steady state further is advantageous in that the belt "self-packs" into a compact state for easy transport, which is another important benefit.

Alternate Embodiment—#4. FIG. 4 shows a targeted inflatable belt 400 formed with a single piece body 303 with substantially similar properties and features as described in a previous alternate embodiment. FIG. 4 is meant to illustrate the concept that not all inflatable chambers 103 need to be the same size and shape, and may be spaced anywhere along the length of the belt to form customized target compression zones 127 and compression relief zones 128. Larger inflatable chambers 103 may be placed over areas where significant tissue displacement is required, such as radially over the deep veins. Similarly, inflatable chambers 103 may be omitted over areas where the muscle moves under the band such as the top of the bicep or hip flexor locations. The benefits of these zones, non-rectangular shapes, and differing locations and sizes of the zones, has been extensively covered in the previous alternate embodiment discussing target compression zones 128 and target relief zones 128 and shall also apply to this alternate embodiment.

FIG. 4 shows a belt design similar to FIG. 1I-3, which depicts a belt specifically designed for the leg. FIG. 1I-3 was designed and tested to demonstrate a couple key aspects of the physics of what is happening with the compression levels. It has been extensively discussed in the prior art that wider bands require less pressures to cause a given level of venous restriction, and it has been reported that user's wearing blood pressure cuffs report higher levels of comfort than with KAATSU equipment, which is narrower. What is known is that blood pressure cuffs are much wider, but also use much lower pressures than KAATSU equipment because of the previous effect discussed of cuff width on tissue displacement and degree of restriction. However, the applicant has tried a blood pressure cuff, and while the static comfort may be higher, the wide cuff compresses so much muscle, is totally inelastic, and therefore the muscle has nowhere to go and to try a movement, like running, is impossible. The applicant therefore has invented a concept of a wider contouring belt, such as targeting inflatable belt 400 in FIG. 4, with gas-filled, inflatable chambers 103 of different sizes as shown in FIG. 4. Alternatively, non-rectangular chambers, as shown in FIG. 1I-3, over non-rectangular target compression zone 127 in FIG. 1I-3, may be formed along with compression relief zones 128 on either side of the target compression zone 127. The target compression zones 127 of FIG. 4, under the inflatable chambers 103 are meant to cover the inner groin area of the leg at the widest part, and tapers down to a thinner width as the belt is wrapped around the leg. The target compression zones 127 end prior to overlapping the hip flexor muscle which resides underneath the compression relief zone 128. Either distance locking pegs 301 can be used or hook and loop fasteners, or other suitable fastening means may be employed to secure the circumference of the belt around a user's limb. While the belt shown in FIG. 4 is a straight overlap configuration, a fold-back style may also be created for application to the user's leg. Because of the contour and conical shape of the leg, dual fastening means may alternatively be used as shown in FIG. 1I-3, so that that they may separate and contour better to the conical surface of the leg than a single fastening means which may apply uneven tension and be loose on the bottom edge where the leg circumference is less. Spring elements (not shown), in the form of stretch fabric, may be employed to add additional elasticity if required.

This extension of the concept of a targeting inflation belt 100 illustrates yet another of the many configurations, combinations, and quantities of concepts and design elements invented by the applicant in designing the optimally comfortable and effective solution for a BFR belt concept. As is such, all prior discussion and concepts of spring elements, fastening means, etc., shall further apply to this embodiment.

Figure 6:
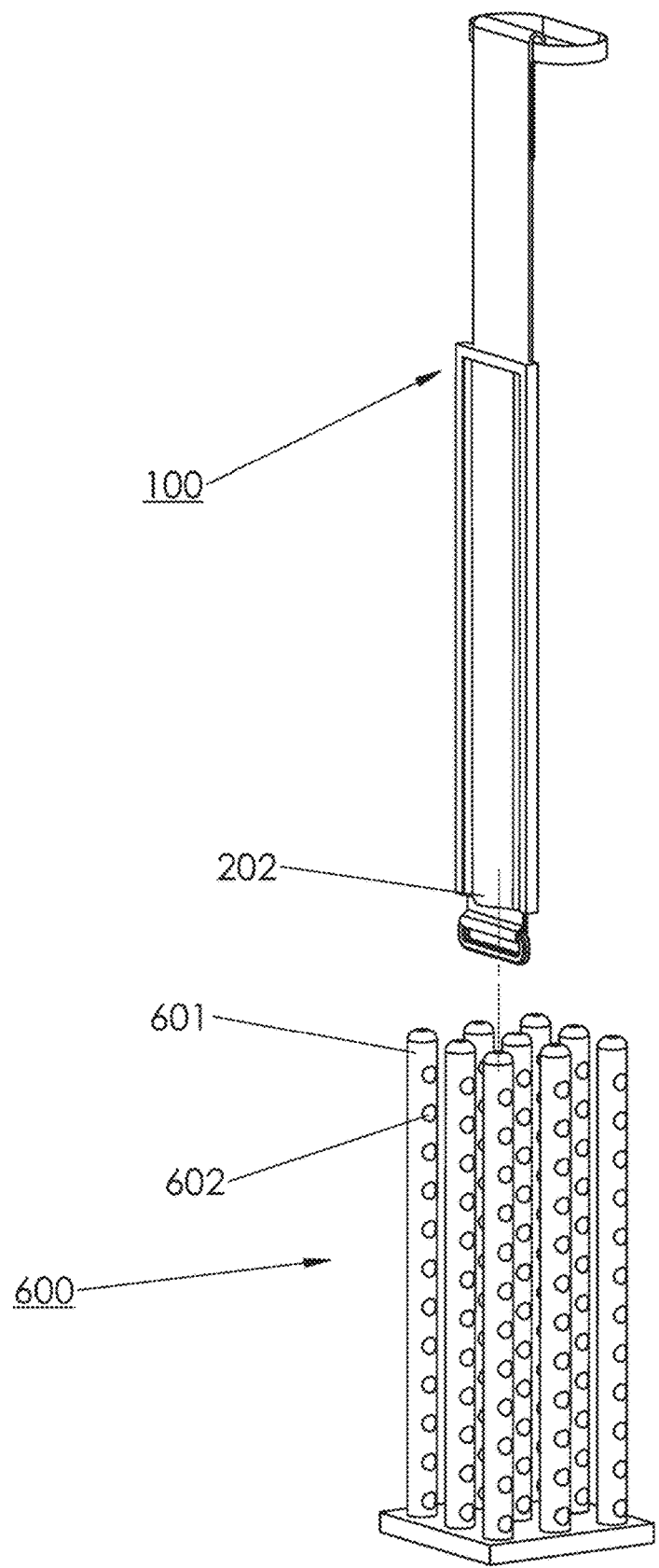
FIG. 6—shows an apparatus for storing and drying one or more inflatable belts to prevent build-up of germs and bacteria.

Alternate Embodiment—#5. FIG. 6 shows a storage apparatus 600 for storing and maintaining one or more inflatable belts 100. While the inflatable belts 100 can be hung, for example by the handle 130, should they incorporate the body interfacing component 200 as in the preferred embodiment, water and sweat can become trapped between the body interfacing component 200 and the inner belt material 101. This can lead to unsanitary conditions, accumulation of fungus and bacteria, and possible risk of infection to the user. Washing of the inflatable belts 100 is a further benefit as it helps an institution that may be using lots of belts, maintain their product in a clean and safe way. However letting the belts air dry may lead to bacteria build up, and drying them in a drier may damage the materials.

The storage apparatus 600 solves these issues with a series of posts 601, with each post 601 having venting means 602 in the form of holes for airflow as shown in FIG. 6. The posts 601 may be hollow and air may be actively pushed, via a compressor (not shown), up through the center and out the venting means 602 to actively dry in inner compartment between the body interfacing component 200 and in the inner belt material 101. The inflatable belt 100 may be placed over each post 601 such that the post is captured inside the attachment pocket 202 as shown in FIG. 6. This gentle active drying will be easy on the materials and not damage them to reduce the durability as a dryer would.

In this manner, a simple and effective storage and drying system is provided for clean, simple, and sanitary maintenance of inflatable belts 100.

Alternative Embodiment—#6. In various embodiments, a belt is provided for securing to a body segment. The belt may form a loop sized for positioning around the body segment in an open position. In various embodiments, the belt may comprise an outer belt material 102, an inner belt material 101, a plurality of inflatable chambers 103 between the outer belt material 102 and the inner belt material 101, at least one of the plurality of inflatable chambers 103 being inflatable to move the belt from the open position to a closed position, and at least one cutout relief 132 between at least two of the plurality of inflatable chambers 103. In various embodiments, the plurality of inflatable chambers 103 may comprise polygonal chambers or curved chambers. In various embodiments, the plurality of inflatable chambers 103 may be formed with substantially non-stretch material. In various embodiments, the substantially non-stretch material may be a fabric.

In various embodiments, at least one of the plurality of inflatable chambers 103 may have a movable inner wall made of substantially non-stretch material. In various embodiments, the inner belt material 101 may comprise inelastic material. In various embodiments, the belt may further comprise an input port 104 associated with at least one of the plurality of inflatable chambers 103.

In various embodiments, the belt may further comprise a means for fastening the belt. In various embodiments, the means for fastening the belt may comprise a first fastening means 110 associated with a first end of the belt and a second fastening means 111 associated with a second end of the belt. In various embodiments, the first fastening means 110 may associate with the second fastening means 111 to fasten the belt. In various embodiments, the belt may further comprise a handle 130 associated with an end of the first fastening means 110 or an end of the second fastening means 111. In various embodiments, the handle 130 may provide tension when pulled.

In various embodiments, the belt may further comprise a loop coupler 115 associated with an end of the belt.

In various embodiments, the belt may further comprise a body interfacing component 200 associated with the inner belt material 101. In various embodiments, the body interfacing component 200 may comprise a high friction surface 201. In various embodiments, the body interfacing component 200 may comprise a strip of neoprene closed-cell foam rubber.

In various embodiments, the belt may further comprise edging 131 associated with at least one outer edge of the belt.

In various embodiments, the belt may further comprise a belt spring associated with the outer belt material. In various embodiments, the belt spring may be located along a circumference of the belt under tension when the belt is in the closed position. In various embodiments, the belt spring may comprise elastic stretch webbing.

Thus the reader will see that the various inventions described herein provide an economical way to easily create a multifunctional, safe, inexpensive, easy to use blood flow restriction system 116 and inflatable belt 100 for incorporation therein. Additionally, the reader will see that the invention described herein may take advantage of current mass production processes to keep the additional cost minimal, and that by reducing component count, the applicant has not only reduced the manufacturing costs but reduced the level of complexity of operating the system, and reduced the bulk of the system which, since it is a wearable product to be used during exercise, is a significant factor as Sato himself describes.

While the above description contains specificities, these should not be construed as limitations on the scope of the invention, but rather as an exemplification of preferred embodiments thereof. Many other variations are possible.

Elasticity

Where the term elasticity is used in this specification, the reader shall note that the applicant may be referring to an elastic property of the construction, and not necessarily that the materials themselves, as individuals or when combined, have elastic properties, i.e. form a material or combinations of materials that themselves stretch in nature. The applicant acknowledges that the materials may have elastic properties themselves, but this may only be an option, not a requirement.

Similarly, the reader shall note that the applicant, when defining materials as inelastic, understands that all materials stretch to some degree when a force is applied. The applicant's description of the term 'inelastic' within the context of this application shall therefore be construed to comply with the applicant's intent and purpose for each such element within each embodiment as described. For example, a 200 denier ballistic nylon fabric, coated with polyurethane may stretch 5% when subject to a stretching force, but such material may be considered inelastic in the context of this invention when compared to prior art bladders made of rubber which may stretch up to 100% for the same given applied force.

Materials described similarly may be understood to encompass combinations of materials, varying material properties such as durometer or elastic modulus, lengths and widths, and profiles, which affect properties such as elasticity and coefficient of friction, may be considered within the scope of this invention. Further the reader may note that where a material may be discussed as elastic, a non-elastic material may be combined with an elastic material to form what would be considered the original member (or visa-versa), but which is now two components and may not specifically match the description herein. However, in such cases, the reader may note that the applicant has in fact considered that materials may be combined to perform the function of the elements of the inventions described herein, but has not made all such descriptions because of the endless possible combinations possible. All such combinations yield the same result as originally disclosed that the belt spring member has some degree of elasticity. Yet another example is the reader may note that some element properties may be altered to remove various components. For example the inflatable belt may have some degree of elasticity in order to compensate for muscle contraction. Again, the reader may note that all such combinations or omissions of components, or altering of various component properties may be considered within the scope of this invention.

Belt Shapes/Sizes

For example, in the case of inflatable belt shape, the inflatable portion of the belt may be of any suitable geometry, size and shape to provide sufficient blood flow restriction as discussed above. Belts may come in multiple lengths and widths to accommodate a range of individuals, and not necessarily minimized in the number of variations, but rather targeted toward a specific range of limb girths, or user types. It may be noted that wider cuffs have been shown to restrict flow to the same extent at lower pressures and may offer more comfort for certain applications that don't require dynamic movements. Such width variations for a specific user, such as assisting the elderly, may improve comfort while maintaining effectiveness. Belt shapes which employ enough tissue displacement to restrict venous return, such as some examples described herein, may be used, and may not necessarily cover the entire limb. All such configurations of profiles, sizes of belts, gas bladders, locations placements of such belts on the body, and bladders on belts, may be considered within the scope of this application.

Open, Closed, Working Positions

The reader shall further note that the open, closed, and working positions as defined above could also constitute the small or large end of any range or spectrum described in this specification. For example, if a belt size range is targeted at limbs of 18 cm-33 cm, the open position could be a closed circumference of any size that fits over at least an 18 cm limb up to at least a 33 cm limb. In case the specified limb is 18 cm for example, the open position may be 18 cm or slightly larger. Similarly the closed position in this case is less than the open position by some amount. The specific amount depends on a variety of factors such as the starting open position and tension on the limb, the amount of blood flow restriction desired, and the amount of pressure applied to reach the desired restriction. Similarly, the working position when wrapped around a limb entails a nominal belt circumference that is greater than the closed position nominal circumference, and less than, or up to the nominal open position circumference, thereby illustrating that the belt shrinks when moving from the open position to the closed position, and elongates when moving from the closed position to the open position. As in the example above the open position may be 18 cm in circumference, the closed position may be 16 cm in circumference, and maximum working position may be 17 cm in circumference. Or, if more compression is desired the open position may be 18 cm in circumference, the closed position 15 cm in circumference and the working position 17 cm in circumference. Therein, the reader shall understand that these terms may vary considerably depending on a specific situation and the specification and appended claims shall take into account all possible scenarios and interpreted to the broadest extent.

Combinations of Materials and Design Elements

The reader shall note that many design elements and material property combinations have been discussed and that these factors: number of inflatable chambers 103, height to width ratio of the chambers, width of the inflatable belt 100, range of limb circumferences to cover, belt material properties, cutout reliefs 132, body interfacing component 200, and targeted compression vs full encirclement of the limb, to name a few may all be combined in full or in part, altered in some way, shape, quantity or form, or otherwise modified so as to improve or alter the properties of the inflatable belt. For example, there may be as few as 1 chamber in the case of a targeting inflation belt and this chamber will contract and provide desired shrinking effects, even though it may not be as effective as having more chambers. Similarly, there may be 50 chambers for full encirclement of a large limb, and still achieve some amount of shrinkage and provide elasticity. The applicant has covered in this application, the physics, mechanical properties, and tradeoffs of these various important properties and design elements, and the reader shall understand that all such combinations and modifications of these features that affect or improve the properties and function of the inflatable belt 100 for restricting blood flow in a limb, shall be considered within the scope of this invention, and the applicant's invention shall not be limited solely to the combinations depicted in the figures or described in this specification.

Belt Materials

Various belt and blood flow restriction system designs have been described herein, and various material constructions and configurations have likewise been disclosed. Various components being elastic, and relative degrees of elasticity have further been noted. The reader may note that for the sake of brevity, not all such combinations and material types have been discussed, but all such combinations, material properties or configurations may be considered within the scope of this invention. For example, in the case of the fastening means: cam-locks, ratchets, and hook and loop fasteners have been described or referenced, however many other such means of fastening two objects together may be used such as a high friction joint triglide style mechanism, glues or adhesives, ropes or knots, mechanical hooks, buttons, racks and pinions, high friction surfaces, etc., may be considered encompassed within the term fastening means and this term interpreted as broadly as possible. Further, in the case of elastic members or fabrics, polyurethane coated fabrics may be substituted for PVC coated fabrics or a similar material, and urethane molds, but may be of latex rubber, or similar material. In all such cases where specific materials are called out, the reader may understand that this specification is but one example, and as long as the general concept described is achieved, the specific material, or specific property thereof, is not a requirement of the invention.

User

The user in the context of this application may be deemed to mean the person using the invention described. This may be a client, patient, instructor, personal user, doctor, athletic trainer, coach, etc.

General

One skilled in the art will recognize any minor modifications that would be needed for such an intermingling and such modifications may be considered within the scope of this specification and claims. Further, it may be recognized that many of the components described may be combined into a single object via different manufacturing processes such as welding, injection molding, casting, etc. While the applicant discusses some of these options briefly in the application, it may be recognized any and all combinations of the components discussed herein may be considered within the scope of this application and covered by the claims written. Similarly, it may be recognized that many components in the system and their connection points, or connection means, may also be interchanged or rearranged to achieve the same effect as the disclosed configurations. For example, where it is discussed that it may be advantageous to de-couple the inflation means from the inflatable belt, and a pressure relief valve is used to limit a maximum pressure in the belt, the pressure relief valve may reside either on the belt side of the coupling or the inflation means side of the coupling. In the case of residing on the belt side of the coupling, then no further shutoff mechanism is necessary on the belt side of the coupling. However, the invention will function substantially the same if the coupling employs a shutoff function to keep air in the belt, which is opened during connection of the inflation means, and the pressure relief valve is on the inflation means side of the coupling. In such a case, as long as the inflation means is connected, the pressure relief valve is in the same air-circuit as the belt, and limits the pressure therein. Upon disconnection however the pressure relief valve is not connected in the air-circuit of the belt, however neither is the inflation means and thus there is no risk of too high pressures accumulating in the belt. Thus the system is substantially similar in both cases. This is but one example, and in general, valves, and valve types, fastening means, such as cam locks, hook and loop fasteners, ratchet mechanisms, belt springs, inner and outer belt materials etc. may be interchanged, used in quantities of more than one, altered in width, length, or profile, employed in conjunction of overlapping belt styles, or doubling back of belt styles for locking, or more complicated belt designs such as those shown in patents to Sato, and the inventions disclosed herein may be considered to have encompassed all such permutations and combinations of such components. Yet another example is the inflatable belt may have two input ports, one to allow air in and another in communication with an outlet system such as a pressure relief valve. While such design is not shown in the figures above, the reader may note this concept is another example of how multiple items may be employed, and components shifted within the system to connect with different components, while the same overall system and effectiveness is maintained. Further still, the location and placement of various elements may be moved and altered such that they appear to differ from the figures shown, and description attached, however, all such configurations and combinations may be considered within the scope of the inventions disclosed herein. For example, in the case of the hook and loop fastener shown on the inflatable belt in FIG. 1A, the hook and loop fastener may be exchanged and the function still maintained. In addition, the location of the input port may be in the middle of the inflatable belt instead of on one end. The body interface component, such as neoprene rubber, shown in FIG. 2 may be permanently attached the inflatable bladder, or it may be removable. If removable, the attachment means may be for example, hook and loop fasteners, and the fasteners may be along the edges or may run along the full width of both the inflatable bladder and body interface component. In the case the hook and loop fasteners run along the full width, they may be elastic such that the inflatable bladder may still inflate against the user's limb. As illustrated, there are many constructional permutations and combinations, and altering of various material properties which yield satisfactory results in an inflatable belt for use in a blood flow restriction system, and all such combinations and permutations and material property choices may be considered within the scope of this invention.

Belt Configurations

As has been discussed in both this application and patents to Sato, there are a variety of ways to form a belt around a user's limb and each has some advantages and disadvantages as discussed in the various applications. The reader may recognize that the inventive concepts disclosed herein may be considered adaptable, by changing, but limited to, the following: size, length, location, neighboring components, adding or removing one or more components, such as a loop coupler, material property, such as elasticity, etc. Such modifications represent numerous permutations and configurations which are too many to reasonably depict and describe herein, however the reader may understand that the applicant has thought of such reasonable applications, and may consider as such, part of the scope of this disclosed invention.

Although the description above contains many specifications, these should not be construed as limiting the scope of the invention but as merely providing illustrations of some of the presently preferred embodiments of this invention. Thus the scope of this invention should be determined by the appended claims and their legal equivalents, rather than by the examples given.

Purpose of Inflatable Belts

The previous discussion has extensively covered the use of the applicant's invention and inflatable belt 100 design in the context of a muscle development tool used for BFR training. However the applicant would like to point out that the generic construction can be useful for wrapping anything tight against the body, and not necessarily for the purpose of restricting blood flow.

Some purposes for this could be affixing, or otherwise integrating the design to clothing to pull a section of clothing tight against the arm, leg, or even waist as in a traditional belt. Such consideration may be useful for example in conjunction with an unweighting system where it is often difficult to have garments grab, or adhere to the body as a vertical force is applied. In this circumstance, the applications invention may serve to aid in wrapping or grabbing onto a body in order to lock and provide an anchor off of which to pull. The belt could be applied external to the garment or integrated into the garment, for example a pair of shorts, or a shirt. The shrinking belt portion may warp around the chest, or waist, or arms, or any part of the body so as to fulfill its purpose. Any sort of lifting or force transfer apparatus may be connected to the belt itself, or to a structure that is connected to the belt, such that the load is eventually transferred to the body in such a way that the belt helps with efficient and comfortable load transfer.

Another example may be applying compression in the case of a wrapping an ice bag or heating pad to the limb. In these cases, it is often difficult to get a good wrap on the limb, or requires a lot of plastic to wrap around in order to stay in place when the person stands up or wants to move from one spot to another. In these cases, a fast inflating sleeve that sounds an ice bag or heating pad, and that secures it tight to a limb may be particularly useful for quick on/off, and without wasting materials such as plastic wrap that is commonly used.

In any of these, or related use cases, the reader shall understand that all the designs, aspects, characteristics, methods, and inventions described in this application shall be applicable to such use cases, and this generic concept of securing a belt to a body segment make take advantage of the inventions described in this specification and the provided claims.

The reader shall note that these are but a few examples, and the general concept of using the applicants' invention to secure the belt to the body, or use the belt to secure an object to the body shall be considered within the scope of this invention.

What is claimed is:

1. A belt for securing to a body segment, wherein the belt may form a loop sized for positioning around the body segment in an open position, the belt comprising:
    an outer belt material;
    an inner belt material;
    a plurality of inflatable chambers between the outer belt material and the inner belt material, at least one of the plurality of inflatable chambers being inflatable to move the belt from the open position to a closed position;
    a means for fastening the belt comprising a first fastening means associated with a first end of the belt and a second fastening means associated with a second end of the belt, wherein the first fastening means associates with the second fastening means to fasten the belt;
    a loop coupler associated with an end of the belt;
    a stop mechanism associated with one of the first fastening means or the second fastening means which prevents the associated fastening means from exiting the loop coupler, wherein the stop mechanism comprises a physical barrier which mechanically interferes with the loop coupler;
    a handle associated with an end of the first fastening means or an end of the second fastening means; and
    at least one cutout relief between at least two of the plurality of inflatable chambers.

2. The belt of claim 1, wherein the plurality of inflatable chambers comprises polygonal chambers or curved chambers.

3. The belt of claim 1, wherein the plurality of inflatable chambers are formed with substantially non-stretch material.

4. The belt of claim 3, where the substantially non-stretch material is a fabric.

5. The belt of claim 1, wherein at least one of the plurality of inflatable chambers has a movable inner wall made of substantially non-stretch material.

6. The belt of claim 1, wherein at least one of the plurality of inflatable chambers has a movable outer wall made of substantially non-stretch material.

7. The belt of claim 1, wherein the inner belt material comprises inelastic material.

8. The belt of claim 1, wherein the belt further comprises an input port associated with at least one of the plurality of inflatable chambers.

9. The belt of claim 1, wherein the handle provides tension when pulled.

10. The belt of claim 1, wherein the belt further comprises a body interfacing component associated with the inner belt material.

11. The belt of claim 10, wherein the body interfacing component comprises a high friction surface.

12. The belt of claim 11, wherein the body interfacing component comprises a strip of neoprene closed-cell foam rubber.

13. The belt of claim 1, wherein the belt further comprises edging associated with at least one outer edge of the belt.

14. The belt of claim 1, wherein the belt further comprises a belt spring associated with the outer belt material.

15. The belt of claim 14, wherein the belt spring is located along a circumference of the belt under tension when the belt is in the closed position.

16. The belt of claim 15, wherein the belt spring comprises elastic stretch webbing.

* * * * *